United States Patent
Bacich et al.

(10) Patent No.: US 11,141,308 B2
(45) Date of Patent: *Oct. 12, 2021

(54) APPARATUS AND METHOD FOR EVERTING CATHETER FOR IUD DELIVERY AND PLACEMENT IN THE UTERINE CAVITY

(71) Applicant: CrossBay Medical, Inc., San Diego, CA (US)

(72) Inventors: Steven R. Bacich, Half Moon Bay, CA (US); Matthew Thomas Yurek, San Diego, CA (US); Jack Greelis, Carlsbad, CA (US); Piush Vidyarthi, San Rafael, CA (US)

(73) Assignee: CrossBay Medical, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/067,352

(22) Filed: Oct. 9, 2020

(65) Prior Publication Data

US 2021/0106457 A1    Apr. 15, 2021

Related U.S. Application Data

(63) Continuation-in-part of application No. 16/796,589, filed on Feb. 20, 2020, which is a continuation of (Continued)

(51) Int. Cl.
*A61F 6/18* (2006.01)
*A61M 25/00* (2006.01)
(Continued)

(52) U.S. Cl.
CPC ............... *A61F 6/18* (2013.01); *A61F 6/146* (2013.01); *A61M 25/003* (2013.01);
(Continued)

(58) Field of Classification Search
CPC .. A61F 6/18; A61F 5/003; A61F 6/146; A61F 6/148; A61F 6/16; A61F 6/20;
(Continued)

(56) References Cited

U.S. PATENT DOCUMENTS 3,421,509 A    1/1969 Fiore
3,452,749 A    7/1969 Riedell
(Continued)

FOREIGN PATENT DOCUMENTS

CN    103566683    2/2014
EP    0692273    1/1996
(Continued)

*Primary Examiner* — Ophelia A Hawthorne
(74) *Attorney, Agent, or Firm* — Levine Bagade Han LLP

(57) ABSTRACT

An everting balloon system is disclosed that can be used for the placement of an IUD within the uterine cavity of a female patient. The everting balloon system with IUD can be used to access a uterine cavity at specific locations in the fundus. A one-handed IUD delivery system for placement with an everting catheter is disclosed. An IUD loading system for placement within an everting catheter is disclosed. The everting catheter with an IUD can simplify the process of IUD placement within the uterine cavity.

16 Claims, 46 Drawing Sheets

Related U.S. Application Data application No. PCT/US2018/049234, filed on Aug. 31, 2018.

(60) Provisional application No. 62/913,160, filed on Oct. 9, 2019, provisional application No. 62/553,057, filed on Aug. 31, 2017.

(51) Int. Cl.
*A61F 6/14* (2006.01)
*A61M 25/01* (2006.01)

(52) U.S. Cl.
CPC .... *A61M 25/0075* (2013.01); *A61M 25/0119* (2013.01); *A61M 2025/0031* (2013.01); *A61M 2025/0034* (2013.01); *A61M 2210/1425* (2013.01)

(58) Field of Classification Search
CPC .... A61F 6/06; A61F 6/14; A61F 6/08; A61M 25/003; A61M 25/0075; A61M 25/0119; A61M 2025/0031; A61M 2025/0034; A61M 2210/1425; A61M 25/10; A61K 9/0036; A61B 17/12045; A61B 17/12027; A61B 2017/12127; A61B 2017/22051
See application file for complete search history.

(56) References Cited

U.S. PATENT DOCUMENTS

| | | | |
|---|---|---|---|
| 3,500,819 A | 3/1970 | Silverman | |
| 3,825,013 A | 7/1974 | Craven | |
| 3,882,852 A | 5/1975 | Sinnreich | |
| 3,911,927 A | 10/1975 | Rich et al. | |
| 3,982,544 A | 9/1976 | Dyck | |
| 4,271,839 A | 6/1981 | Fogarty et al. | |
| 4,323,072 A | 4/1982 | Rosenbluth et al. | |
| 4,654,027 A | 3/1987 | Dragan et al. | |
| 4,857,054 A * | 8/1989 | Helfer | A61M 25/104 604/99.03 |
| 4,863,440 A | 9/1989 | Chin | |
| 4,946,440 A | 8/1990 | Hall | |
| 5,074,845 A | 12/1991 | Miraki et al. | |
| 5,152,277 A | 10/1992 | Honda et al. | |
| 5,163,927 A | 11/1992 | Woker et al. | |
| 5,211,627 A | 5/1993 | William | |
| 5,259,836 A | 11/1993 | Thurmond et al. | |
| 5,284,473 A * | 2/1994 | Calabria | A61M 25/104 604/8 |
| 5,346,498 A | 9/1994 | Greelis et al. | |
| 5,364,345 A | 11/1994 | Lowery et al. | |
| 5,372,247 A | 12/1994 | Nishikawa | |
| 5,374,247 A * | 12/1994 | Lowery | A61M 25/0119 604/271 |
| 5,376,084 A | 12/1994 | Bacich | |
| 5,383,889 A | 1/1995 | Warner et al. | |
| 5,389,089 A | 2/1995 | Bauer | |
| 5,458,573 A | 10/1995 | Summers | |
| 5,472,419 A | 12/1995 | Bacich | |
| 5,531,219 A | 7/1996 | Rosenberg | |
| 5,630,797 A | 5/1997 | Diedrich et al. | |
| 5,662,582 A | 9/1997 | Levius et al. | |
| 5,724,994 A | 3/1998 | Simon et al. | |
| 5,902,286 A | 5/1999 | Reitz | |
| 5,925,058 A | 7/1999 | Smith et al. | |
| 5,954,688 A | 9/1999 | Adams et al. | |
| 5,964,223 A | 10/1999 | Baran | |
| 5,993,427 A | 11/1999 | Rolland et al. | |
| 6,039,721 A | 3/2000 | Johnson et al. | |
| 6,042,535 A | 3/2000 | Porter | |
| 6,080,129 A | 6/2000 | Blaisdell | |
| 6,090,083 A | 7/2000 | Sell | |
| 6,119,695 A | 9/2000 | Augustine et al. | |
| 6,379,372 B1 | 4/2002 | Dehdashtian et al. | |
| 6,398,775 B1 | 6/2002 | Perkins et al. | |
| 6,436,118 B1 | 8/2002 | Kayan | |
| 6,450,963 B1 | 9/2002 | Ackerman | |
| 6,526,917 B1 | 3/2003 | Anderson et al. | |
| 6,530,898 B1 | 3/2003 | Nimkar et al. | |
| 6,544,278 B1 | 4/2003 | Vrba et al. | |
| 6,588,429 B1 | 7/2003 | Wildemeersch | |
| 6,662,750 B2 | 12/2003 | Anderson et al. | |
| 6,708,056 B2 | 3/2004 | Duchon et al. | |
| 6,729,334 B1 | 5/2004 | Baran | |
| 6,860,235 B2 | 3/2005 | Anderson et al. | |
| 6,942,682 B2 | 9/2005 | Vrba et al. | |
| 7,080,647 B2 | 7/2006 | Wildemeersch | |
| 7,220,252 B2 | 5/2007 | Shah | |
| 7,320,325 B2 | 1/2008 | Duchon et al. | |
| 7,343,875 B2 | 3/2008 | Anderson et al. | |
| 7,406,969 B2 | 8/2008 | Duchon et al. | |
| 7,556,060 B2 | 7/2009 | Guala | |
| 7,647,891 B2 | 1/2010 | Anderson et al. | |
| 7,661,429 B2 | 2/2010 | Jutila | |
| 7,727,155 B2 | 6/2010 | De Ziegler | |
| 7,789,893 B2 | 9/2010 | Drasler et al. | |
| 7,794,488 B2 | 9/2010 | Vrba et al. | |
| 7,967,798 B2 | 6/2011 | Reydel et al. | |
| 8,118,774 B2 | 2/2012 | Dann et al. | |
| 8,221,403 B2 | 7/2012 | Sharkey et al. | |
| 8,377,109 B2 | 2/2013 | Vrba et al. | |
| 8,479,742 B2 | 7/2013 | Laplaca | |
| 8,551,001 B2 | 10/2013 | Connor et al. | |
| 8,573,222 B2 | 11/2013 | Weintraub | |
| 8,584,679 B2 | 11/2013 | Lowe et al. | |
| 8,926,559 B2 | 1/2015 | Chin | |
| 9,028,401 B1 | 5/2015 | Bacich et al. | |
| 9,101,391 B2 | 8/2015 | Bacich et al. | |
| 9,168,164 B2 | 10/2015 | Dorn et al. | |
| 9,180,039 B2 | 11/2015 | Tal et al. | |
| 9,259,233 B2 | 2/2016 | Gruber et al. | |
| 9,265,651 B2 | 2/2016 | Pandit | |
| 9,308,119 B2 | 4/2016 | Weintraub | |
| 9,326,790 B2 | 5/2016 | Chin et al. | |
| 9,452,082 B2 | 9/2016 | Lyytikainen et al. | |
| 9,492,312 B2 | 11/2016 | Cappiello et al. | |
| 9,510,088 B2 | 11/2016 | Tal et al. | |
| 9,610,191 B2 | 4/2017 | Tal et al. | |
| 9,615,965 B2 | 4/2017 | Lyytikainen et al. | |
| 9,668,912 B2 | 6/2017 | Jutila et al. | |
| 9,707,123 B2 | 7/2017 | Lyytikainen et al. | |
| 9,795,408 B2 | 10/2017 | Chin et al. | |
| 9,949,756 B2 | 4/2018 | Bacich | |
| 9,949,870 B2 | 4/2018 | Frankenne et al. | |
| 10,004,624 B2 | 6/2018 | Dorn et al. | |
| 10,022,264 B2 | 7/2018 | Tai et al. | |
| 10,028,858 B2 | 7/2018 | Deckman et al. | |
| 10,034,986 B2 | 7/2018 | Yurek et al. | |
| 10,149,784 B2 | 12/2018 | Jutila et al. | |
| 10,213,329 B2 | 2/2019 | Cully et al. | |
| 10,245,074 B2 | 4/2019 | Bacich et al. | |
| 10,398,588 B2 | 9/2019 | Tai et al. | |
| 10,561,524 B2 | 2/2020 | Lyytikäinen et al. | |
| 10,582,951 B2 | 3/2020 | Bacich | |
| 10,583,035 B2 | 3/2020 | Lyytikäinen et al. | |
| 10,646,209 B2 | 5/2020 | Chin et al. | |
| 10,646,256 B2 | 5/2020 | Bacich et al. | |
| 10,820,927 B2 | 11/2020 | Bacich et al. | |
| 2002/0108614 A1 | 8/2002 | Schultz | |
| 2002/0111602 A1 | 8/2002 | Ackerman et al. | |
| 2003/0023263 A1 | 1/2003 | Krolik et al. | |
| 2003/0208223 A1 | 11/2003 | Kleiner | |
| 2004/0231668 A1 | 11/2004 | Kates | |
| 2005/0015047 A1 | 1/2005 | Shah | |
| 2005/0154415 A1 | 7/2005 | Fogarty et al. | |
| 2005/0277811 A1 | 12/2005 | Richards et al. | |
| 2007/0203472 A1 | 8/2007 | Nachmani | |
| 2008/0167629 A1 | 7/2008 | Dann et al. | |
| 2008/0183038 A1 | 7/2008 | Tilson et al. | |
| 2009/0126731 A1 | 5/2009 | Dunsmore et al. | |
| 2009/0199848 A1 | 8/2009 | Sharratt | |
| 2009/0293873 A1 | 12/2009 | Djupesland et al. | |
| 2009/0299327 A1 | 12/2009 | Tilson et al. | |

(56) References Cited

U.S. PATENT DOCUMENTS

| | | |
|---|---|---|
| 2010/0086492 A1 | 4/2010 | Lee-sepsick et al. |
| 2010/0147701 A1 | 6/2010 | Field |
| 2011/0060276 A1 | 3/2011 | Schaeffer et al. |
| 2011/0313400 A1 | 12/2011 | Boatman |
| 2012/0035471 A1 | 2/2012 | Lee-Sepsick et al. |
| 2012/0065674 A1 | 3/2012 | Levy |
| 2012/0230915 A1 | 9/2012 | Exalto et al. |
| 2013/0060234 A1 | 3/2013 | Besser et al. |
| 2013/0178785 A1 | 7/2013 | Papay et al. |
| 2013/0253426 A1 | 9/2013 | Campbell et al. |
| 2014/0114261 A1 | 4/2014 | Geppert et al. |
| 2014/0155745 A1 | 6/2014 | Duncan |
| 2014/0166011 A1 | 6/2014 | Pierro et al. |
| 2014/0276432 A1 * | 9/2014 | Bierman ............ A61B 17/3498 604/164.1 |
| 2014/0283820 A1 | 9/2014 | Flickinger et al. |
| 2015/0040902 A1 | 2/2015 | Blum |
| 2015/0065951 A1 | 3/2015 | Freyman et al. |
| 2015/0066068 A1 | 3/2015 | Hirszowicz et al. |
| 2015/0133727 A1 | 5/2015 | Bacich et al. |
| 2015/0133779 A1 | 5/2015 | Yurek et al. |
| 2015/0142045 A1 * | 5/2015 | Bacich ................ A61F 2/0027 606/193 |
| 2015/0335354 A1 | 11/2015 | Carson et al. |
| 2016/0278747 A1 | 9/2016 | Chin et al. |
| 2017/0354437 A1 | 12/2017 | Bacich |
| 2018/0235660 A1 | 8/2018 | Bacich |
| 2018/0333545 A1 | 11/2018 | Yurek et al. |
| 2018/0360424 A1 | 12/2018 | Yurek et al. |
| 2019/0009058 A1 | 1/2019 | Bacich et al. |
| 2019/0126010 A1 | 5/2019 | Sarna et al. |
| 2019/0167308 A1 | 6/2019 | Bacich et al. |
| 2019/0223913 A1 | 7/2019 | Bacich et al. |
| 2019/0366048 A9 | 12/2019 | Bacich et al. |
| 2020/0023162 A1 | 1/2020 | Bacich et al. |
| 2020/0163699 A1 | 5/2020 | Bacich et al. |
| 2020/0206463 A1 | 7/2020 | Bacich et al. |
| 2020/0297384 A1 | 9/2020 | Bacich et al. |
| 2020/0330131 A1 | 10/2020 | Bacich et al. |
| 2021/0106458 A1 | 4/2021 | Bacich et al. |

FOREIGN PATENT DOCUMENTS

| | | | |
|---|---|---|---|
| EP | 0359489 | 3/2000 | |
| WO | WO 1993/007927 | 4/1993 | |
| WO | WO 1994/025099 | 11/1994 | |
| WO | WO 1997/021461 | 6/1997 | |
| WO | WO 2009/042621 | 4/2009 | |
| WO | WO 2010/055701 | 5/2010 | |
| WO | WO 2015/069952 | 5/2015 | |
| WO | WO 2017/151918 | 9/2017 | |
| WO | WO 2019/010244 | 1/2019 | |
| WO | WO 2019/046800 | 3/2019 | |
| WO | WO-2019046800 A1 * | 3/2019 | ............ A61M 25/00 |
| WO | WO 2021/072261 | 4/2021 | |

* cited by examiner

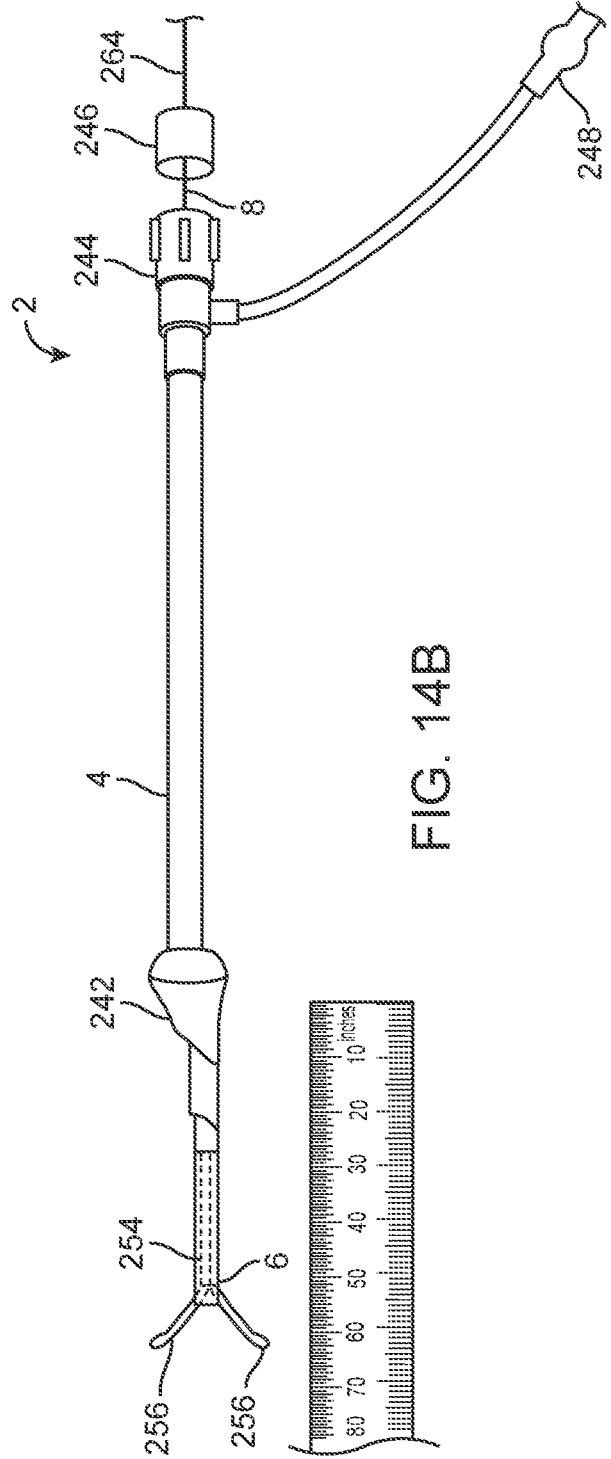
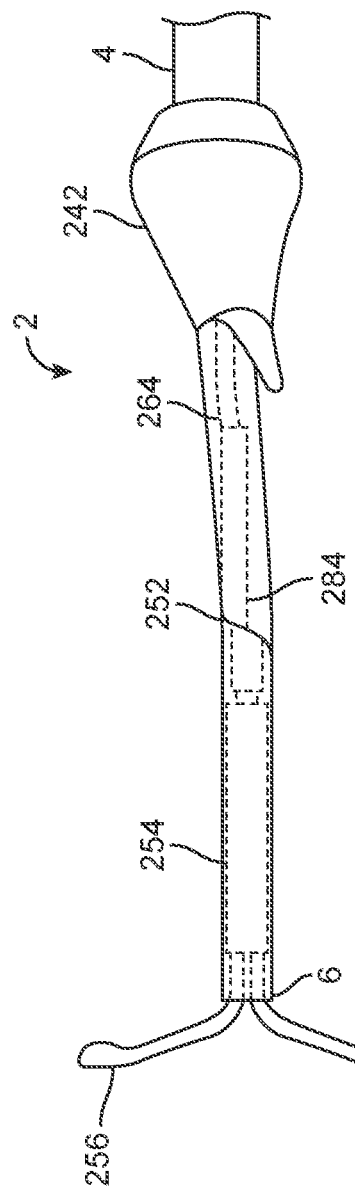
FIG. 14B
FIG. 14C

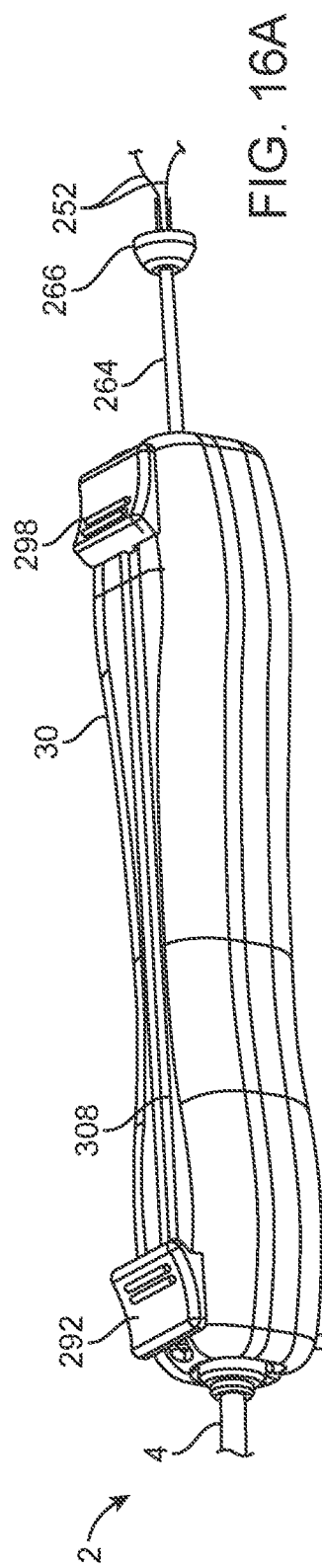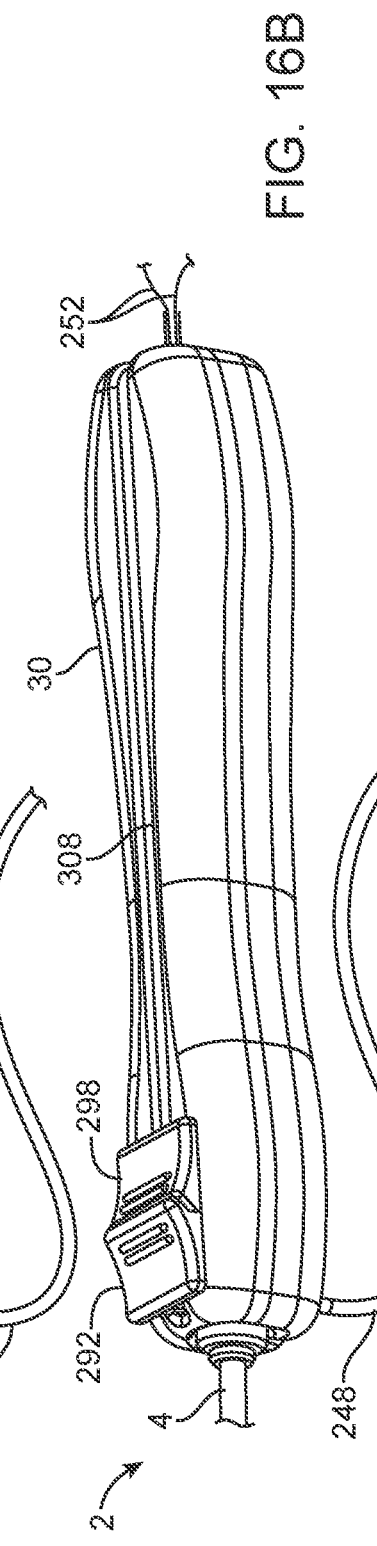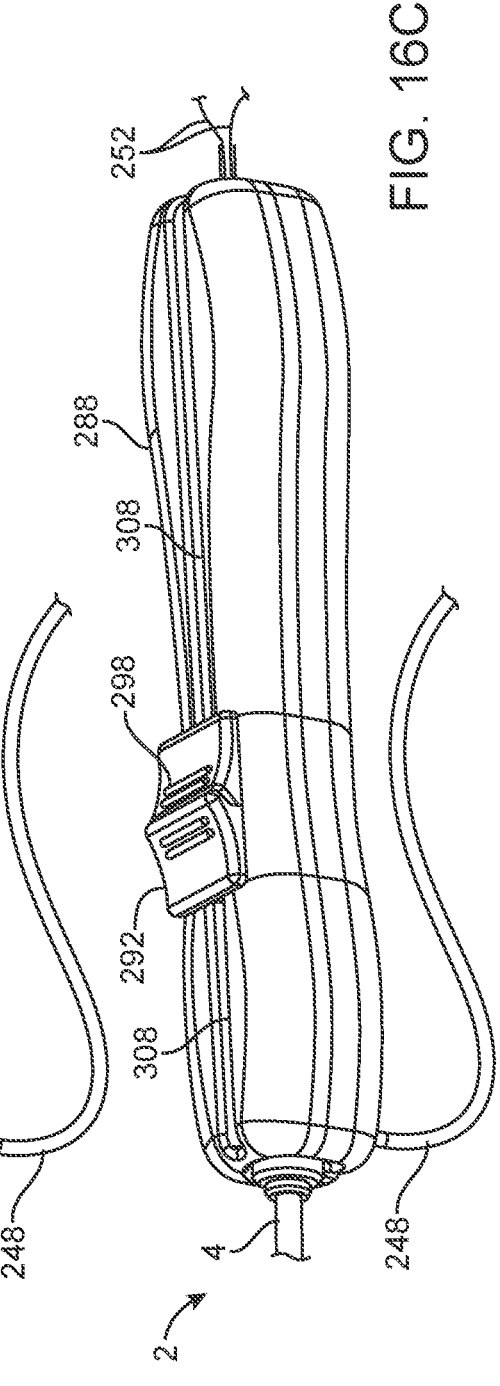

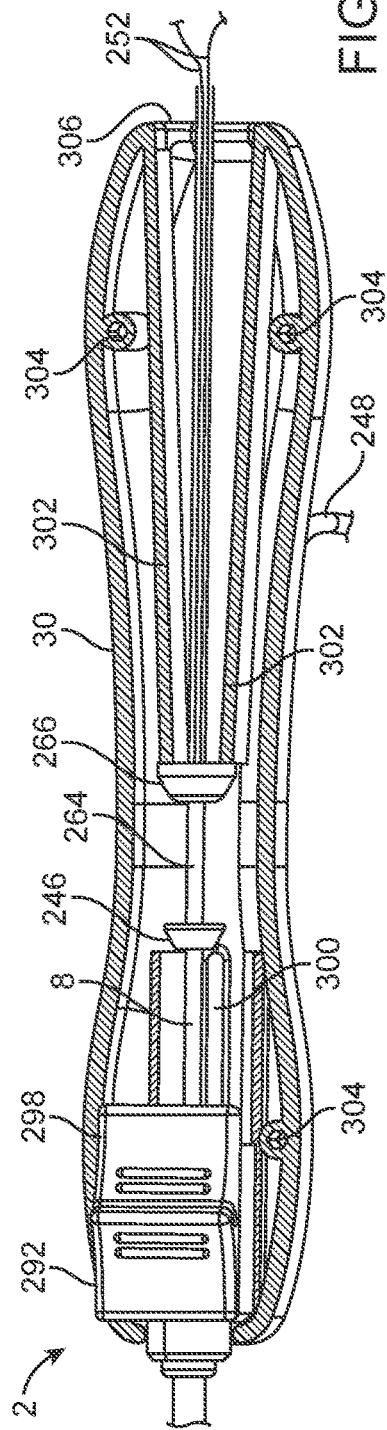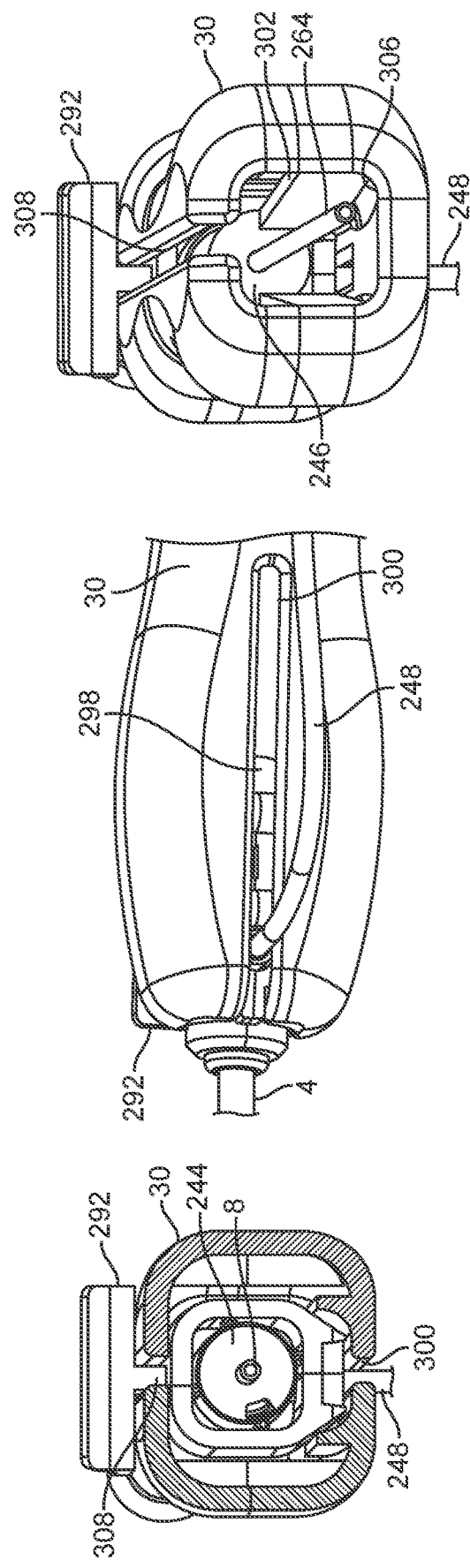
FIG. 16D
FIG. 16G
FIG. 16F
FIG. 16E

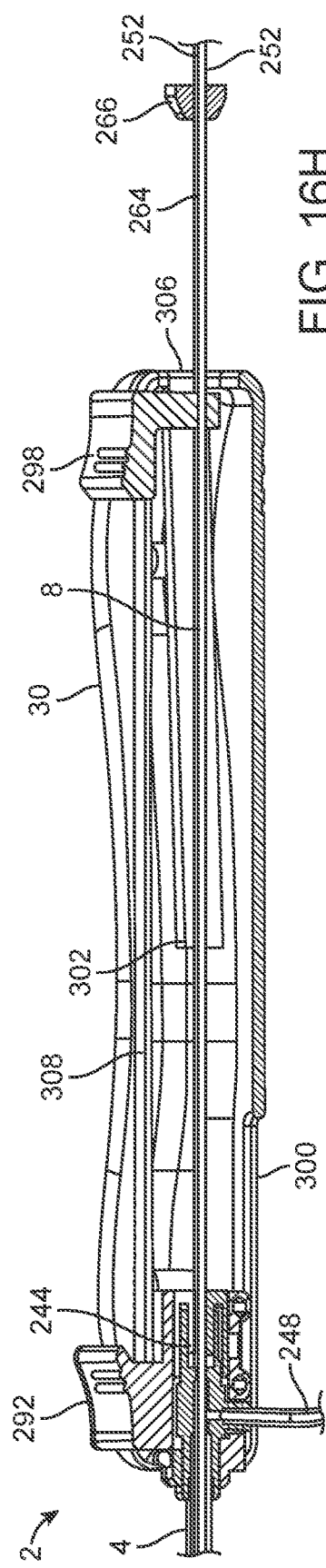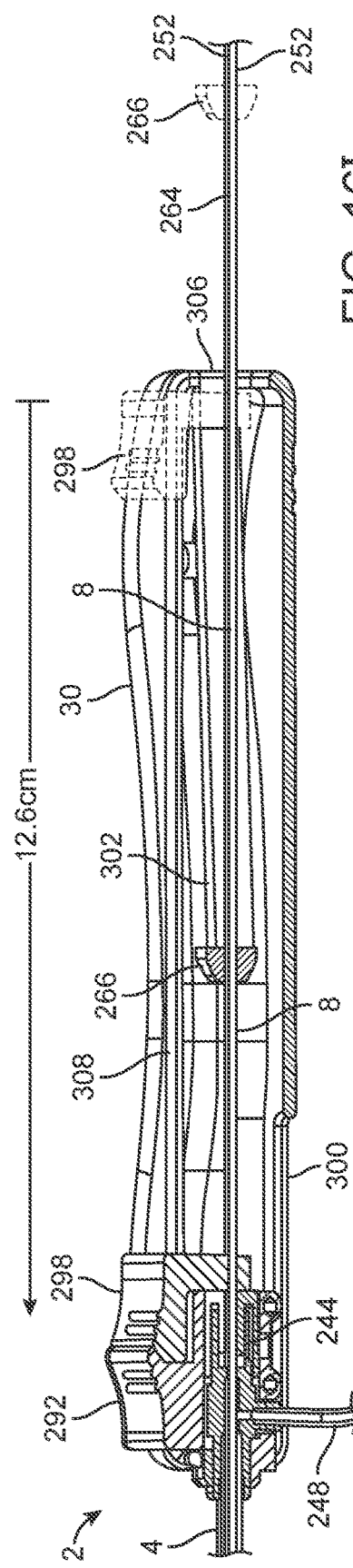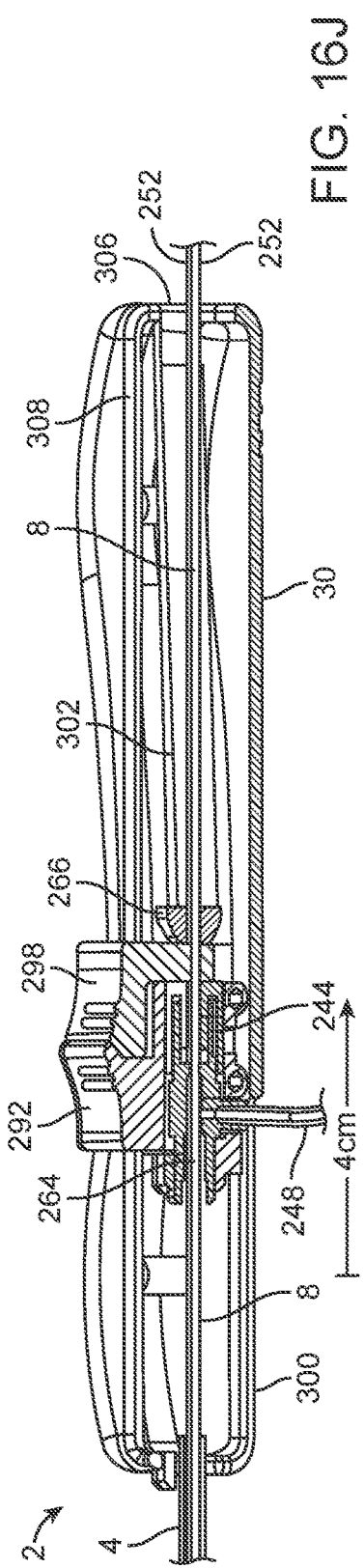

APPARATUS AND METHOD FOR EVERTING CATHETER FOR IUD DELIVERY AND PLACEMENT IN THE UTERINE CAVITY

CROSS-REFERENCE TO RELATED APPLICATIONS

This application claims priority to U.S. Provisional Application No. 62/913,160, filed Oct. 9, 2019, which is incorporated by reference herein in its entirety, and is a continuation-in-part of U.S. application Ser. No. 16/796,589, filed Feb. 20, 2020, which is a continuation of U.S. International Application No. PCT/US2018/049234, filed Aug. 31, 2018, which claims priority to U.S. Provisional Application No. 62/553,057, filed Aug. 31, 2017.

BACKGROUND

The apparatuses and methods disclosed herein can have utility for everting catheters that are characterized with an inner catheter, outer catheter, and everting membrane that can be connected to both catheters. The inner catheter may contain an inner lumen to pass fluid or media, drugs or therapeutic agents, instruments or devices such as intrauterine uterine devices (IUDs), endoscopes, and other catheters.

For physicians and medical professionals, accessing systems for vessels and bodily cavities in patients have typically used various guidewire and catheter technologies. In some cases, the process requires the insertion of a series of mandrels or wires to increase the lumen diameter for the eventual passage of a larger bore instrument within the vessel. This technique can be referred to as "Dottering" or in the case of accessing the cervical canal and uterus, physicians will use a series of increasing diameter mandrels known as Hegar dilators. In the techniques described above, the methods involved pushing an object, mandrel, or device through the vessel to gain access to a desired region in the body. The result of pushing an object, mandrel, or device creates shear forces on the lumen wall. In some cases, the shear forces can result in trauma, pain for the patient, or perforation.

In contrast, another access technology that has been used in prior art is referred to as an everting catheter. Everting catheters utilize a traversing action in which a balloon is inverted and with the influence of hydraulic pressure created by a compressible or incompressible fluid or media, rolls inside out or everts with a propulsion force through the vessel. Everting balloons have been referred to as rolling or outrolling balloons, evaginating membranes, toposcopic catheters, or linear everting catheters such as those in U.S. Pat. Nos. 5,364,345; 5,372,247; 5,458,573; 5,472,419; 5,630,797; 5,902,286; 5,993,427; 6,039,721; 3,421,509; and 3,911,927; all of which are incorporated herein by reference in their entireties. These are categorized as everting balloons and are for traversing vessels, cavities, tubes, or ducts in a frictionless manner. In other words, an everting balloon can traverse a tube without imparting any shear forces on the wall being traversed. Because of this action and lack of shear forces, resultant trauma can be reduced and the risk of perforation reduced. In addition, as a result of the mechanism of travel through a vessel, material and substances in the proximal portion of the tube or vessel are not pushed or advanced forward to a more distal portion of the tube or vessel.

In addition, as the everting catheter deploys inside out, uncontaminated or untouched balloon material is placed inside the vessel wall. In the inverted or undeployed state, the balloon and the IUD are housed inside the catheter body and cannot come into contact with the patient or physician. As the balloon is pressurized and everted, the balloon material rolls inside out without contacting any element at the entrance outside of the vessel. For the delivery of IUDs, the action of the balloon material rolling inside out also prevents the IUD to contact any element at the vaginal wall, exocervix, endocervical canal, and depending upon the depth of insertion, the internal cervical os of the patient. Another advantage of an everting balloon catheter is that the method of access is more comfortable for the patient since the hydraulic forces "pull" the balloon membrane through the vessel or duct as opposed to a standard catheter that needs to be "pushed" into and through the vessel or duct. For the delivery of IUDs, the hydraulic forces "pull" the balloon membrane and IUD through the cervix and into the uterine cavity as opposed to a standard IUD catheter tube that needs to be "pushed" into and through the cervix and into the uterine cavity.

For access to the uterine cavity with larger devices, the method typically used by physicians for accessing the cervical canal in women requires the use of multiple instruments of increasing diameter. The physician will use a small uterine sound or small diameter probe or Hegar device for gaining initial entry into the uterus via the cervix. Ever increasing sizes of Hegars are used to stretch the cervical muscles until the desired internal diameter is achieved for the insertion of a secondary instrument such as an endoscope or other device. This process can be particularly difficult in some nulliparous women who are seeking contraception with an IUD or women elect to use a hormonal IUD for alleviating abnormal bleeding. Post-menopausal women can also present with very small diameter cervical canals. A cervix could be difficult to traverse as a result of prior surgery, underlying stenosis, or other anatomical configuration or tortuosity that makes the passage of instruments or Hegar dilators difficult.

There are some cervical dilators that provide radial expansion to open the cervical canal to a greater internal diameter without the insertion of multiple instruments. All of these devices are predicated on first crossing or traversing the cervical canal prior to the step of radial expansion. Once traversed through the cervical canal, these devices use either mechanical means or the expansion of a balloon dilation member that is concentric on the exterior of the dilator probe. If the cervical canal is particularly tight or narrow, a small diameter probe or mandrel may be required to first cross the cervix and access the uterine cavity. As mandrels or instruments get smaller in diameter, the likelihood of perforation or a false passage increases. In any case, these cervical dilators require passage or crossing by the initial probe prior to any further radial expansion being performed.

Everting catheters have been described as dilatation catheters. Representative examples of dilating everting catheters include U.S. Pat. Nos. 5,364,345 and 4,863,440, both of which are incorporated by reference herein in their entireties.

Everting catheters have also been described with additional elements such as a handle for controlling instruments within an everting catheter. A representative example is U.S. Pat. No. 5,346,498 which is incorporated by reference herein in its entirety. Everting balloon catheters can be constructed with an inner catheter with an internal lumen or through-lumen (or thru-lumen). The through-lumen can be used for the passage of instruments, media, materials, therapeutic agents, endoscope, guidewires, or other instruments or devices. Representative samples of everting catheters with through-lumens are in U.S. Pat. Nos. 5,374,247 and 5,458,573. In addition, everting catheters have been described with waists or a narrowing of the balloon diameter, such as in U.S. Pat. No. 5,074,845, which is incorporated by reference herein in its entirety.

Everting catheters are particularly useful for accessing the uterine cavity where the endocervical canal may be stenotic, tortuous, or contain the presence of a C-section scar or other anatomical configuration that makes the passage of instruments difficult for the physician. This in turn can lead to an uncomfortable procedure for the patient.

One common gynecological procedure is the placement of IUDs for women who are either seeking a non-permanent method of birth control or medication from an intrauterine device that elutes hormonal treatment for abnormal uterine bleeding, painful periods, or other medications that may be placed by an implant in the uterine cavity. IUDs can contain copper and can be configured in numerous configurations. In all of these cases, the physician needs to place the device within the uterine cavity.

For the placement of IUDs in the uterus, IUD inserters consist of fairly stiff tubes or cannula for insertion. The IUD implant itself can be configured in a "T-shape" or "Y-shape" in its natural, uncollapsed state in which the three arms of the "T" or "Y" are constructed as rigid members that can flex, but are not easily bent in a tight radius less than 0.500". The "T" or "Y" configuration is needed to maintain the IUD within the uterine cavity during the normal activities of the woman and otherwise more forceful activities such as exercise, coughing, and the uterine contractions that occur with menses. In these situations, the "T" or "Y" shape is needed to prevent expulsion or migration from the uterine cavity since the arms of the "T" or "Y" are designed to keep the IUD near the patient's fundus with its rounded ends approximating the bilateral cornua of the uterine cavity. Not all IUDs are "T" or "Y" shaped and other configurations including circular or coiled shaped are known or available commercially.

In clinical use during device placement, the endocervix may have multiple turns and curvatures that contain tight radii curves. For placement through the endocervix and to straighten the cervical canal to reduce the amount of curvature, the physician needs to grasp the cervix and maintain counter-traction on the cervix. Besides straightening the cervix, the counter-traction facilitates pushing the IUD inserter through the endocervical canal and into the uterine cavity. Misplacements, perforations, or the inability to place the IUD, are all known and recognized outcomes or adverse events with an IUD placement procedure. The stiffness of the cannula and the IUD implant itself also leads to patient discomfort during the placement procedure. This is particularly true for women who have stenotic cervices or who are nulliparous.

Once the IUD is in the proper position in the patient, the IUD inserter can have a cannula that is attached to a handle that allows the physician to translate the IUD from out of the distal end of the cannula. The handle allows the physician to perform the placement procedure with one hand.

Following the placement of the IUD in the uterine cavity, the IUD inserter is withdrawn from the patient. The retrieval suture or sutures of the IUD remains in the patient's endocervical canal when sliding the inserter out of the cervix. Once removed, the physician can trim the visible sutures extending from the exocervix. The IUD sutures are visible in the patient's vagina emanating from the exocervix and can be trimmed to length as indicated by the IUD manufacturer's labeling.

Also, when delivering an IUD, instruments, devise, and reproductive materialsuch as an embryo, into the uterine cavity, the access system can push cervical mucus or fluids and materials from the vagina into the uterine cavity. There is a potential that these fluids and materials from the vagina could promote bacterial infection. The action of the unrolling balloon is designed to minimize this effect.

In addition, access systems for the uterine cavity can create a vacuum effect when the access system is being withdrawn or removed from the uterine cavity. This vacuum effect can unintentionally remove the reproductive material from the uterine cavity in the situation of embryo transfer. In existing systems, when the transfer catheter is retracted from a second outer or guiding catheter (e.g., the "inner" catheter), the retraction produces vacuum pressure within the uterine cavity. This vacuum pressure is created in the uterine cavity by the removal and backward movement of the transfer catheter within the inner catheter. After the embryo transfer is completed, an embryologist may inspect the transfer catheter to verify that the embryos or reproductive material was indeed deposited in the uterus and not pulled back into the transfer catheter because of the vacuum effect. The same procedure may be done for the outer catheter once this catheter is removed. For IUD placement, having a system that can potentially reduce vacuum effect can lead to more reliable and exact IUD placement.

Further, everting balloons describe an action in which a balloon is inverted and, with the influence of hydraulic pressure created by a compressible or incompressible fluid or media, rolls inside out or everts with that propulsion force. Everting balloons have been referred to as rolling or outrolling balloons, evaginating membranes, toposcopic catheters, or linear everting balloons. These are all categorized as everting balloons due to their property of traversing vessels, cavities, tubes, or ducts in a substantially frictionless manner. Everting balloons can traverse a tube without imparting any significant shear forces on the wall being traversed. Because of this action and lack of shear forces, material and substances in the proximal portion of the tube or vessel are pushed or advanced forward to a more distal portion of the tube or vessel. For example for 1 everting balloons in the female reproductive tract, potentially infectious substances from the vagina, cervical os or exocervix, or the legs or other anatomy of the patient, and the hands of the physician during insertion or catheter preparation, are not in contact with the everted balloon that resides in the catheter system prior to deployment in the patient. The objective of keeping the everting balloon isolated from potentially uncleanly surfaces is to reduce post-procedural infections.

SUMMARY OF THE INVENTION

An everting balloon system is disclosed. The everting balloon system can be used for IUD placement, delivery of instruments, devices, and endoscopes, and insemination, urinary incontinence, dilation of a body lumen, for access and sealing within a body cavity, or combinations thereof. The system can have automatic deployment and disengagement. The system can have a handle for insertion. The system can have a motorized air or fluid pump or pressurization source. The system can have inner and outer catheters that can automatically disengage upon everting.

The everting balloon system can have an intubating base with a locking balloon that can activate upon pressurization. The system can be a compact, low profile unit used in vivo.

The system can be single use and disposable. The system can be non-irritation and non-infection causing.

The everting balloon system can be used for cervical access, dilation, and the delivery of IUDs. The everting balloon system can have a system handle mechanism that can enable a one-handed operating technique by the user. The one-handed operating technique can include advancement and pressurization of the everting balloon membrane within the control of the user with one hand.

The everting balloon system can be used for the insertion of drug delivery devices, or insemination, and can seal the cervix for a duration of time for the deposition of drug agent or sperm and to allow for mobility for the patient. The everting balloon system can have a decoupling mechanism configured to decouple the outer catheter and inner catheter while maintaining hydraulic pressure in an everting balloon. The system can deflate and removal the everting balloon concurrently.

The system can be used to place or deliver fallopian tube inserts (i.e., intratubal inserts, such as the Essure device from Bayer Corporation) in fallopian tubes. The system can access the intramural and isthmic portions of the fallopian tube. All or part of the everting catheter system can be loaded into a hysteroscope and placed with direct endoscopic visualization.

The everting catheter system can be a selective fallopian tube catheter with a curved distal end section and angled ball tip. This configuration can be performed by ultrasound or radiographic visualization.

One or more fallopian tube occluding devices (e.g., the Essure device) can be loaded into the everting balloon system, for example, in the through lumen of the inner catheter. Once fully everted and placed into the fallopian tube, the everting balloon system, such as the inner catheter, can be withdrawn from the fallopian tube while leaving the fallopian tube occluding device in the fallopian tube. Once the everting balloon system is withdrawn from the fallopian tube, the fallopian tube occluding can be deployed (e.g., device anchors such as coils can be extended, or a resilient porous matrix can expand to friction fit the tube lumen). Once the fallopian tube occluding device is deployed, a central guidewire can be removed from the fallopian tube. The procedure can be repeated for the contralateral fallopian tube.

The everting balloon system can be used to access the bladder, ureters, kidneys, or combinations thereof. Devices, tools, instrumentation, endoscopes, drugs, therapeutic agents, sampling devices (brushes, biopsy, and aspiration mechanisms), or combinations thereof can be delivered through the inner catheter lumen to the target site.

Specialized everting catheter systems with specific instruments, tools, or functions built or placed within the everting catheter system are also disclosed herein. Examples of such tools or instruments are biopsy devices, cytology devices, drug delivery mechanisms, fluid delivery mechanisms, endoscopes, IUDs, or other tools to be delivered into a bodily cavity, a bodily space, a potential bodily space that is created by the everting balloon mechanism, or a bodily vessel. There are several advantages to having an IUD built or placed into the everting catheter system as the delivery mechanism. The everting balloon can be used to pull the IUD implant into the uterine cavity without requiring the physician or operator to push an inserter through the endocervix and into the uterine cavity. This is particularly useful for tortuous or tight cervices. In addition, the everting membrane rolls inside-out through passageways in a frictionless manner without imparting shear forces on the inner lumen wall. The everting balloon works to protect the body passageway from the distal end profile of the IUD while pulling the IUD into the desired location.

The IUD can be fixed to the everting catheter system and automatically extends beyond the distal end of the everting balloon by being pulled by the everting balloon into the uterine cavity. During the eversion process, the IUD can be shielded from the body tissue until it extends beyond the distal end of the everting balloon. In this process the IUD will not contact the vagina, exocervix, or other fluids, mucus, or tissue in the proximal region of the endocervix. Providing the IUD at a specific distance in the everting catheter system can provide the physician the ability to direct the IUD to an exact distance from the exocervix or specific location in the uterine cavity.

An IUD placement procedure can be performed or delivered in particular locations in the uterine cavity.

An everting membrane for IUD placement can be designed for one-handed placement.

An everting membrane for IUD placement can be designed for one-handed placement with automatic negative pressure during the release of the IUD.

An everting membrane for IUD placement can be designed for one-handed placement with automatic or manual irrigation through the central lumen during the release of the IUD. The automatic irrigation can facilitate device placement by releasing the IUD from the everting membrane. Irrigation through the central lumen prior to loading the IUD within an everting catheter, or the delivery and release of the IUD in the everting membrane, by increasing the lubricity or the IUD within the everting membrane so that the IUD can slide out of the everting membrane with reduced friction. Equipping the everting catheter for IUD delivery and placement with an irrigation function is especially useful since some IUDs contain hormonal drugs, coatings, or other therapeutic agents that can be tacky when interacting against the surface of certain polymers that are useful in catheter fabrication.

The irrigation mechanism, whether done automatically or manually, can be used to facilitate device visualization in the uterine cavity using ultrasonography, fluoroscopy, or direct visualization with an endoscope through the central lumen of the IUD inserter. The injection of saline as an example with the irrigation mechanism through the central lumen can provide the physician a slightly distended uterine cavity in which ultrasonographic visualization of the IUD in the uterine cavity for confirmation of IUD placement.

The IUD system can have a transfer mechanism to facilitate the loading of commercially available or second party IUDs in the everting catheter. Once loaded with the IUD, the everting catheter is ready for placement into the patient's uterus. The transfer mechanism includes a loading apparatus of retrograde loading the second-party IUD into the distal end of everting membrane and a snare for capturing and retracting the IUD sutures through the central lumen of the everting catheter. The entire mechanism is contained within a flat stand that will fit on a standard procedure prep table. In operation, the loading mechanism can facilitate loading of a second party IUD within an everting catheter prior to delivery into a patient.

An everting catheter system for an IUD placement procedure can be a facilitated by an aspiration system for holding onto the device during the initial steps of device loading. The aspiration system can work in conjunction with the distal end opening of a pusher through the central lumen of the everting catheter to stabilize and pull the IUD into position with the everting membrane of the everting catheter system.

An everting catheter system for an IUD placement procedure can utilize a translatable outer catheter with telescoping sections that provides selected insertion depths within the uterine cavity for IUD device placement. Telescoping sections in the outer catheter can independently change and select the insertion depth of the IUD placement without altering any other component of the everting catheter system.

The distal end of the everting membrane at the location of the IUD can have an echogenic marker for increased ultrasound contrast, visibility, and detection within the patient's uterus or enhanced real time visualization of IUD placement.

An IUD loading system can allow the user to load a separately supplied IUD into an everting catheter system. The loading system can include a cradle, split tube, and tray fixture to facilitate IUD loading into the everting catheter system.

Another embodiment uses a derivation of the loading system within the manufacturing process during the construction of an integrated everting system with a pre-loaded IUD.

BRIEF DESCRIPTION OF THE DRAWINGS

FIGS. 14A through 14D illustrate further embodiments demonstrating the advancement and release of an IUD within an everting membrane.

FIGS. 16A to 16J illustrate a variation of an everting catheter that can deliver an IUD within the uterine cavity.

DETAILED DESCRIPTION

Figure 1A:
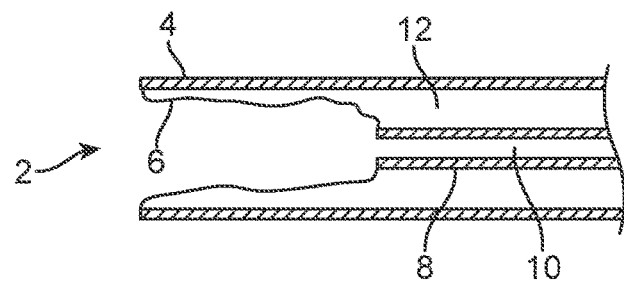
FIGS. 1A through 1E are longitudinal cross-sectional views of the distal end of a variation of a method for using the everting balloon system.

An everting balloon system 2 (also referred to as an everting catheter system) that can be used to traverse a vessel, such as the cervical canal is disclosed. The everting balloon system 2 can be used to access the uterine cavity via the cervix. The cervical canal is a single lumen vessel that can stretch or dilate. The everting balloon system 2 can have a control system that can be operated with one hand. The everting catheter system can also traverse other locations in the body of a patient or animal for the purposes of placement of a device within a bodily cavity or lumen.

FIGS. 1A through 1E illustrate that an everting catheter system 2 can have a radially outer catheter 4, a balloon membrane 6, and a radially inner catheter 8. The inner catheter 8 can have an inner catheter lumen 10 (e.g., a through-lumen). The distal end of the inner catheter lumen 10 can be open or closed. The inner catheter 8 can have the inner catheter lumen 10 or be a solid rod or flexible mandrel. The everting balloon system 2 can have a media volume 12. The media volume 12 can be the contiguous open volume between the inner catheter 8 and outer catheter 4 that is proximal to the balloon membrane 6. A radially outer terminal perimeter of the balloon membrane 6 can be attached to the distal terminal end of the outer catheter 4. A radially inner terminal perimeter of the balloon membrane 6 can be attached to the distal terminal end of the inner catheter 8. The everting balloon system 2 can be made without an inner catheter 8, for example with the balloon membrane 6 extending proximally out of the working area to a control device (e.g., a pump).

FIG. 1A illustrates that the everting catheter system 2 can be in an unpressurized configuration. The media volume 12 can be uninflated and unpressurized. The balloon membrane 6 can be slack.

Figure 1B:
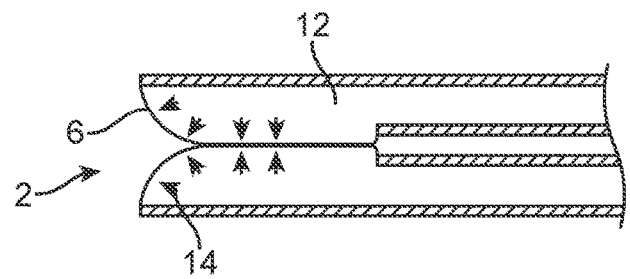

FIG. 1B illustrates that that everting catheter system 2 can be in a pressurized and uneverted configuration. A pressurization device, such as a pump, for example at the proximal end of the everting catheter system 2 can be in fluid communication with the media volume 12. The pressurization device can deliver a fluid media, such as a pneumatic gas or hydraulic liquid media (e.g., saline, water, air, carbon dioxide, or combinations thereof), at a media pressure 14 to the media volume 12. The media pressure 14 in the everting balloon 2 can be from about 2 to about 5 atmospheres of pressure when in the everted configuration and higher media pressures 14 from about 5 atmospheres to 10 atmospheres are possible, for example, to provide greater everting capability for more difficult or stenotic passageways in the body.

The balloon membrane 6 can inflate and be in tension. The balloon membrane 6 can block the distal port of the inner catheter lumen 10.

Figure 1C:
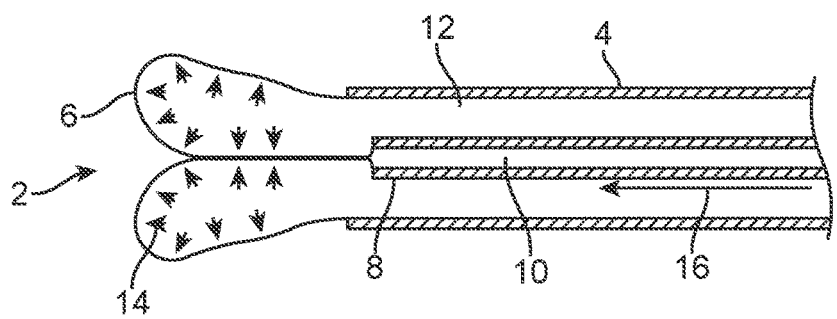

FIG. 1C illustrates that the everting catheter system can be in an inflated and partially everted configuration. The inner catheter 8 can be translated distally, as shown by arrow 16, with respect to the outer catheter 4, and out of the outer catheter 4. The distal terminal end of the inner catheter 8 can be proximal of the distal terminal end of the balloon membrane 6. The distal terminal end of the inner catheter 8 can be proximal or terminal of the distal terminal end of the outer catheter 4. The balloon membrane 6 can block the distal port of the inner catheter lumen 10 or can be open allowing fluid communication between the inner catheter lumen 10 and the target site.

Figure 1D:
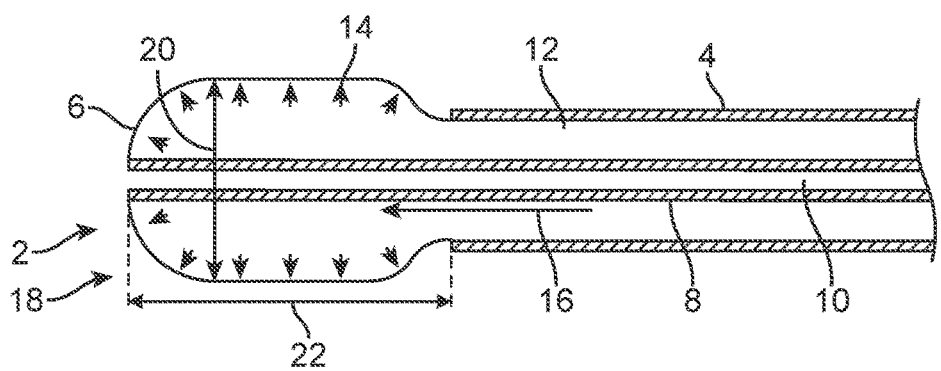

FIG. 1D illustrates that the everting catheter system can be in an inflated, fully everted, and fully distally extended configuration. The inner catheter 8 can be translated distally, as shown by arrow 16, with respect to the outer catheter 4 until the distal terminal end of the inner catheter 8 is longitudinally beyond or co-terminal with the distal terminal end of the balloon membrane 6. The distal port of the inner catheter lumen 10 can be unobstructedly accessible and in fluid communication with the target site.

In the fully inflated configuration, the balloon membrane 6 can form an inflated everting balloon 18. The everting balloon 18 can have a balloon outer diameter 20 and balloon length 22 in the inflated and fully everted configuration.

The balloon outer diameter 20 can be from about 2 mm to about 20 mm, more narrowly from about 2 mm to about 7 mm, for example about 5 mm. The outer diameter can be constant or vary along the length of the everting balloon 18. For example, for use in the cervical canal, the most proximal portion of the everting balloon outer diameter 20 could be configured with a smaller outer diameter than the remainder of the everting balloon membrane 24. As an example, the first proximal portion of the everting balloon 18 can have a smaller balloon outer diameter 20 such as from about 2 mm to 4 mm for a length of from about 5 mm to about 10 mm from the distal terminal end of the outer catheter 4, and the remainder of the length (e.g., from about 4 cm to about 7 cm along the everting balloon 18) of the everting balloon 18 can have a balloon outer diameter 20 from about 4 mm to about 7 mm. The outer diameter of the proximal end of the everting balloon 18 can have a consistent balloon outer diameter 20, for example for delivery in the cervix or urethra, of from about 3 mm to about 6 mm, and the distal-most outer about 2 cm to about 3 cm of the everting balloon 18 can have a balloon outer diameter 20 from about 10 mm to about 20 mm, for example to create a seal with and anchor in the internal cervical os of the uterine cavity or the bladder.

The exterior surface of the balloon membrane 6 can be configured with ridges, projections, bumps, grooves, and additional surface or mechanical features, or combinations thereof, for example for increased friction or holding power within the vessel, or the entrapment of bodily fluids, cells, or tissue.

The everting balloon length 22 can be from about 2 cm to about 31 cm, more narrowly from about 2 cm to about 25 cm (e.g., for use in a male urethra), yet more narrowly from about 2 cm to about 12 cm for placement of IUDs, yet more narrowly from about 3 cm to about 6 cm for invitro fertilization, insemination procedures, or the delivery of instruments and endoscopes, for example about 4 cm, about 7 cm, about 15 cm and about 30 cm.

Figure 1E:
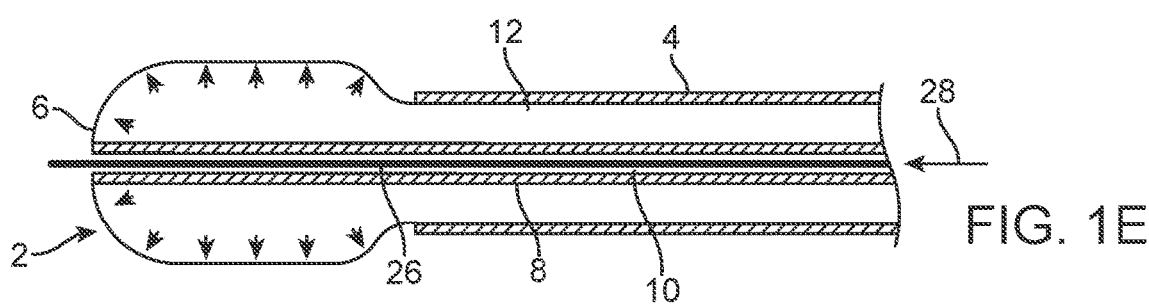

FIG. 1E illustrates that the everting catheter system can be in an inflated and partially or fully everted configuration. A device or tool 26, liquid, gas, or combinations thereof can be translated, as shown by the arrow 28, through the inner catheter lumen 10, out of the distal port of the inner catheter lumen 10 and into the target site. The tool 26 can be an IUD, a biopsy tool, a scope, a sonogram probe, a plug, a cauterization tool, or combinations thereof. Suction can be applied from the proximal end of the inner catheter lumen 10, and to the target site, for example removing debris from the target site through the inner catheter lumen 10.

To retract and reposition or remove the balloon membrane 6, the inner catheter 8 can be pulled proximally to pull the balloon membrane 6 back within the outer catheter 4. The balloon membrane 6 can be deflated or have media pressure 14 reduced and the entire system can be withdrawn from the target site.

Figure 2A:
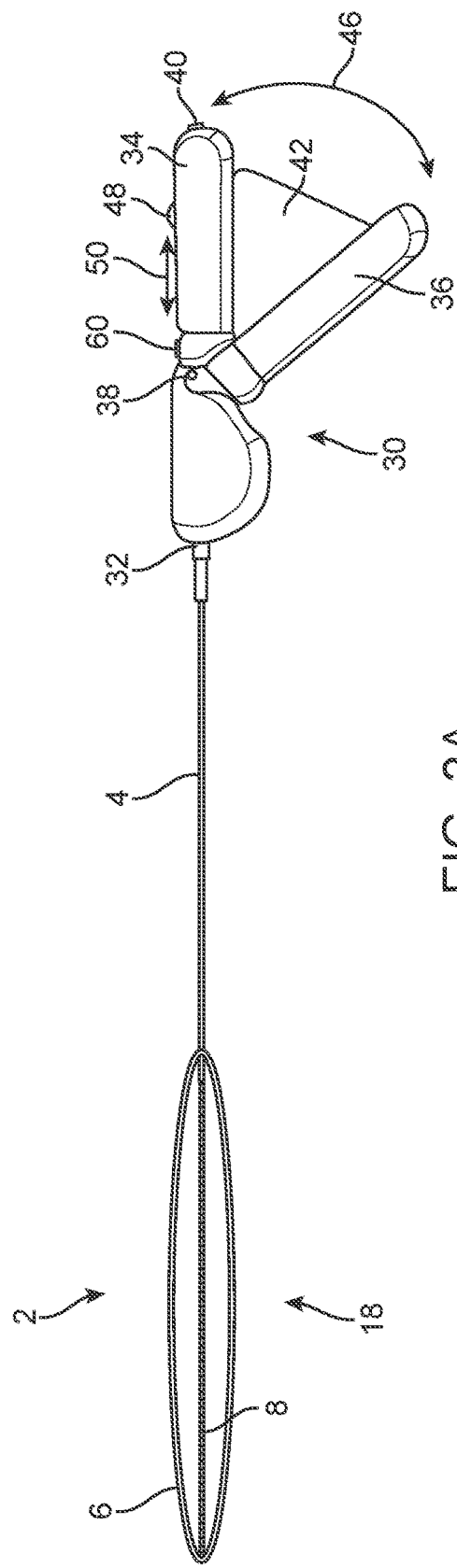
FIG. 2A illustrates a variation of the everting balloon system in a fully everted configuration.
Figure 2B:
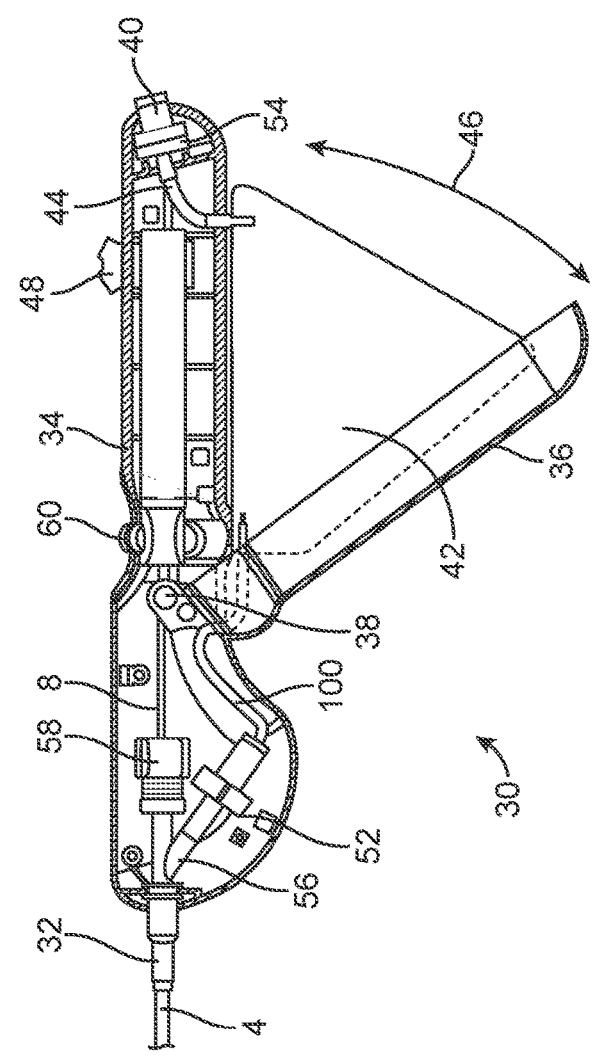
FIG. 2B is a cross-sectional view of a variation of the system handle.

FIG. 2 illustrates that the everting balloon system 2 can have a system handle 30. The system handle 30 can have a system handle connector 32. The system handle 30 can be attached to the outer catheter 4 and the inner catheter 8, for example at the system handle connector 32. The system handle connector 32 can be removably attached to the outer catheter 4. For example, the outer and inner catheters 4, 8 and balloons can be detached from the system handle 30 and replaced. The system handle 30 can be sterilizable. Media (e.g., liquid or gas) delivered by the system handle 30 can be filled into the system handle 30 before attaching or replacing the catheters and balloons.

The system handle 30 can have a rigid system handle case 34 and a rigid pump lever 36 rotatably attached to the system handle 30 case at a pump lever axle 38.

The system handle 30 can have an inlet port 40. The everting balloon system 2 can have a pressurization source. The pressurization source can have a flexible liquid reservoir 42 or fluid supply container or bag. The fluid bag can be filled with a hydraulic and/or pneumatic fluid.

The inlet port 40 can be a female luer fitting and connection. The inlet port 40 can be in fluid communication through an inlet-reservoir channel 44 with the flexible reservoir 42. The liquid reservoir 42 can be between the rigid pump lever 36 and a rigid system handle case 34. The inlet port 40 can extend out of the proximal end of the system handle case 34. The inlet port 40 can be configured to attach to a liquid source (e.g., a hose, tube, or supplemental reservoir configured to deliver the liquid through the inlet port 40 and to the liquid reservoir 42). The inlet port 40 can have a proximal check valve or one-way valve configured to allow flow to the liquid reservoir 42 and prevent backflow (e.g., proximal flow from the liquid reservoir 42 and out the inlet port 40).

The liquid reservoir 40 can be in one-way (e.g., via a check valve) or two-way fluid communication with the media volume 12.

When the liquid reservoir 42 contains liquid, the pump lever 36 can rotate away from the system handle case 34, as shown by pump lever rotation arrows 46, as the liquid reservoir 42 inflates. The pump lever 36 can be rotated toward the system handle case 34 to compress the liquid reservoir 42, for example, forcing liquid from the liquid reservoir 42 and into the media volume 12 of the everting balloon 18.

The pump lever 36 can provide a pumping (e.g., suction) action to supply aspiration to withdraw liquid from the media volume 12 of the everting balloon 18. A spring within the lever can facilitate the pumping action of the lever to open the lever (not shown) for each compression.

The system handle 30 can have an advancement slide 48. The advancement slide 48 can be proximally and distally translatable, as shown by arrow 50, with respect to the system handle case 34. The advancement slide 48 can be configured to translate the inner catheter 16 with respect to the outer catheter 4. For example, pushing the advancement slide 48 distally can push the inner catheter 8 distally with respect to the outer catheter 4 and evert the everting balloon 18. Pulling the advancement slide 48 proximally can pull the inner catheter 8 proximally with respect to the outer catheter 4 and retract the everting balloon 18. The advancement slide 48 can have gear wheels, ratchets with racks, and rotating advancement screws.

The advancement button can be an advancing ratchet or a roller wheel that is geared into or with the inner catheter 8 to allow for translation of the inner catheter 16.

With one hand, the physician can advance the inner catheter 8, evert the everting balloon 18, traverse the cervical canal with the everting balloon 18, and access the uterine catheter through the inner catheter lumen 10.

The fluid reservoir 42 can be pressurized prior to placement of the distal tip of the outer catheter 4 at the cervix. The fluid reservoir 42 can has a proximal check or one-way valve on the proximal portion of the handle. The proximal check valve is the connection point for the physician to pressurize the system. The distal portion of the fluid bag can be attached to a distal pressure check valve 52 that can open when pressure from the fluid bag is at or above a distal check valve limit pressure, for example about 1 atmosphere of pressure from the liquid reservoir, and then deliver liquid and pressure from the liquid reservoir 42 to fill and pressurize the media volume 12 of the catheters and everting balloon 18. The distal pressure check valve 52 can be a one-way valve allowing hydraulic or pneumatic fluid or media to go from the fluid reservoir 42 to the media volume 12 of the catheters and everting balloon 18. Higher and lower atmosphere pressure ratings from 1 atmosphere are also possible for the distal pressure check valve 52 such as from about 0.5 atmospheres to about 2 atmospheres.

During pressurization of the fluid reservoir 42 (e.g., by pumping with the pump lever 36 or from the inlet port via the proximal check valve 54), pressures greater than a reservoir limit pressure (e.g., 1 atmosphere) of the distal pressure check valve 52 can open the distal pressure check valve 52 and allow fluid media to flow from the liquid reservoir 42 into the media volume 12 of the catheters and everting balloon 18. The pressurization in the media volume 12 of the catheters and everting balloon 18 can unroll and evert the everting balloon 18 under hydraulic force. Excess media can remain in the fluid reservoir 42 after the everting balloon 18 fully everts.

The distal pressure valve 52 can be connected to a three-way connector 56 (e.g., Y-connector or T-connecter) that has a hemostasis valve 58, for example a Touhy-Borst valve. Thus the fluid reservoir 42 can stage or hold additional potential hydraulic pressure to be stored in the system for the user (e.g., physician) to use as needed by rotating the pump lever 46 without a change of hand position or the use of a second hand.

The inner catheter 8 can extend through the three-way connector 56. The inner catheter 8 can translate (i.e., advance and retract) through the three-way connector 56 while maintaining a seal (i.e., without the media volume 12 of the catheters or everting balloon 18 losing pressure). The inner catheter 8 (e.g., if a solid rod or mandrel) can be configured to withstand hydraulic pressures of up to about 5 atmospheres or up to about 10 atmospheres during the everting process and translational (e.g., advancement, retraction, tensile, compression, or combinations thereof) forces of up to about 2 pounds or up to about 5 pounds without deformation. As an example, during the everting process the inner catheter 8 with an inner catheter lumen 10 (e.g., a through lumen) could withstand media pressures 14, tensile and compressive forces, and rotational forces as the everting balloon membrane 6 traverses curved or tortuous anatomy, to allow for the passage of an instrument, catheter, media, or materials within the through lumen. Movement of the advancement button on the handle moves the inner catheter 8 within the three-way connector 56 and through the outer catheter 4. The everting balloon 18 can then evert and roll out of the outer catheter 4 and traverse the target site (e.g., the cervical canal).

After accessing the target site, for example, the user can activate the pressure release control 60 to release or reduce the pressure from the media volume 12 thereby deflating or reducing the outer diameter of the everting balloon 18, and/or manually withdraw the everting balloon 18 and inner catheter 8 by retracting the advancement slide 48 or pulling the system handle 30 proximally, and therefore the remainder of the system.

Once the biological lumen to be traversed (e.g., the cervical canal, or urethra) is traversed by the everted balloon 18, the everting balloon system 2 can increase the pressure in the everting balloon 18, for example increasing the diameter of the everting balloon 18, or while maintaining a constant diameter everting balloon 18 (e.g., for a fiber-reinforced everting balloon 18 or a balloon membrane 6 constructed from a less distensible material). The pump lever 36 can be compressed to increase pressure in the fluid reservoir 42 builds and exits the distal pressure check valve 52. The proximal check valve 54 can prevent or minimize the fluid media (e.g., pneumatic or hydraulic pressure) from leaking or bleeding in the proximal direction and out of the inlet port 40.

The user can rotate the pump lever 36, for example increasing the pressure in the fluid reservoir 42, the media volume 12, and the everting balloon 18. The balloon outer diameter can then increase, further pushing open the diameter of the biological lumen. For example, the everting balloon 18 can dilate the cervix and cervical canal. Tools such as endoscopes, instruments, Hegars, other devices to increase the diameter of the cervix further, or combinations thereof, can then be inserted into the dilated cervical canal concurrent with the everting balloon system 2 being located in the cervical canal or subsequent to the everting balloon system 2 being withdrawn from the cervical canal.

The pump lever 36 can deliver tactile feedback to the user indicating the pressure of the everting balloon 18. The everting balloon system 2 can have a pressure gauge indicating the pressure in the media volume 12, such as in the liquid reservoir 42 and/or the media volume 12 in the catheters and everting balloon 18.

The system handle 30 can have a pressure release control 60, such as a toggle lever or knob. The pressure release control 60 can release fluid from the liquid reservoir 42 and/or media volume 12 of the catheters and everting balloon 18.

The pressure release control 60 can be connected to the hemostasis valve 58. The hemostasis valve 58 can have a seal or sealing gasket. The pressure release control 60 can be configured to open and close the sealing gasket by rotating the sealing cap, or open a connection to a separate drainage tube (not shown) in fluid communication with the media volume 12.

The pressure release control 60 can be on the handle 30 positioned by the user's thumb position, distal to and collinear with the movement of the advancement slide 48. The pressure release control 60 can be operated by the same hand as the user is operating the advancement slide 48 and pump lever 36.

The pressure release control and handle can be used to advance and deliver an IUD with one hand by the user.

The user can perform the following operations of the everting balloon system 2 with a single hand (e.g., without their other hand or another operator) without a change of hand position:
  a. pressurize the liquid reservoir 42;
  b. position or place the distal end of the everting balloon system 2 at the patient's cervix;
  c. control the everting balloon system 2 position throughout use;
  d. advance the inner catheter 8 and balloon membrane 6;
  e. increase the diameter of the everting balloon 18 by pumping additional hydraulic pressure from the fluid reservoir 42;
  f. retract the inner catheter 8 and balloon membrane 6; and
  g. activate the pressure release control 60 to remove or release pressure from the everting catheter system.

Structurally, the buttons and actuators to enable these functions can be positioned on the handle to allow for the operator to manipulate these features without a change of hand position or requiring the use of the other hand. For instance, advancement and retraction of the inner catheter 8 can be performed by a slide mechanism or gear wheels that are located on the upper side of the handle approximately 4 inches from the proximal end of the handle or handle grip. Levers and ratchet mechanisms can be located on the lower or underneath side of the handle at a distance of from about 2 inches to about 4 inches from the proximal end of the handle grip. Additional actuators can be placed on the lateral sides of the handle grip from about 3 inches to about 4 inches from the proximal end of the handle grip or on the upper or lower portions of the handle grip from about 3 inches to about 4 inches from the proximal end. The button and actuator position can be palpable for the operator without requiring visual confirmation, thereby allowing the user to maintain eye contact with the patient or visualization source such as an endoscopic monitor or ultrasound image.

During the use of the everting balloon system 2, the user can utilize their other hand for handling an ultrasonic probe, a tenaculum (e.g., if the cervix is difficult to access by anatomical reasons or is severely retroverted or anteverted), stabilizing the patient or other instruments, or combinations thereof.

Figure 3A:
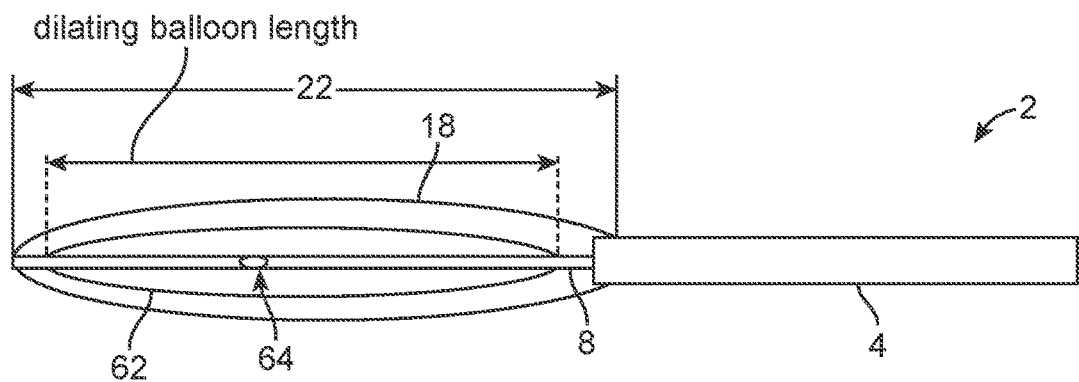
FIG. 3A illustrates a variation of the distal end of the everting balloon system with the dilating balloon in a less than fully inflated configuration.

FIG. 3A illustrates that the inner catheter 8 can be attached to a dilating balloon 62 or inner catheter balloon. The dilating balloon 62 can be radially inside of the everting balloon 18. The distal end and the proximal end of the dilating balloon 62 can be attached and sealed to the inner catheter 8. The inner catheter 8 can have a dilating balloon port 64 longitudinally within the dilating balloon 62. The dilating balloon port 64 can be in fluid communication with a fluid pressure source at the proximal end of the everting balloon system 2, for example in or attached to the system handle 30. The dilating balloon 62 can be inflated and deflated through the dilating balloon port 64.

The dilating balloon 62 can be more, the same, or less compliant than the everting balloon 18. The everting balloon 18 wall can be thicker, thinner, or the same thickness as the dilating balloon 62 wall. The everting balloon 18 can be made from one or more polymers including silicone, urethane, rubber, latex, polyethylene, polyolefin, irradiated polyolefin combined with ethylene vinyl acetate, co-polymers such as polyether block amide (PEBA, also known as Pebax), a fiber-reinforced polymer, PET, nylon, or combinations thereof. The dilating catheter can be made from any of the materials mentioned for the everting balloon 18.

The everting and/or dilating balloon membrane 6 can have a thickness from about 0.001 in to about 0.004 in.

The everting and/or dilating balloon 18, 62 can be internally coated with a lubricious material such as silicone oil, mineral oil, other lubricant, or combinations thereof. The lubricous coating can reduce the friction within the balloon during eversion.

The exterior of the everting and/or dilating balloon 18, 62 can be smooth, for example the balloon can be made by tubing extrusion. The balloons can be blow molded. For example, the exterior surface of the balloon can have ridges or other surface protrusions, for example to increase friction or holding forces in the target body lumen (e.g., cervical channel or urethra). The outer diameter of the balloons can vary dimensionally. For instance, the most distal portion of the everting balloon 18 can be manufactured with a larger outer diameter to accommodate larger vessel sizes or inflation that can extend into the bladder.

During use, the everting balloon 18 can pull the inner catheter 8 into the endocervical canal. When the everting balloon 18 is deployed into the cervical channel, the dilating balloon 62 can be positioned in the cervical channel.

Figure 3B:
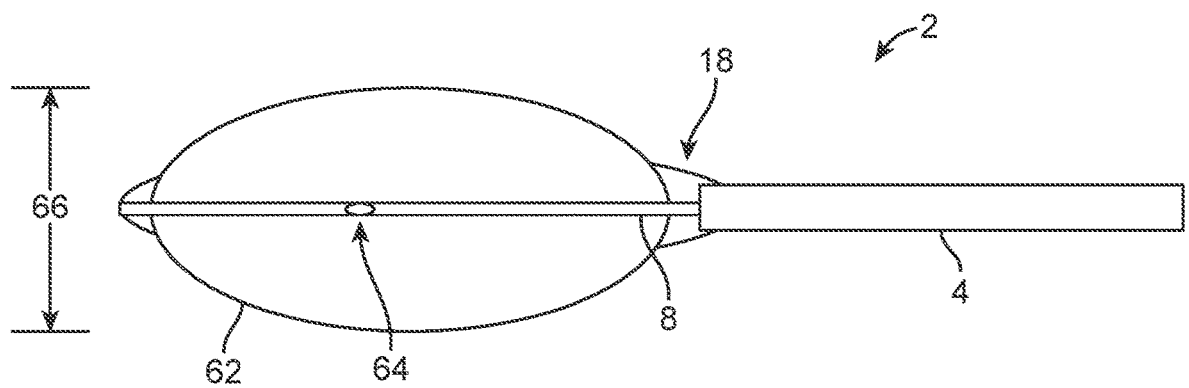
FIG. 3B illustrates a variation of the distal end of the everting balloon system with the dilating balloon in a fully inflated configuration.

FIG. 3B illustrates that the dilating balloon 62 can be inflated by delivering pressurized fluid through the dilating balloon inflation port 64. The dilating balloon 62 can expand inside of the everting balloon 18. The dilating balloon 62 can inflate to a dilating balloon diameter 66.

The dilating balloon 62 can have a predetermined or molded size and shape. For example, the dilating balloon 62 can have a dilating balloon diameter 66. For example, the maximum dilating balloon diameter 66 or maximum everting balloon diameter can be from about 2 mm to about 12 30 mm, and for some applications, up to about 20 mm in diameter (e.g., for use in a cervix), and more narrowly from about 2 mm to about 10 mm (e.g., for use in a urethra), more narrowly from about 6 mm to about 12 mm, yet more narrowly from about 2 mm to about 7 mm (e.g., for use in a urethra), yet more narrowly from about 3 mm to about 4 mm (e.g., for use in a male urethra). The dilating balloon 62 can inflate to a preset outer diameter. (The dilating balloon outer diameter 66 can be equal to or less than the dilating diameter needed for the body lumen, such as the cervix.) The everting balloon 18 can have a maximum everting balloon diameter equal to or less than the maximum dilating balloon diameter 66.

The dilating balloon 62 can be inflated to the same or a higher pressure than the everting balloon 18. For example, the dilating balloon 62 can have a dilating balloon pressure from about 4 atmospheres to about 12 atmospheres of pressure, and up to about 20 atmospheres of pressure, for example for disrupting a pathological stenosis or condition within a bodily lumen.

When the dilating balloon 62 is inflated, the everting balloon 18 can stretch due to the expanding dilating balloon 62 to the dilating balloon diameter 66. The inflation media within the everting balloon 18 can remain inside the balloon or be withdrawn before, during, and/or after inflation of the dilating balloon 62. Due to the frictional forces of the everting balloon membrane 6 on the bodily lumen in the everted state, for example, the everting balloon membrane 6 can serve to maintain the position of the dilating balloon 62 during the dilation process without unintentional advancement or retraction of the system within the bodily lumen during the dilatation process.

The dilating balloon 62 can inflate and tear or break the everting balloon 18 as the everting balloon diameter expands beyond the strain limit for the everting balloon 18. The inflation media within the everting balloon 18 can remain inside the balloon or be withdrawn before, during, and/or after inflation of the dilating balloon 62, for example exiting the everting balloon 18 can exit when the everting balloon 18 tears open.

The everting balloon 18 can break or tear along an intentional line upon the inflation of the dilating catheter. For example, the everting balloon 18 can be torn by a mechanical instrument on or within the outer catheter 4, a sharp implement on the proximal portion of the inner catheter 8 that becomes active upon full eversion and inflation of the dilating balloon 62, and/or further advancement of the inner catheter 8 that disengages the attachment or bond between the everting balloon 18 and the inner catheter 8 on the distal end of the inner catheter 8. The tearing or splitting of the everting balloon 18 can be done be weakening the everting balloon 18 with a mechanical indentation or seam on the balloon membrane 6 that splits upon reaching a specific strain limit, such as along a helical line, lateral line, longitudinal line, or combinations thereof. The everting balloon membrane 24 can be manufactured with increased longitudinal axial orientation of the molecular structure by tensioning or expanding the membrane along the longitudinal axis of the balloon during the balloon forming process which can promote a longitudinal break if the everting balloon membrane 24 splits or tears. A radial tear in the everting balloon 18 can be promoted by manufacturing the balloon membrane 6 with greater radial orientation of the molecular structure by radially expanding or tensioning the balloon membrane 6 during the balloon forming process.

The system handle 30 can hold the inflation media to be delivered to and from the everting balloon 18 and the dilating balloon 62. The inflation media can be in the liquid reservoir 42 (e.g., the fluid bag or a syringe piston). The inflation media can be delivered, for example via valves, to the dilation balloon after the inflation and eversion of the everting balloon 18. The system handle 30 can have gear wheels or a ratchet configured to advance the inner catheter 8. The outer catheter 4 can extend about 25 cm distal to the system handle 30. The system handle 30 and actuators can inflate the everting balloon 18 and dilating balloon 62 from control with one hand.

The dilating balloon 62 can be positioned into and dilate the cervix.

Figure 4A:
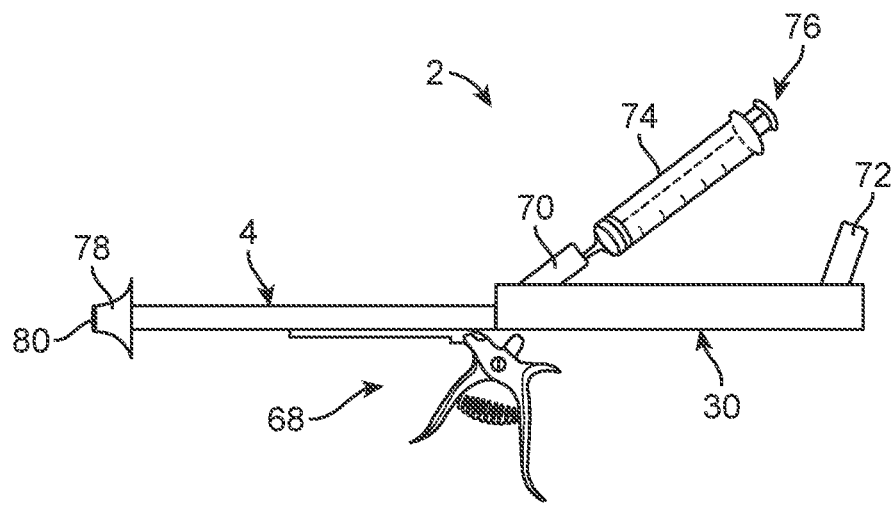
FIG. 4A illustrates a variation of the everting balloon system with a syringe in an attached, but not yet deployable configuration.
Figure 4B:
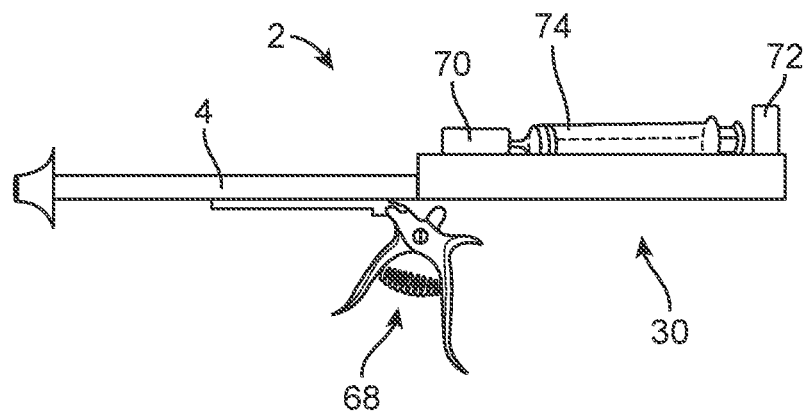
FIG. 4B illustrates a variation of the everting balloon system with the syringe in an attached and deployable configuration.
Figure 4C:
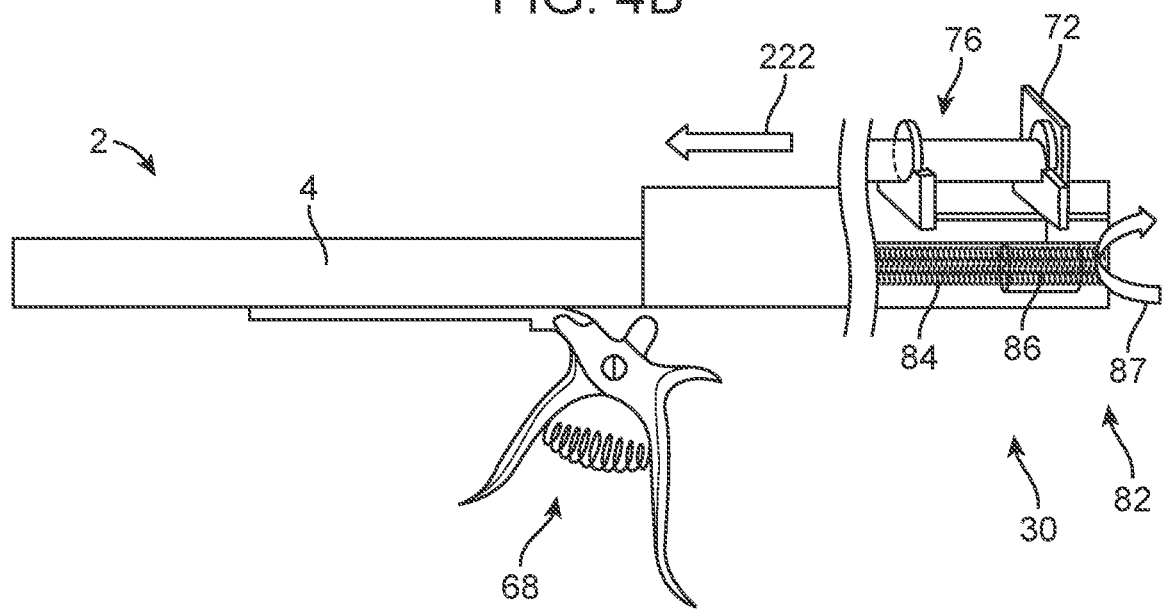
FIG. 4C illustrates a variation of the everting balloon system of FIG. 4B with the plunger driver shown in cutaway.

FIGS. 4A through 4C illustrate that the inner catheter 8 can be in a fully retracted position inside of the outer catheter 4.

FIG. 4A illustrates that the system handle 30 can have a pump lever 36, such as a ratchet handle 68, a syringe connector 70, and a plunger drive plate 72. The ratchet handle 68 can have a finger grip, trigger, lever, pump mechanism, or combinations thereof. The fluid reservoir can be a syringe 74. The syringe 74 can have a volume from about 5 cc to about 20 cc, for example about 5 cc or about 20 cc. An open distal port of the syringe can be attached to and in fluid communication with the syringe connector 70. The syringe connector 70 can have the distal pressure valve 52. The syringe connector 70 can be rotatably attached to the system handle case 34. The syringe 74 can have a plunger 76 longitudinally translatable with the remainder of the syringe 74. The syringe 74 can be filled with any media disclosed herein, such as saline, air, gas, or combinations thereof. The liquid reservoir 42 can have two separate syringes 74, each attached to and in fluid communication with the same or different syringe connectors 70. For example, a first syringe can be in fluid communication with the everting balloon 18, and the second syringe can be in fluid communication with the dilation balloon 62.

The syringe 74 can be locked to the syringe connector 70.

The outer catheter 4 can have an outer catheter distal tip 78. The outer catheter distal tip 78 can be, for example, an atraumatic tip such as an acorn tip or stop. The outer catheter distal tip 78 can be configured to prevent insertion of the outer catheter 4 too far into the target biological lumen (e.g., the endocervix).

The outer catheter distal tip 78 can have an outer catheter distal port 80. The outer catheter distal port 80 can be large enough to allow the inner catheter 8 and balloons to pass through.

FIG. 4B illustrates that the syringe connector 70 and syringe 74 can rotate, as shown by the arrow, so the longitudinal axis of the syringe 74 can be parallel or collinear with the longitudinal axis of the outer catheter 4. The syringe connector 70 can be angularly fixed with respect to the rest of the system handle 30. The plunger drive plate 72 can be rotated and/or translated to contact or almost contact the proximal end of the syringe plunger 76.

FIG. 4C illustrates that the system handle 30 can have a plunger driver 82. The plunger driver 82 can have a linear rack or plunger drive screw 84, plunger drive collar 86, and plunger drive plate 72. The ratchet handle 68 can be squeezed to rotate the plunger drive screw 84, as shown by arrow 87, or linear rack. The plunger drive screw 84 or linear rack can be configured to translate the plunger drive collar 86. For example, the plunger drive collar 86 can have internal threads engaging with outer threads of the plunger drive screw 84. The plunger drive collar 86 can be translatably fixed to the plunger drive plate 72. The plunger drive collar 86 and plunger drive plate 72 can translate distally with respect to the remainder of the syringe 74 when the ratchet handle 68 is squeezed. The plunger drive plate 72 can be in contact with and press the plunger 76 in a distal direction as shown by arrow.

The ratchet handle 68 can have a ratchet to prevent reversing the direction of the plunger driver, for example to prevent proximal translation of the plunger 76. A release lever can be rotated or deployed to release the ratchet mechanism for disengagement of the assembly, withdrawal of the system, or redeployment. The ratchet handle 68 can have no ratchet or a two-way ratchet, for example controlling the direction of the plunger driver 82, for example to allow proximal and distal translation of the plunger 76. The plunger drive plate 72 can be fixed to or touching but unfixed to the plunger 76.

Squeezing the ratchet handle 68 can depress the syringe plunger 94. Depressing the syringe plunger 94 can force inflation media from the syringe 74 to the media volume 12 of the dilation and/or everting catheter 18, for example pressurizing the respective balloons.

FIGS. 5A through 5F illustrates that the system handle 30 can have a stop cock and check valve 88 extending from the three-way connector 56. The stop cock and check valve 88 can be in fluid communication with the media volume 12. The stop cock and check valve 88 can be outside (as shown) or inside of the system handle case 34. The stop cock and check valve 88 can be accessed to add media, remove media, or check the pressure of the media in the media volume 12.

The system handle 30 can have one or more syringe detents 90. The syringe detents 90 can removably attach to a portion of the syringe 74 to prevent or minimize longitudinal translation of the syringe 74 with respect to the system handle case 34. The syringe detent 90 can be configured to allow the syringe 74 to slide in and out of the detent transverse to the longitudinal axis of the syringe 74.

The system [[case]] handle case 34 can have a deflecting plate 92. The outer and/or inner catheters 4, 8 can press against the deflecting plate 92. The deflecting plate 92 can alter or deflect the path of the outer and inner catheters 4, 8 towards the longitudinally axial direction of the target site. The deflecting plate 92 can have a molded or formed groove, pins, plate, panel, or combinations thereof. The outer catheter 4 can be manufactured with a preset curve to accommodate the curved path within the system handle case 34.

The system handle case 34 can have a handle grip 96. The inner catheter 8 can have a linear inner catheter grip length 98. The inner catheter grip length 98 can be a length of the inner catheter 8 in the uneverted state in the handle grip 96. The inner catheter grip length 98 can be about 12 cm of inner catheter 8 in the uneverted state, for example corresponding to an eversion length for the inner catheter grip length 98 of about 6 cm (e.g., about 50% of the inner catheter grip length 98) of everted balloon membrane 24. Alternatively, the inner catheter 8 can be configured to coil up on wheel, have telescoping segments, or have folding and unfolding segments, to reduce the amount of distance needed within a system handle case 34 to accommodate the length of inner catheter 8 in the uneverted state.

The system handle 30 can have a reservoir-catheter channel 100, for example in fluid communication with the distal end of the syringe 74 and the proximal end of the inner catheter 8. The reservoir-catheter channel 100 can be a tube from the syringe connector 70 to the inner catheter 8.

The system handle 30 can have an access channel 102 extending from an external surface of the system handle connector 32 to an external surface of the system handle case 34. The access channel 102 can proximally terminate at a proximal access port 104.

The inner catheter 8 can extend through the access channel 102. One or more tools or fluids can be inserted through, and/or suction can be applied to, the proximal access port 104 and access channel 102 into and through or adjacent to the inner catheter 8.

The system handle 30 can have one or more drive gears 106. The drive gears 106 can be on one or opposite sides of the access channel 102. The drive gears 106 can encroach or impinge into the access channel 102. The drive gears 106 can be rotatably attached to the system handle case 34 via drive gear axles 108. The drive gears 106 can have teethed gear sections and drive gear grooves 124. The inner catheter 8 can extend through the drive gear grooves 124. The drive gears 106 can frictionally push and pull the inner catheter 8. One or more of the drive gears 106 can extend and be exposed out of the system handle case 34. For example, the exposed drive gears 106 can be rotated by pressing on the exposed drive gear 106 with the user's palm or digit (e.g., thumb). The exposed drive gear 106 can be interdigitally engaged with one or more non-exposed drive gears 106. Rotating a first one of the drive gears 106 can rotate other drive gears 106 interdigitally engaged with the first drive gear 106.

The system handle case 34 can have a system handle case first lateral portion 110 and a system handle case second lateral portion 112. The system handle 30 can be made by attaching the system handle case first lateral portion 110 to the system handle case second lateral portion 112. Each drive gear axle 108 can be rotatably attached to the system handle case first lateral portion 110 and the system handle case second lateral portion 112.

The pump lever axle can be a ratchet handle axle 114. The ratchet handle 68 can rotate around the ratchet handle axle 114.

The system handle 30 can have a plunger drive rack 116. The plunger drive rack 116 can be fixed to the plunger drive plate 72. The plunger drive plate 72 can extend perpendicularly from the proximal end of the plunger drive rack 116. A side of the plunger drive rack 116 facing toward the plunger drive plate 72 can have unidirectional or bidirectional drive teeth 118.

The system handle 30 can have a ratchet handle spring 120 compressed between the system handle case 34, and/or the ratchet handle 68, and/or a ratchet arm 122. The ratchet handle spring 122 can reset the ratchet handle 68, for example by rotating the ratchet handle 68 forward, after the ratchet handle 68 has been squeezed.

The system handle 30 can have the ratchet arm 122 or actuating pawl. The ratchet arm 122 can be mechanically attached to the ratchet handle 68, for example to the handle spring 120. The ratchet arm 122 can be in a track limiting motion of the ratchet arm 122 to translation in the longitudinal direction with respect to the syringe 74. The proximal terminal end of the ratchet arm 122 can be curved in a u-shape. The terminal end of the ratchet arm 122 can press against a ratchet tooth. The ratchet arm 122 can be configured to pull the plunger drive rack 116 distally when the ratchet handle 68 is squeezed. The ratchet arm 122 is configured to move proximally with respect to the plunger drive rack 116 when the ratchet handle 68 is returned to a reset position.

The system handle 30 can have a locking pawl (not shown) can be spring-loaded between the system handle case 34 and the plunger drive rack 116, for example, allowing distal translation of the plunger drive rack 116 and preventing proximal translation of the plunger drive rack 116 except when the locking pawl is manually released from the plunger drive rack 116 by the release lever 126.

Figure 5A:
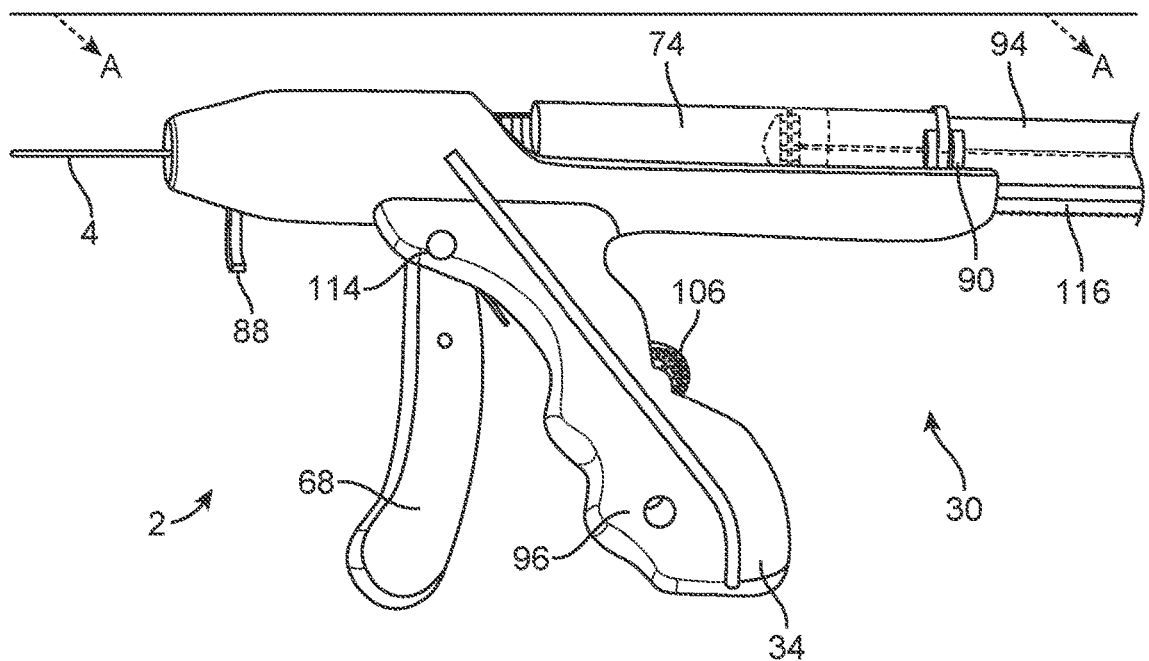
FIG. 5A illustrates a length of a variation of the everting balloon system.
Figure 5B:
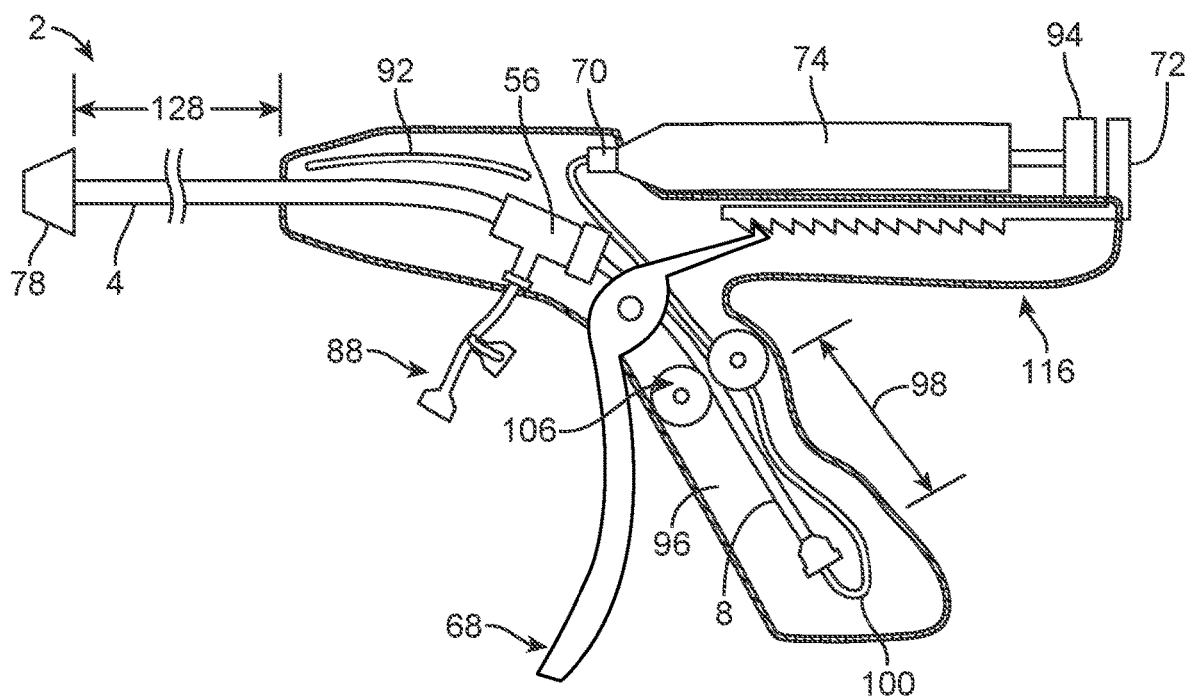
FIG. 5B is a partial cross-sectional view of a variation of the system of FIG. 5A.
Figure 5C:
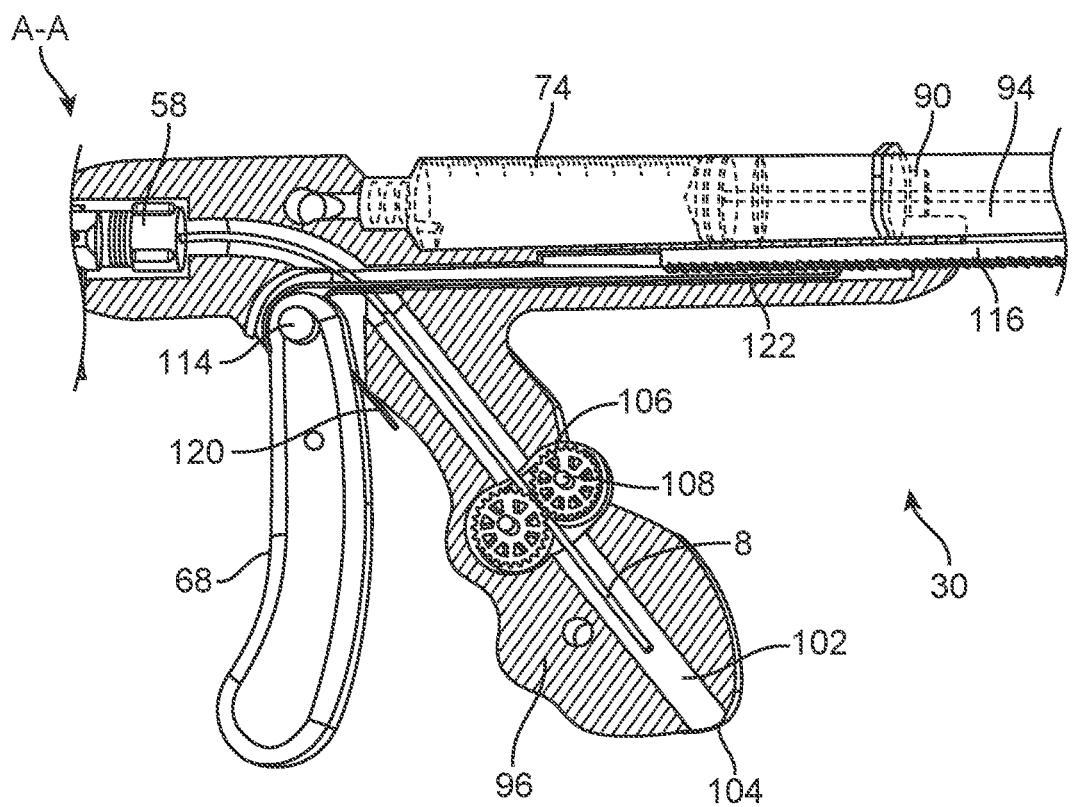
FIGS. 5C and 5D are variations of side and perspective views of a portion of cross-section A-A.
Figure 5D:
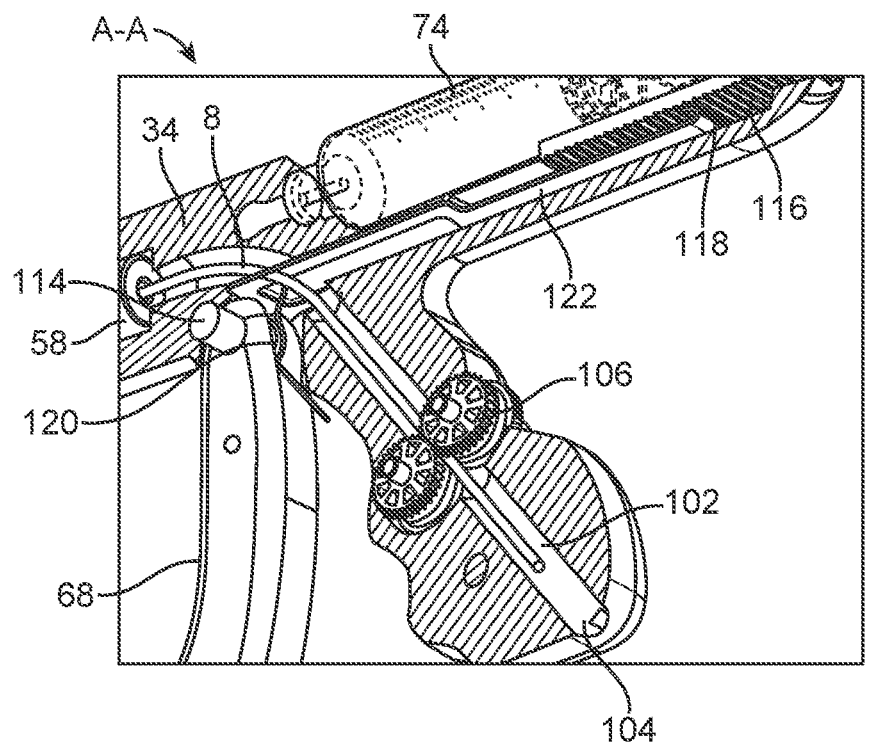
Figure 5E:
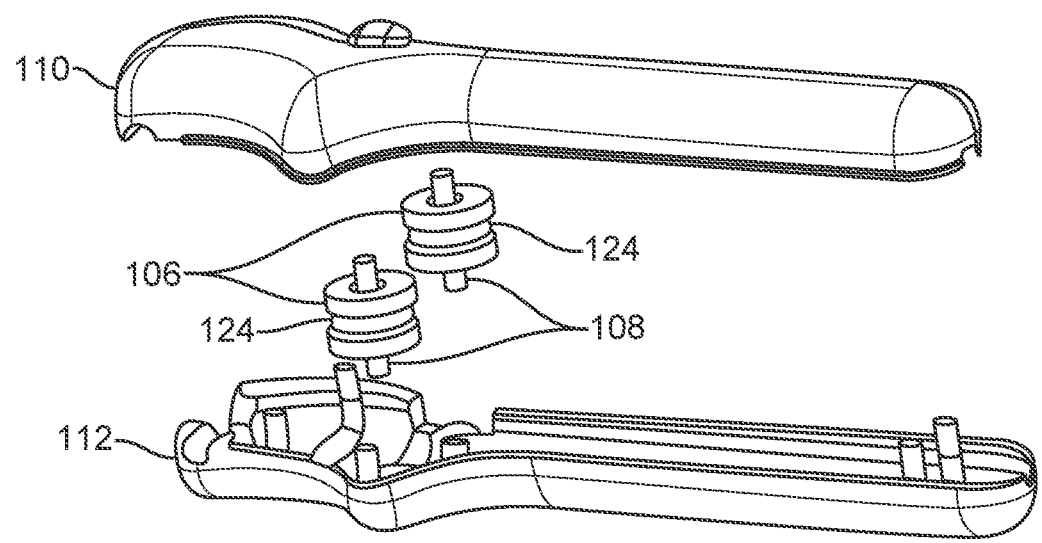
FIG. 5E is an exploded view of a variation of a portion of the system handle and the drive gears.
Figure 5F:
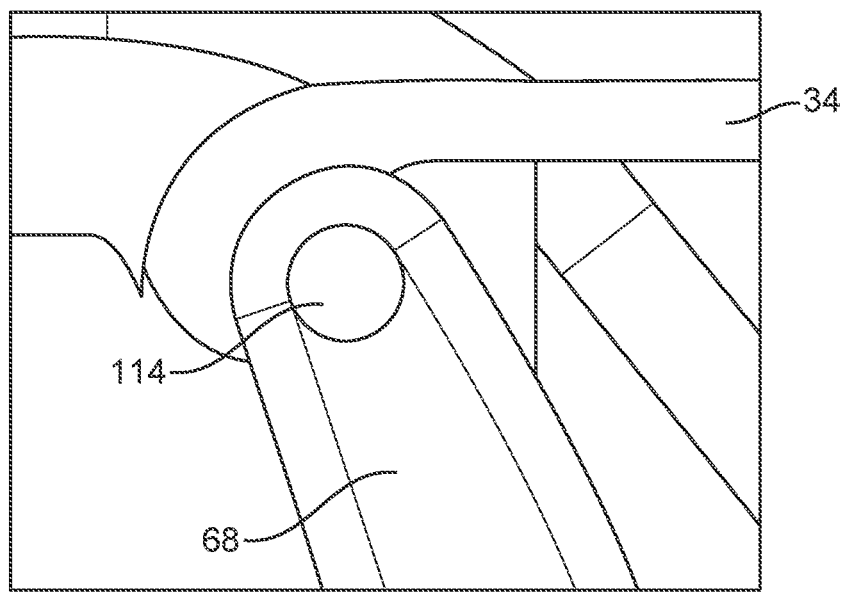
FIG. 5F is a close-up view of a variation of the system handle at the ratchet handle axle.

The outer catheter 4 can have an outer catheter length 128, as shown in FIG. 5B. The outer catheter length 128 can be from about 4 cm to about 35 cm, more narrowly from about 10 cm to about 24 cm, for example about 17 cm.

FIGS. 6A through 6D illustrate that the system handle 30 can have an inner catheter drive tray 130 translatably attached to the system handle case 34. A proximal length of the inner catheter 8 can extend proximally from the system handle case 34. The proximal length of the inner catheter 8 can be in, on, or adjacent to the inner catheter drive tray 130.

The syringe 74 can have a syringe loading connector 132, such as a luer connector, at the terminal distal or proximal end of the syringe 74 (e.g., the end further from the system handle case 34). A delivery tube 133 or delivery device can be attached to the syringe loading connector 132 and pressurized media can be delivered through the syringe loading connector 132 into the syringe 74.

Figure 6A:
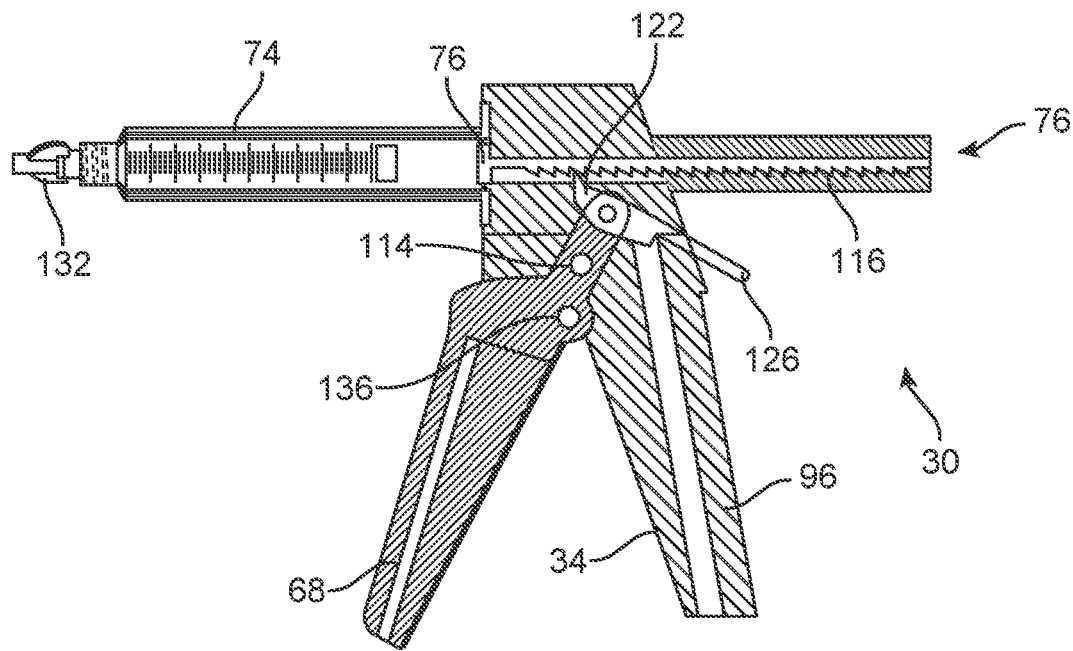
FIG. 6A is a cross-sectional view of a variation of the system handle.
Figure 6B:
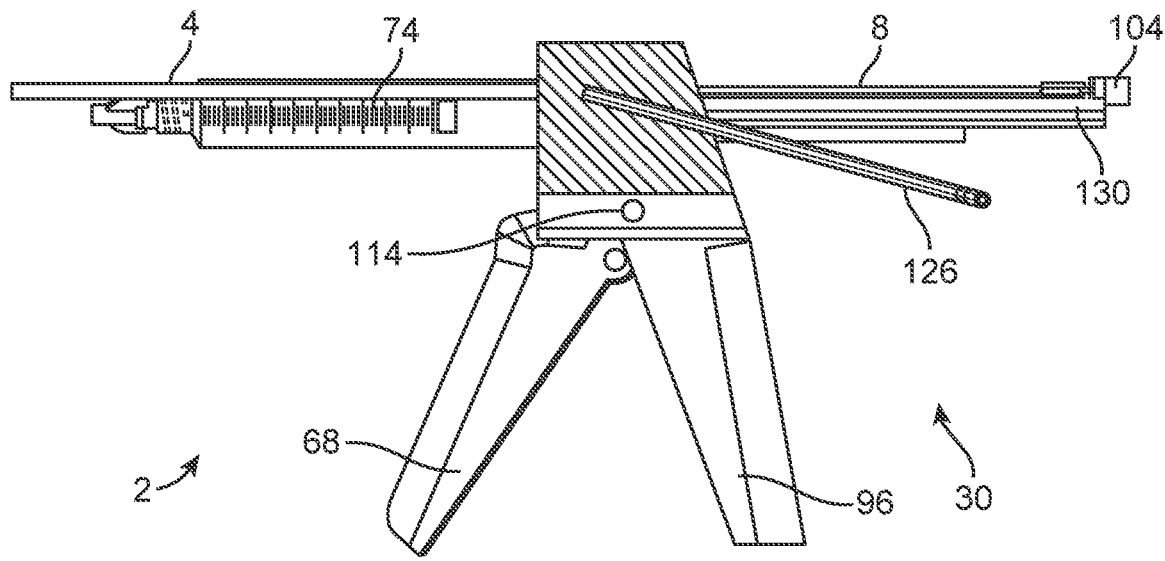
FIGS. 6B through 6D are side, top perspective and cross-sectional views, respectively, of a variation of the everting balloon system with the system handle of FIG. 6A.
Figure 6C:
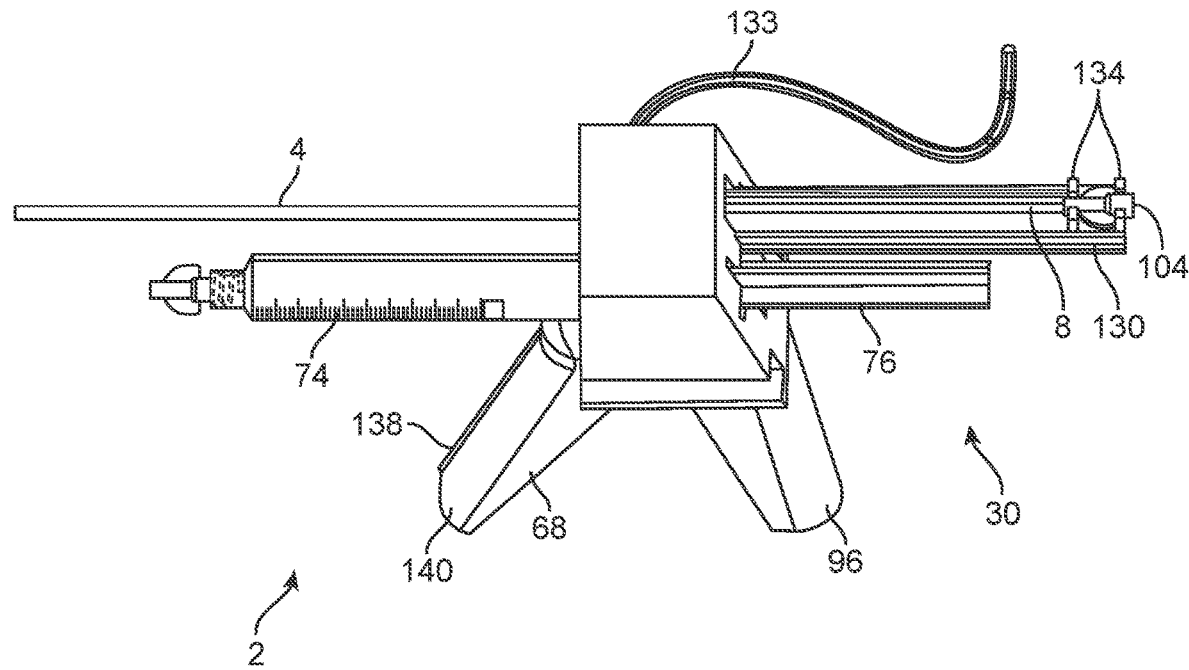

The delivery tube 133 or delivery device can be disconnected from the syringe loading connector 132 before deploying the everting balloon 18, as shown in FIG. 6C. The delivery tube 133 can wrap inside the handle grip 96 and connect the syringe 74 and its pressurization media to the three-way connector 56 and the hemostasis valve 58 or inlet port 40 for the dilation balloon 62.

The proximal terminal end of the inner catheter 8 can be attached to the proximal access port 104. The proximal end of the inner catheter drive tray 130 can have one or more access port detents 134. The access port detents 134 can attach to the proximal access port 104. The access port detents 134 can removably attach to a portion of the proximal access port 104 to prevent or minimize longitudinal translation of the proximal access port 104 with respect to the inner catheter drive tray 130. The access port detent 134 can be configured to allow the proximal access port 104 to slide in and out of the access port detents 134 transverse to the longitudinal axis of the inner catheter drive tray 130.

The inner catheter drive tray 130 can be translated along the longitudinal axis of the inner catheter drive tray 130 to translate the inner catheter 8 (e.g., advance the inner catheter 8 into the target site). The inner catheter can deliver an IUD, instrument, device, endoscope, or a dilating balloon.

The system handle case 34 can have a fluid connection between the syringe 74 and the outer catheter 4, as disclosed herein.

Figure 6D:
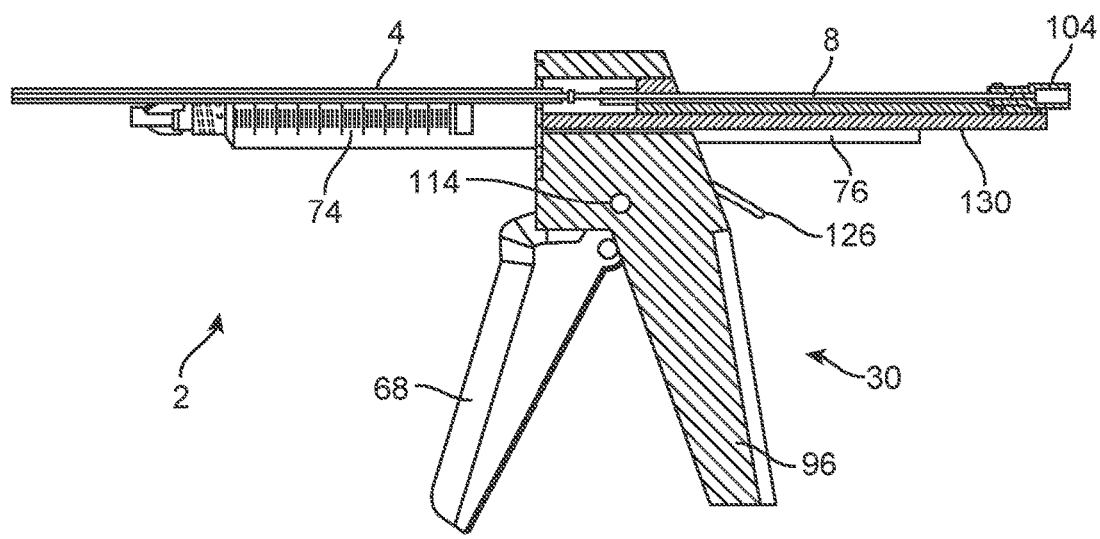

The ratchet arm 122 can extend away from the drive rack 116 to form a release lever 126, as shown in FIG. 6A. One or more other release levers 126 can extend from other locations on the system handle 30, as shown in FIGS. 6B and 6D. The release lever 126 can be rotated to disengage the ratchet arm 122 from the drive rack 116.

The ratchet handle 68 can have a safety lock hole 136. A safety lock having a cable or rod can removably extend through the safety lock hole 136, for example to create an interference fit against the system handle case 34 and prevent rotation of the ratchet handle 68, for example preventing unintentional or premature media delivery from the syringe 74.

The ratchet handle 68 can be laterally split into a catheter sub-handle 138 and a media sub-handle 140. The catheter sub-handle 138 can be configured to control the advancement of the inner catheter drive tray 130. The media sub-handle 140 can be configured to control the pressure of media delivery from the syringe 74. The catheter sub-handle 138 can be attached to an inner catheter drive rack. The media sub-handle can be attached to a plunger drive rack.

The ratchet handle 68 can control the syringe 74 for applying media pressure to the everting balloon 18 and dilating balloon 62, and independently control the translational movement of the inner catheter 8.

Figure 7A:
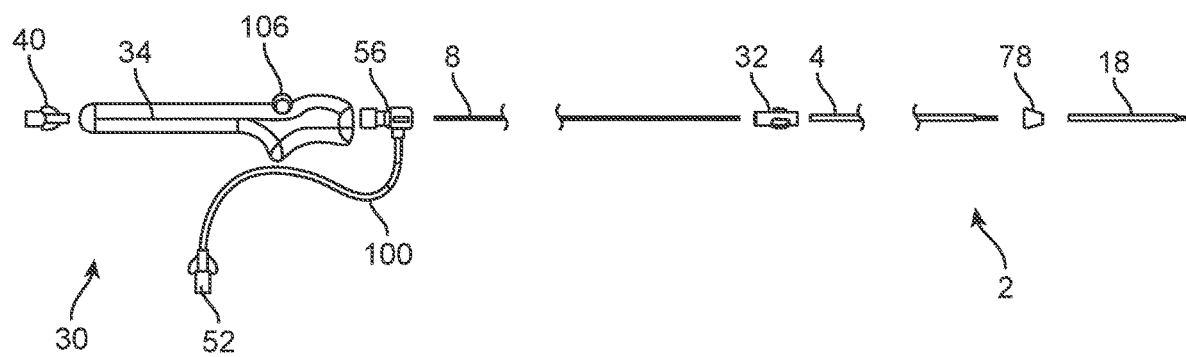
FIGS. 7A and 7B are exploded and perspective views, respectively, of a variation of the everting balloon system.
Figure 7B:
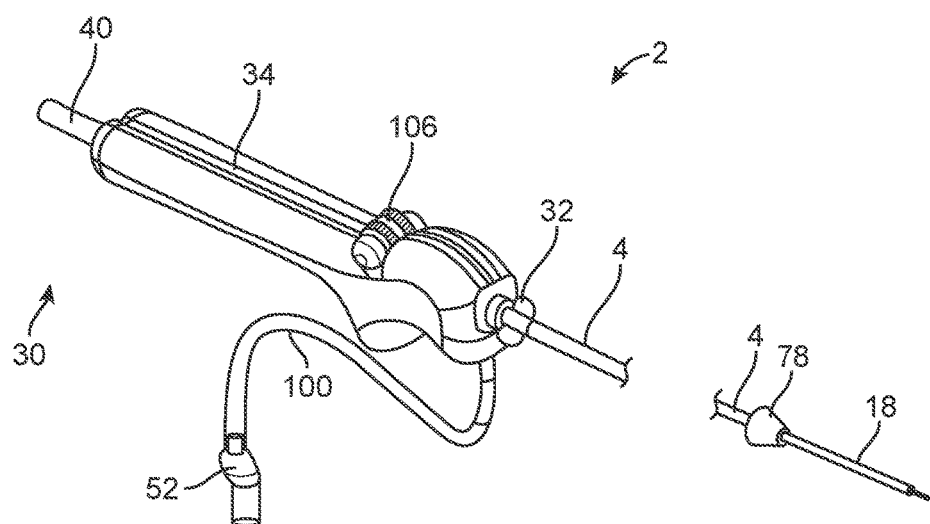

FIGS. 7A and 7B illustrate that the inlet port 40 can have a female luer connector. The system handle connector 32 can have a female luer connector. The outer catheter distal tip 78 can have a soft rubber or polymerized acorn tip, for example, to assist in stabilizing the everting system 2 at the opening of the bodily lumen or preventing unintentional advancement of the outer catheter 4 within the bodily lumen.

The reservoir-catheter channel 100 can extend from the three-way connector 56 and out of the system handle case 34. The proximal terminal end of the reservoir-catheter channel 100 can be attached to a female luer connector and/or the distal pressure valve 52. The distal pressure valve 52 and/or female luer connector can be connected to the liquid reservoir 42 (not shown).

Figure 8A:
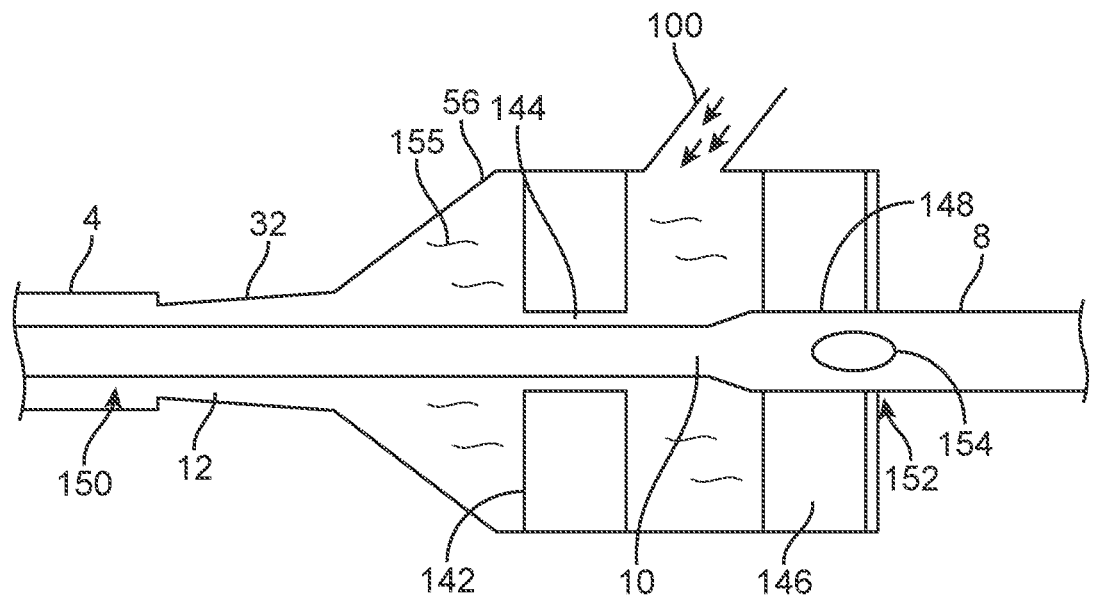
FIG. 8A is a cross-section view of a variation of the three-way connector and adjacent elements in a configuration to deliver media pressure to the outer catheter, for example to the everting balloon.

FIG. 8A illustrates that the three-way connector 56 can have a hemostasis valve 58. The three-way connector 56 can have or be a Touhy-Borst Y-connector. The inner catheter 8 can extend through the three-way connector 56.

The three-way connector 56 can have a distal gasket 142 between the reservoir-catheter channel 100 and the system handle connector 32. The distal gasket 142 can have a cylindrical distal gasket port 144 extending through the radial middle of the distal gasket 142. The distal gasket port 144 can have a distal gasket port diameter.

The three-way connector 56 can have a proximal gasket 146 proximal to the distal gasket 142. The proximal gasket 146 can be between the reservoir-catheter channel 100 and the proximal outlet through which the inner catheter 8 proximally exits the three-way connector 56. The proximal gasket 146 can be more, the same, or less compliant than the distal gasket 142. The proximal gasket 146 can have a cylindrical proximal gasket port 148 extending through the radial middle of the proximal gasket 146. The proximal gasket 146 can have a proximal gasket port diameter.

The inner catheter 8 can have an inner catheter small diameter length 150 and an inner catheter large diameter length 152 proximal to the inner catheter small diameter length 150. The inner catheter 8 can have an inner catheter proximal inflation hole 154 at the distal end of the inner catheter large diameter length 152. The inner catheter proximal inflation hole 154 can be in fluid communication with the open distal end of the inner catheter lumen 10 and/or the dilating balloon port 64.

Positive media pressure 14 or flow can be delivered, as shown by arrows, through the reservoir catheter channel 100 to the three-way connector 56. The inner catheter large diameter length 152 can occlude, plug, and/or seal the proximal gasket port 148. The positive media pressure 14 or flow can be delivered through the gap between the outer diameter of the inner catheter 8 (e.g., along the inner catheter small diameter length 150) and the inner diameter of the distal gasket port 144 and to the media volume 12 between the outer catheter 4 and the inner catheter 8, for example to the everting balloon 18.

Figure 8B:
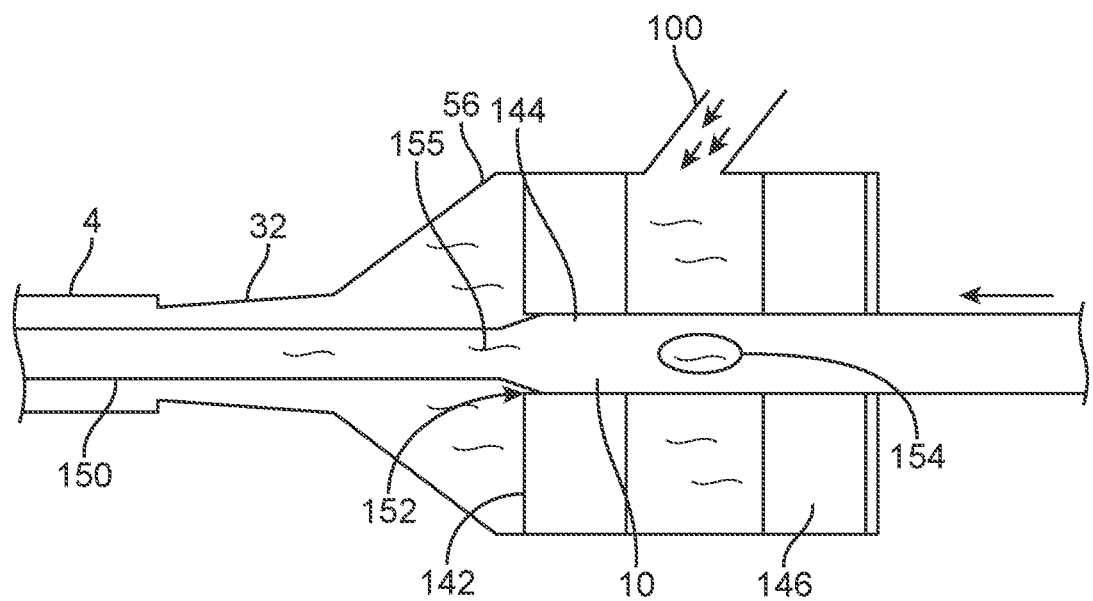
FIG. 8B is a cross-section view of a variation of the three-way connector and adjacent elements in a configuration to deliver media pressure to the inner catheter, for example to the dilating balloon.

FIG. 8B illustrates that the inner catheter 8 can be translated distally, as shown by arrow, at least until the inner catheter large diameter length 152 moves into the distal gasket port 144. The inner catheter large diameter length 152 can slide through the proximal gasket port 148. The inner catheter large diameter length 152 can occlude, plug, and/or seal the distal gasket port 144 and/or against the distal gasket 142. The media 155 flow from the reservoir-catheter channel 100 can be forced to flow into the inner catheter proximal inflation hole 154. The media 155 can flow down the inner catheter lumen 10, for example to the dilating balloon 62.

An exemplary procedure for delivering an IUD (not shown) or dilating a body lumen such as the cervical canal can include:

1. The syringe 74 can be loaded onto the system handle 30. The system handle 30 can be a separate, reusable item in which the everting catheter and syringe filled with media 155 can be attached to the remainder of the system before use. Alternatively, the system handle 30 can come supplied to the end user preassembled with the remainder of the system and pre-filled, or combinations thereof.
2. The distal end of the everting balloon system 2 can be placed at the exocervix.
3. The ratchet handle 68 can be depressed. The first one to two clicks of the ratchet (i.e., as the locking pawl passes over ratchet teeth) can depress the syringe plunger 94 and pressurize the everting balloon 18. The everting balloon 18 can be pressurized to 4 to 6 atmospheres.
4. The ratchet handle 68 can be depressed further (or released to rotationally reset and then depressed further). The next sets of clicks on the ratchet handle 68 can indicate advancement the inner catheter 8. This can be accomplished by the ratchet mechanism rotating gear wheels on the inner catheter 8 and/or translating a linear rack to advance the inner catheter 8.
5. The ratchet handle can be depressed further (or released to rotationally reset and then depressed further). The advancement of the inner catheter 8 can continue until the everting balloon is fully deployed and everted. The dilation balloon 62 can be positioned on the distal end of the inner catheter 8.
6. The ratchet handle 68 can be depressed further. The next click of the ratchet can de-pressurize the everting balloon 18 or deliver an IUD (not shown).
7. The ratchet handle 68 can be depressed further. The next click of the ratchet can change the pressurization outlet of the syringe 74 from the everting balloon 18 to the dilation balloon 62 or this action can deliver an IUD (not shown). This can be accomplished, for example, by:
   a. rotating a valve with the ratchet mechanism,
   b. manually rotating the valve, and/or
   c. advancing the inner catheter 8 to where the inner catheter proximal inflation hole 154 or port is exposed to the inflation media, such as shown in FIGS. 8A and 8B.
8. The ratchet handle 68 can be depressed further. The next sets of clicks on the ratchet can indicate the inflation of the dilatation balloon 62.
9. The dilatation balloon 62 may rupture the overlying everting balloon 18.
10. The amount of force in the biological lumen dilatation can be governed by a pressure relief valve or by the amount of volume of media 155 that can be placed within the dilatation balloon 62. The dilatation pressure can be monitored by a pressure gauge in or attached to the system handle case 34. The dilation balloon 62 can dilate the cervix with from about 6 atmospheres to about 20 atmospheres. The dilation balloon 62 can initially deliver about 10 atmospheres to about 12 atmospheres with a reduction in pressure as the cervix dilates and the dilatation process is completed. The system can deliver a known volume of media 155 into the dilation balloon 62 irrespective of quantifying or measuring the media pressure 14.
11. The dilatation process may be observed by ultrasound or radiographic imaging.
12. A pressure relief button on the system handle 30 can be activated to remove or reduce dilatation pressure in the media volume 12 in the inner catheter lumen 10.
13. The syringe plunger 94 may be retracted to draw vacuum from the inner catheter lumen 10 and dilation balloon 62, for example loosening the dilation balloon 62 from the cervix, and/or deflating the dilation balloon 62, for example to facilitate removal of the everting balloon system 2 from the cervix.
14. The everting balloon system 2 can be re-pressurized, for example if additional dilatation force is desired in the cervix. For instance, if an additional stenosis in the cervix is visible, the dilatation balloon 62 can be repositioned and inflated in the additional stenosis area.

The everting catheter system can access a bodily cavity (e.g., the uterine cavity or fallopian tubes) to deliver or introduce of tools (e.g., IUDs and instruments), reproductive (e.g., embryos, in vitro fertilization (IVF) or insemination products, such as hormones) media 155 or material, contrast media, dye, therapeutic agents, sclerosing agents to treat the endometrium, insufflation media, or combinations thereof to the cavity. For example, reproductive media can be delivered with a transfer catheter inserted through the inner catheter lumen 10 to the uterine cavity.

Figure 9:
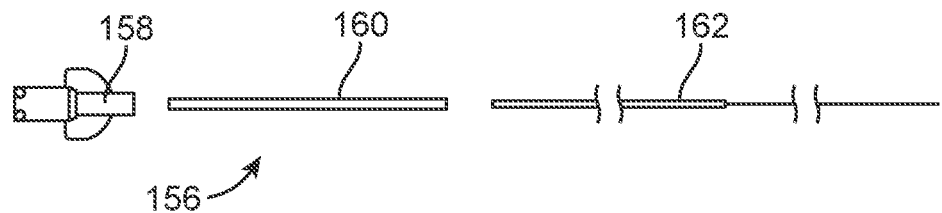
FIG. 9 is an exploded view of a variation of a transfer catheter.

FIG. 9 illustrates that a transfer catheter 156 or insemination catheter can have a transfer connector 158, such as a female luer connector, a strain relief length 160, and a transfer tube 162. The transfer tube 162 can hold the reproductive media. The transfer tube 162 can have a proximal length having a proximal length diameter larger than a distal length diameter of a distal length of the transfer tube 162. A delivery force, for example a positive fluid pressure, can be delivered through the transfer connector 158 and strain relief length 160 to push the contents of the transfer tube 162 into the target site.

The transfer catheter 156 can attach to or inserted through the inlet port 40. The transfer tube 162 can hold an embryo, for example for in vitro fertilization or IVF. The embryo transfer catheter 156 can deliver embryos through the system and to the uterine cavity. The transfer catheter 156 can hold spermatozoa and through the system and to the uterine cavity for intrauterine insemination procedures. The transfer catheter 156 can hold and deliver other materials the deposition of drugs, therapeutic agents, instruments, endoscopes, cytology brushes, other catheters, or combinations thereof through the system and into the uterine cavity. The transfer catheter 156 can be connected to a vacuum source for the aspiration of materials from the uterine cavity or other bodily cavities and lumens.

The transfer catheter 156 and/or materials can be loaded in the inner catheter lumen 10 prior to everting the everting balloon 18 within the vessel or bodily cavity. For example in the case of delivery of reproductive material in the uterine cavity, the transfer catheter 156 can be loaded with washed and prepared semen in the transfer tube 162 and the transfer catheter 156 can be placed in the inner catheter lumen 10.

A guidewire can be inserted through the transfer catheter 156 and/or the remainder of the system, for example to direct the tube or system to the target site 164. The guidewire can be used for recanalization.

The inner catheter 8 can be extended and the everting balloon 18 can evert and unroll through the cervix and into the uterine cavity. Concurrently or subsequently, the transfer catheter 156 can be advanced through the inner catheter lumen 10 into the uterine cavity. Once fully everted or when the transfer catheter 156 becomes extended or exposed from the inner catheter 8 and beyond the everting balloon membrane 24, the reproductive material 166 in the transfer catheter 156 can be deposited by a syringe 74, squeeze bulb, piston, or other pressure system. A second delivery catheter, such as a second insemination, IVF, or drug delivery catheter can be concurrently inserted into the inlet port 40 or a second inlet port. The second delivery catheter can be deployed to the target site 164 concurrent with or subsequent to the transfer catheter 156.

The system handle 30 can have a lead-in area. The lead-in area can, for example, be without steps, edges, bumps, or restrictions that may impede or contact the distal opening of the transfer catheter 156 during passage, for example so that in the case of delivery of insemination material, the transfer catheter 156 can be easily loaded into the system handle 30. An insemination syringe 74 or pump can be attached to the proximal transfer connector to deliver pressure to the transfer tube 162, for example to expel the reproductive material 166 once the distal port of the transfer catheter 156 is positioned at the target site 164 (e.g., after the everting balloon 18 is fully deployed). The actuation of the insemination syringe or pump on a pre-loaded transfer catheter 156 can be performed by the same hand that holds and operates the components of the everting catheter system.

In addition, the transfer catheter 156 can be configured to be introduced into the proximal connector in the handle of the everting catheter system once the system is fully deployed.

The user can perform any or all of the following while using the everting balloon system 2, for example with a single hand:
 a. pressurize the everting catheter system;
 b. position the everting balloon system 2 at the patient's cervix;
 c. maintain the everting balloon system 2 position throughout the procedure;
 d. advance the inner catheter 8 and everting balloon 18;
 e. once extended beyond the everting balloon membrane 24 or inner catheter 8, present the transfer catheter 156 for deposition into the bodily cavity such as a uterine cavity
 f. retract the inner catheter 8 and everting balloon 18; and/or
 g. activate (e.g., toggle) the pressure release lever to remove or release hydraulic or pneumatic pressure from the media volume 12.

Figure 10A:
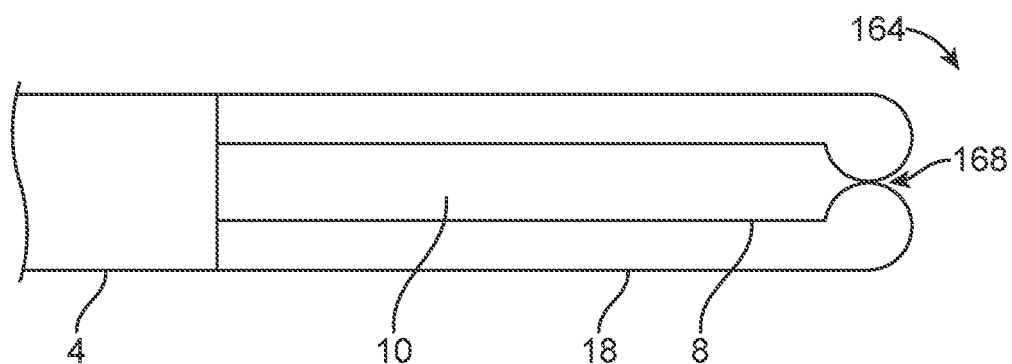
FIGS. 10A through 10C illustrate a variation of method for delivering material to a target site, such as reproductive material delivered to a uterine cavity.
Figure 10B:
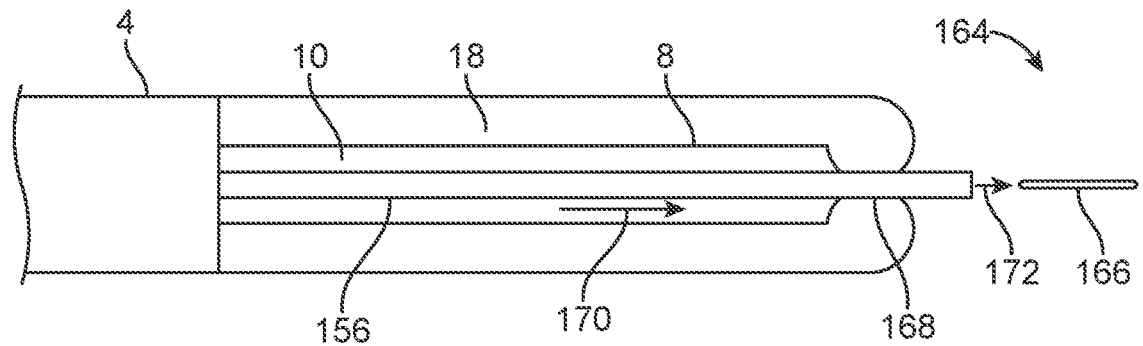
Figure 10C:
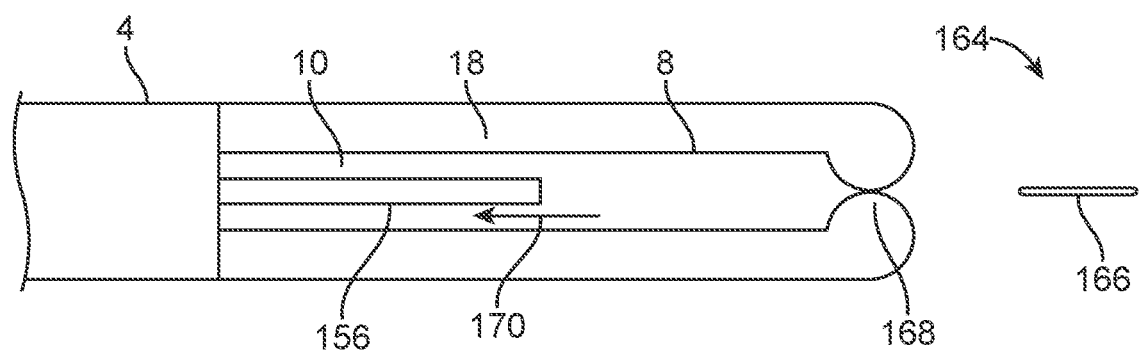

FIGS. 10A through 10C illustrate that the distal end of the everting balloon can form a balloon check valve 168. The length of the everting balloon 18 distal to the distal terminal end of the inner catheter 8 can radially contract to form a tight orifice that can be the balloon check valve 168. The balloon check valve 168 can be an openable barrier that can block or interrupt fluid communication between the inner catheter lumen 10 and the target site 164.

The balloon membrane 6 can have from about 1 mm to about 3 mm of overlapping wall at the balloon check valve 168 closing off the inner catheter lumen 10. The strength or closing pressure of the balloon check valve 168 can be modulated during use. For example the distance of overlap of balloon membrane 6 can be increased or decreased by controlling the amount of excursion available for the inner catheter 8 and everting balloon membrane 24.

FIG. 10B illustrates that the distal end of the transfer catheter 156 can be advanced, as shown by arrow 170, through the inner catheter lumen 10, through the balloon check valve 168, and to the target site 164. The transfer catheter 156 can penetrate or push open the balloon check valve 168 when the transfer catheter 156 moves through the balloon check valve 168. When the terminal distal end of the transfer catheter 156 is distal of the balloon check valve 168 and at the target site 164, the reproductive material 166 loaded in the transfer catheter 156 can be delivered 172 through a distal port of the transfer catheter 156 and into the target site 164, such as the uterine cavity.

FIG. 10C illustrates that the transfer catheter 156 can be retracted through the balloon check valve 168 and the inner catheter lumen 10 after the reproductive material is deposited at the target site 164. The balloon check valve 168 can close as the transfer catheter 156 is retracted through the balloon check valve 168. The balloon check valve 168 can maintain a seal between the inner catheter lumen 10 and the target site 164 when the transfer catheter advances 170 through, remains stationary within, and is retracted through the balloon check valve 168.

The reproductive material 166 can be isolated from vacuum effect or the retraction of reproductive material 166 from the target site 164 as a result of the vacuum forces created by the withdrawal of the transfer catheter 156 through the system once the deposition of reproductive material 166 is completed. The balloon check valve 168 can reduce or eliminate vacuum effect for embryo transfer.

The balloon check valve 166 can be a tactile indicator for the physician when passing the transfer catheter 156 through the everting balloon system 2. In transfer procedures, depending upon physician preference or patient anatomy, for example, the amount of insertion of the transfer catheter 156 through the distal end of the everting system can vary from patient to patient. As the distal end of the transfer catheter 156 passes through the balloon check valve 168, the resistance created by the balloon check valve 168 can be felt by the physician on the proximal end of the transfer catheter 156. Depending upon the length of balloon chosen to act as a balloon check valve 168, the degree or amount of resistance can be modulated. In some procedural settings there may be a compromised ability to see the amount of insertion of the transfer catheter 156 into the everting balloon 18, or physical depth indicia or markings on the proximal end of the transfer catheter 156. The compromised ability to see may be due to low light within the procedure room so that imaging and visualization of monitors can be enhanced. In addition, the physical relationship of the physician, embryologist, or other persons or equipment in the procedure room may compromise the ability to see easily the amount of insertion into the everting catheter. The tactile sensation of the resistance of the balloon check valve 168 can create a palpable indicator that the transfer catheter 156 is at the distal end of the everting balloon 18.

The everting balloon system 2 can be used to access and seal the uterine cavity, for example, for the deposition of reproductive material 172 for long duration intrauterine insemination.

Figure 11A:
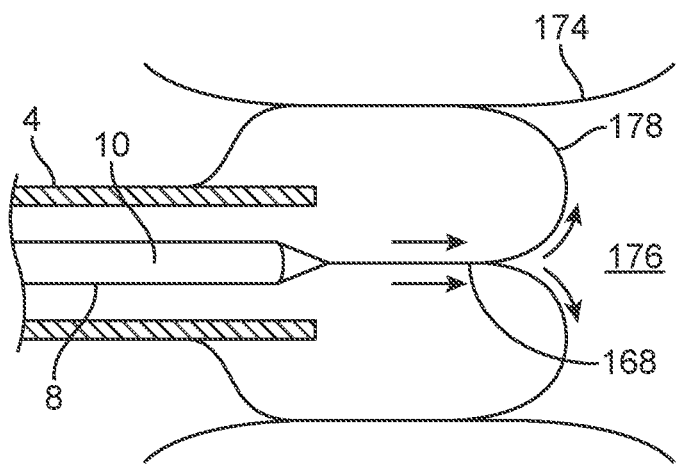
FIGS. 11A through 11C illustrate a variation of a method for delivering material to a target site, such as reproductive material delivered to a uterine cavity.
Figure 11B:
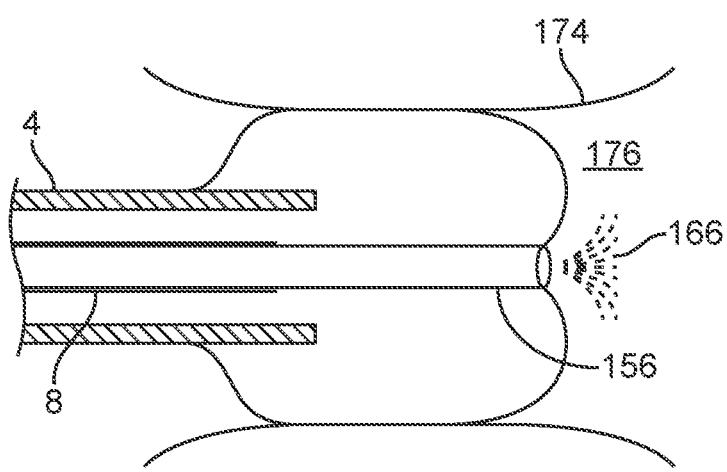
Figure 11C:
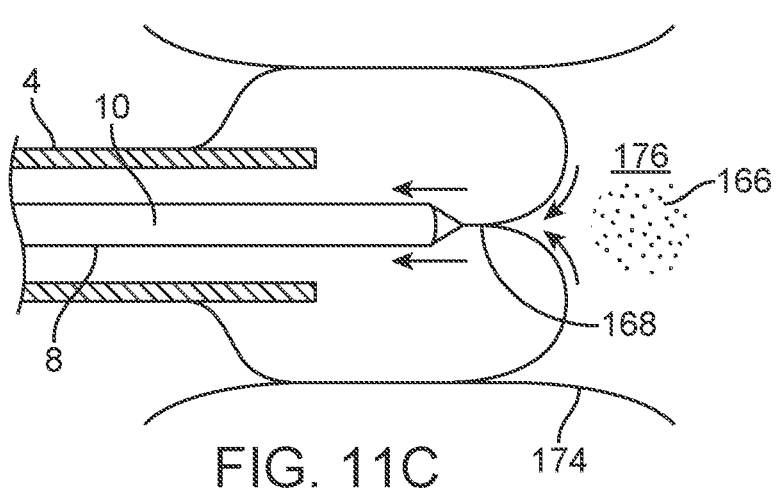

FIGS. 11A through 11C illustrate that the everting balloon membrane 24 can create a seal within the cervical canal (e.g., against the cervical canal walls 174) as the everting balloon 18 traverses the cervical canal. FIG. 11A illustrates that the everting balloon membrane 24 can unroll and advance along the cervical walls, as shown by arrows, as the balloon is pressurized and the inner catheter 8 is distally advanced. The outer catheter 4 can also seal against the cervical canal wall 174. For example, the outer catheter 4 outer diameter can be equal to the everting balloon outer diameter.

FIG. 11B illustrates that the transfer catheter 156 can advance distally within the everting balloon 18 and the inner catheter lumen 10. The transfer catheter 156 can deposit the reproductive material 166 (e.g., sperm) within the uterine cavity 176.

FIG. 11C illustrates that the transfer catheter 156 and/or the inner catheter 8 can be retracted (e.g., from about 3 mm to about 10 mm) or inverted, as shown by arrows, to close the distal end of the inner catheter lumen 10, as shown by arrows, with respect to the uterine cavity 176. The distal opening of the balloon 178 can close, for example due to the pressure within the everting balloon 18 forcing the everting balloon 18 to form the balloon check valve 168. The balloon check valve 168 can seal the cervical canal and the uterine cavity 176 from the inner catheter lumen 10. The reproductive materials 166 can remain in the uterine cavity 176 without being expelled through the cervix.

Figure 12A:
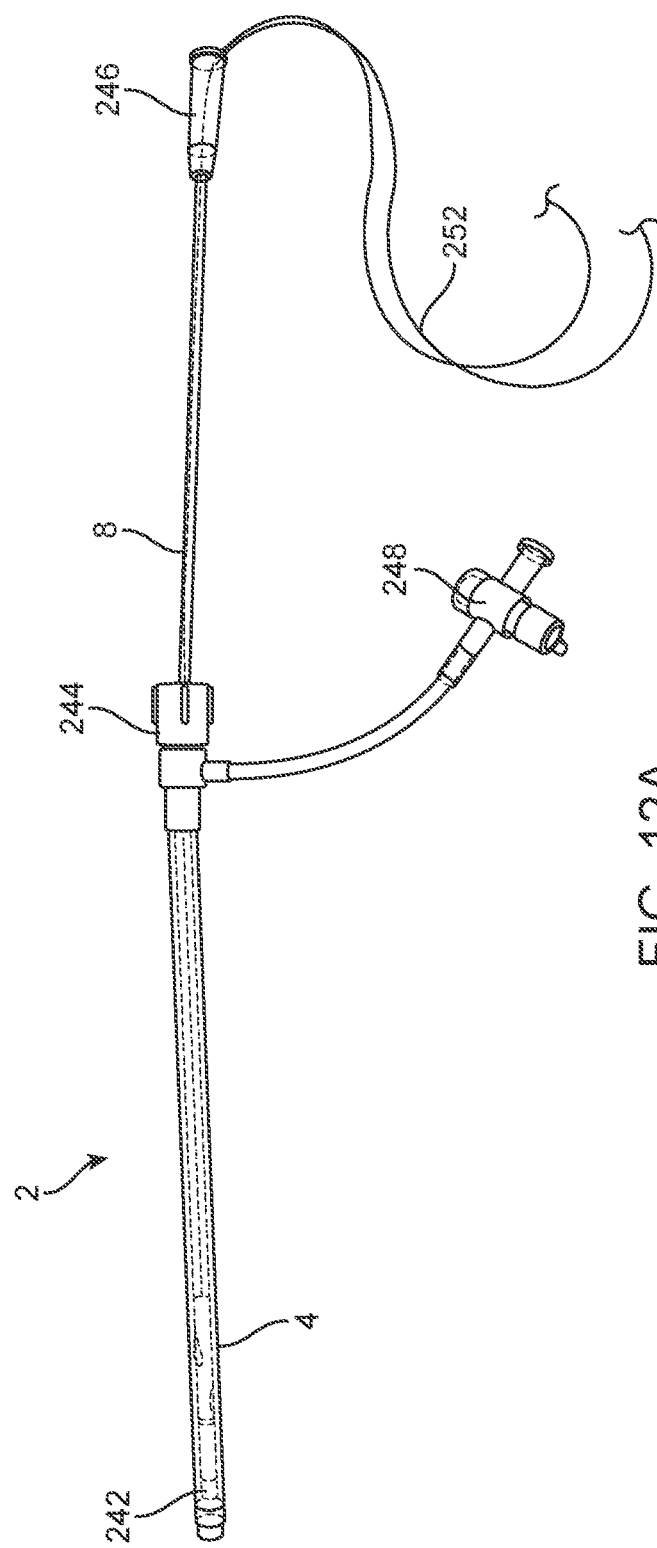
FIGS. 12A to 12E illustrate an everting catheter for performing an IUD placement procedure with an everting membrane.

FIGS. 12A to 12E illustrate of an everting catheter for performing an IUD placement procedure. FIG. 12A shows an everting catheter with an IUD contained in an everting catheter system 2 in the inverted membrane position. Everting membrane and IUD (not visible in this figure) are contained within outer catheter 4 with acorn tip 242 at the distal end. Acorn tip 242 can have an opening at the distal end (not visible). On the proximal end of outer catheter 4 there is a t-fitting or Y-fitting 244 which contains an x-ring gasket (not visible). Extension tubing and stopcock 248 supplies inflation or hydraulic energy to the everting catheter system. Hydraulic energy can be supplied by saline, air, a combination of saline and air, or gases such as CO2, contrast media, culture media, and other fluids. In operation, hydraulic energy can be in the range of 2 to 4 atmospheres, or 1 to 6 atmospheres. Inner catheter 8 is translatable within the outer catheter 4 to advance and retract the everting membrane (not visible). On the proximal end of the inner catheter 8 there is a proximal hub 246 that is designed to allow passage of the IUD suture 252. Other embodiments may not require the IUD suture to be exposed from the inner catheter.

Figure 12B:
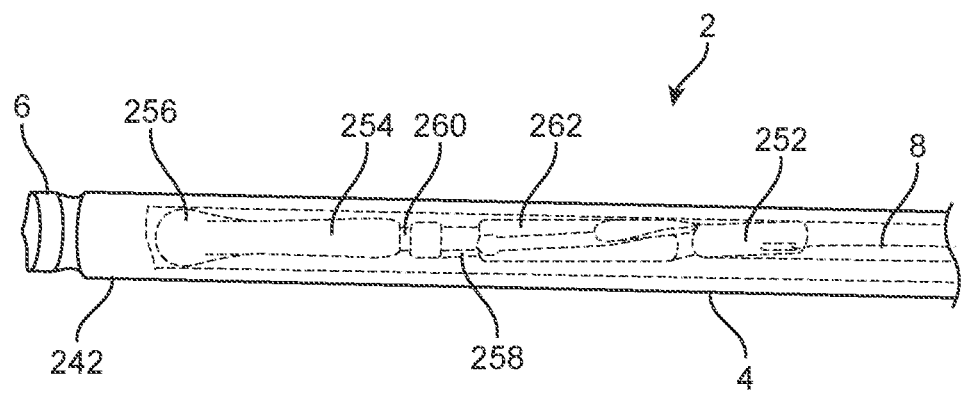

FIG. 12B shows the distal end of the everting catheter with IUD 254 visible in the everted membrane which is only partially everted from acorn tip 242. IUD 254 can be in a collapsed condition within the membrane 6. IUD suture 252 can be proximal to the IUD 254. The IUD suture 252 can be within the central lumen of inner catheter 8. IUD 254 can have rounded distal ends 256 and stem 258. IUD 254 can have radio-opaque marker band 260, copper or drug or hormone eluting section 262, and other features.

Figure 12C:
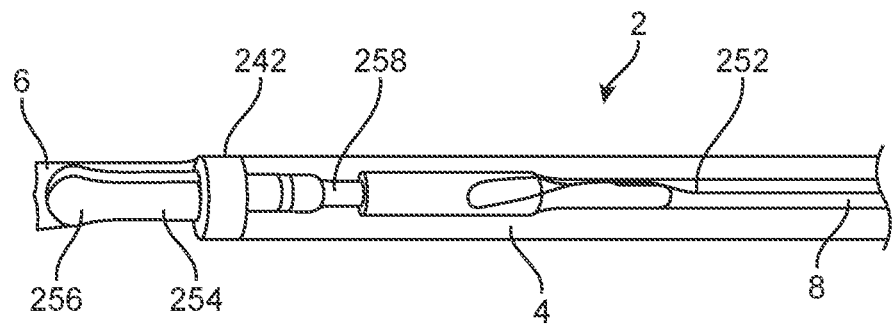

FIG. 12C shows the advancement of the everting membrane 6 pulling IUD 254 through the distal end of outer catheter 4 and opening on acorn tip 242. Eversion of the membrane can be performed in response to hydraulic energy or pressure within the everting catheter system 2 through the inflation tubing and stopcock (not shown). The everting membrane 6 responds to hydraulic energy to roll inside out. The advancement of the everting membrane 6 can be performed by the user translating the inner catheter (not visible) or automatically in response to the hydraulic energy. The everting membrane can be dimensioned in a range of 1 mm to 5 mm in diameter for the endocervical canal or 4.0 to 4.5 mm in outer diameter when pressurized to 2 atmospheres. The everting membrane can have an outer diameter range of 2 mm to 7 mm, with a wall thickness of 0.001" to 0.004", or 0.0015". The everting membrane can be manufactured from irradiated polyolefin, polyurethane, Pebax, silicone, or other flexible membrane material. The everting membrane wall thickness could have a range of 0.002" to 0.010" depending upon the modulus of the membrane material.

Figure 12D:
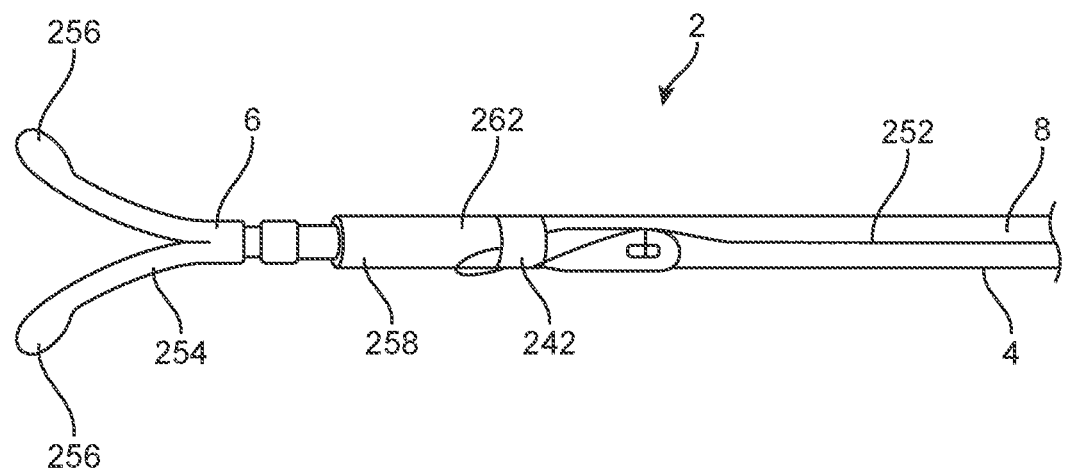

FIG. 12D shows the distal end of the outer catheter 4 and acorn tip 242 with everting membrane 6 in a further stage of eversion advancing IUD 254 through the distal end opening in acorn tip 242. Rounded ends 256 of IUD 254 are in the initial stages of returning to its natural state as opposed to its collapsed state. In its natural state, IUD 254 can have a "T" or "Y" shape although other shapes and configurations are possible for intrauterine devices.

Figure 12E:
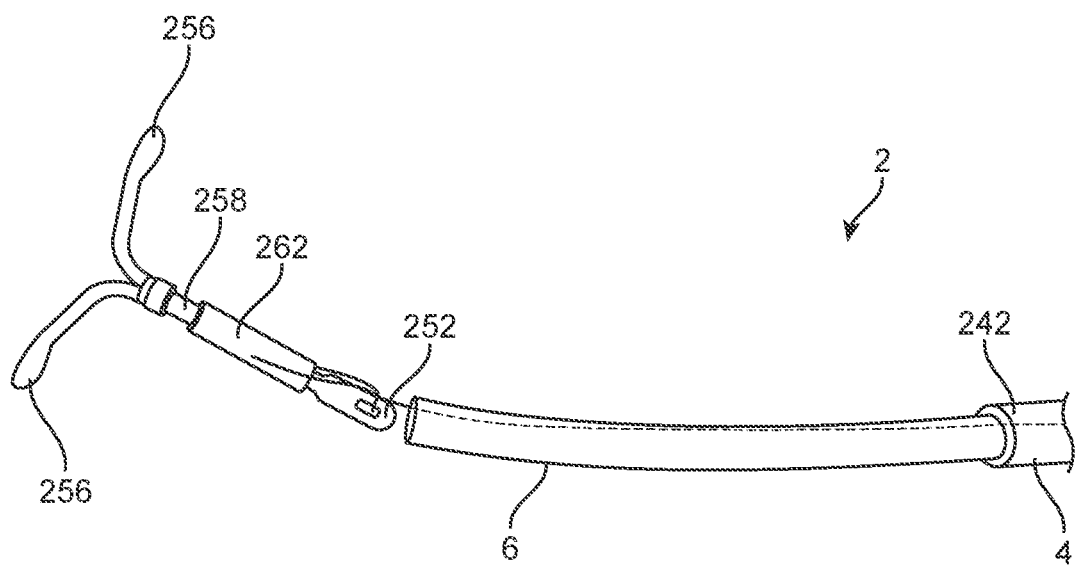

FIG. 12E shows the completion of the eversion process with everting membrane 6 advanced further beyond the acorn tip 242 and fully exposing IUD 254 that can now be in its natural (i.e., unbiased or mechanically relaxed) state or "T" shape. Stem 258 and hormone or drug eluting section 262 are fully exposed from the distal end of membrane 6. Certain IUDs are equipped with bands or rings of copper material as a spermicidal agent. IUD suture 252 can still be within the central lumen of membrane 6 and inner catheter (not visible). At full exposure outside of membrane 6, IUD 254 can be at the insertion depth within the uterine cavity. The insertion depth of the IUD 254 within the uterine cavity can be determined or prescribed by the length of the membrane 6, the amount of eversion performed by the user during the translation of the inner catheter 8, which can vary depending upon the desired depth of insertion. In addition, the outer catheter 4 can be configured with telescoping tubes (not shown) that can change the membrane length and the insertion depth within the uterine cavity.

Figure 13A:
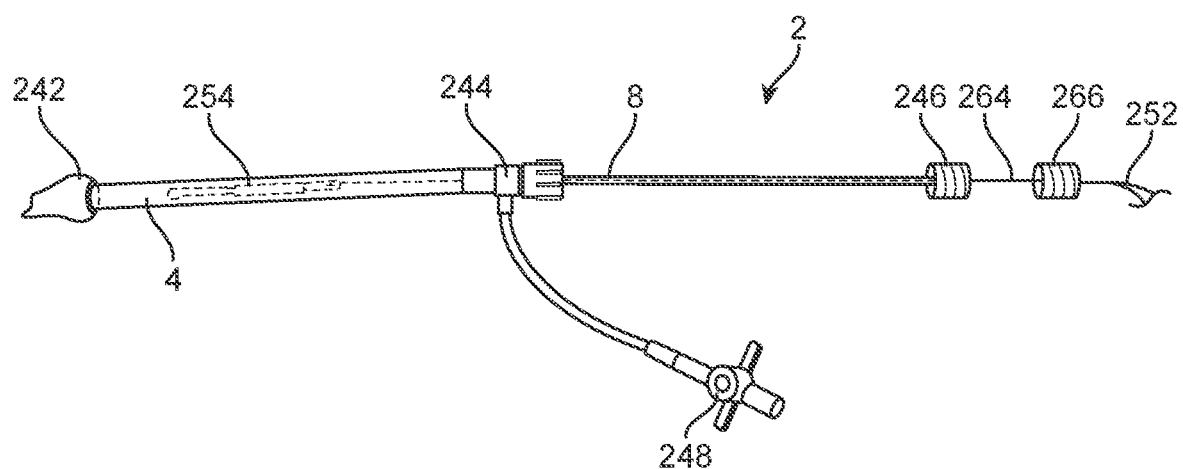
FIGS. 13A to 13I illustrate in both side views and top views additional derivations built into the distal end of the everting membrane and inner catheter.

FIGS. 13A to 13I illustrate additional derivations for an everting catheter system 2 for IUD placement. FIG. 13A shows everting catheter system 2 with IUD 254 in a collapsed state within the everting membrane 6 (not visible) within outer catheter 4. Inner catheter 8 can be proximal to Y-fitting 244 and continues within outer catheter 4. Everting membrane 6 can be connected to the distal end of inner catheter 8 and to the distal end of outer catheter 4. Acorn tip 242 can be located at the distal end of outer catheter 4. Everting membrane 6 can be pressurized by fluid, gas, or a combination of both through extension tubing and stopcock 248. Within inner catheter 8 can be pusher 264 which can be proximal to inner catheter hub 246. Pusher 264 can be a hollow tube with pusher hub 266 that can contain IUD suture 252 within its inner lumen.

Figure 13B:
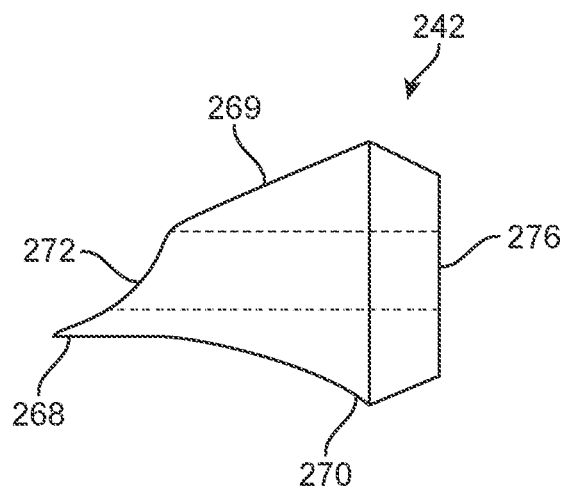

FIG. 13B shows in a side view acorn tip 242 with dashed lines indicating through lumen 276 within the acorn tip. Acorn tip 242 can be used to seat the everting catheter system 2 at the exocervix of the patient. Acorn tip 242 contains intubation tip 268 on the posterior surface that can be designed to gain purchase or intubate the opening of cervix with a rounded surface 269 on the anterior portion. Acorn tip 242 can have outer shoulders 270 to provide a stopping mechanism to avoid inadvertent insertion of the outer catheter 4 within the cervical canal of the patient. Distal end opening 272 can be configured to allow the everting membrane deliver the IUD (both not shown).

Figure 13C:
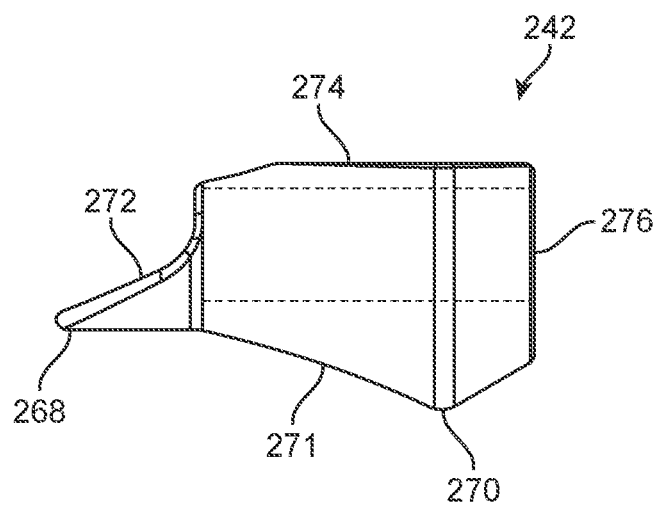
Figure 13D:
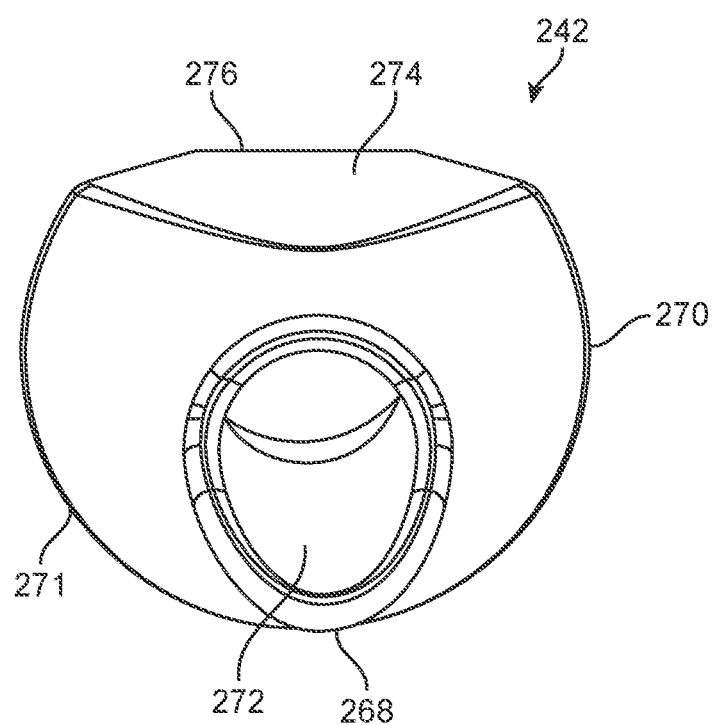

FIGS. 13C and 13D show another type of acorn tip 242 with lower profile anterior surface 274 with outer shoulders 270 that are reduced in the anterior portion of circumference of acorn tip 242. Lower profile anterior surface 274 provides the physician greater viewing angle of the exocervix when placing the everting catheter (not shown). The lower profile anterior surface can be used by the physician to gain better visualization of the exocervix while maintaining the functions of the acorn tip in regards to intubating the exocervix, gaining purchase, and providing a stopping mechanism from inadvertent advancement of the outer catheter into the cervical canal. Alternative acorn tip 242 contains an intubation tip 268 on its distal end on the posterior surface to facilitate initial device placement at the exocervix of the patient with ramp 271 leading to shoulder 270. Dashed lines indicate through lumen 276 with distal end opening 272.

Figure 13E:
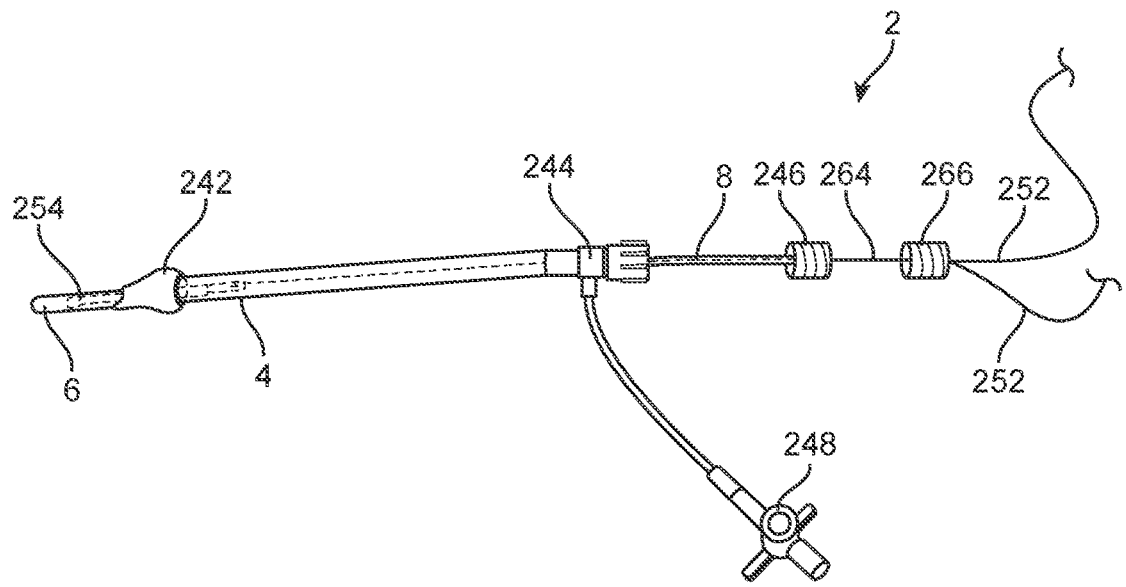

Returning back to an alternative embodiment of everting catheter system 2, FIG. 13E shows IUD 254 being advanced by everting membrane 6 in response to the advancement of inner catheter 8 within outer catheter 4 using hydraulic energy supplied in extension tubing and stopcock 248. In conjunction, pusher 264 can advance with everting membrane 6 with two strands of IUD suture 252 exiting pusher hub 266.

Figure 13F:
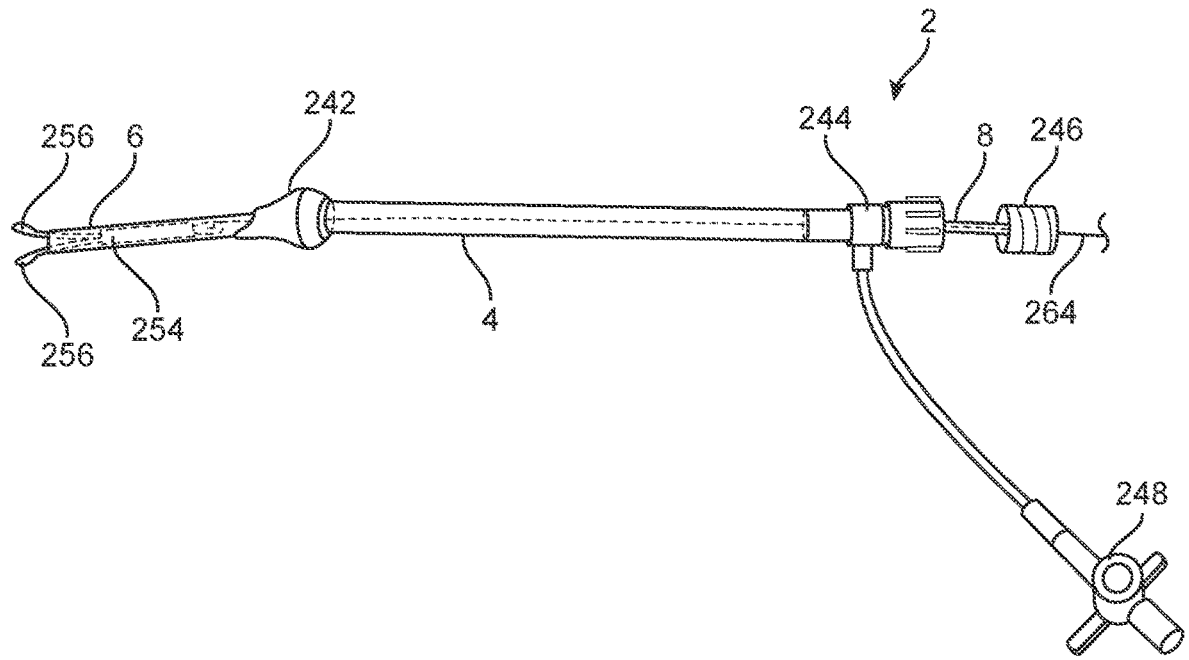

FIG. 13F shows further advancement of IUD 254 with everting membrane 6 and translation of inner catheter 8 within outer catheter 4. Rounded ends 256 are exposed distal at the end of the everting membrane 6 as the membrane everts inside out and pulls the IUD forward.

Figure 13G:
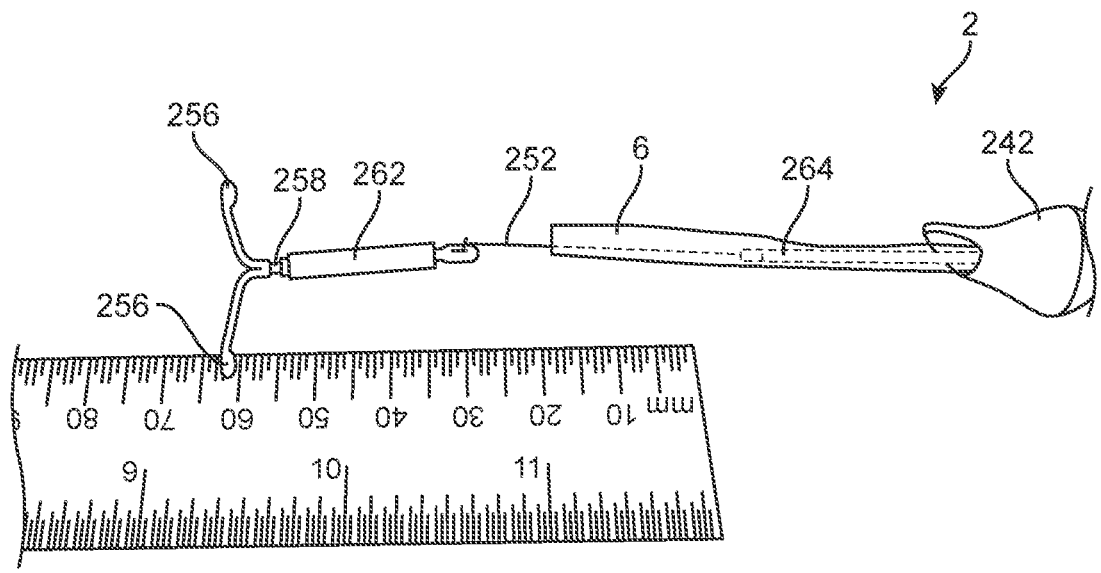

FIG. 13G shows IUD 254 released from everting membrane 6 with IUD fully in its natural state or "T" or "Y" shape. IUD suture 252 can be proximal to the IUD and runs through everting membrane 6, pusher 264, and inner catheter (not visible). To complete IUD release, pusher 264 advances IUD 254 beyond the distal end of everting membrane 6.

Figure 13H:
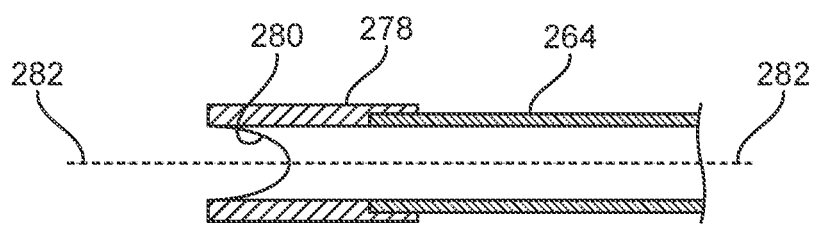
Figure 13I:
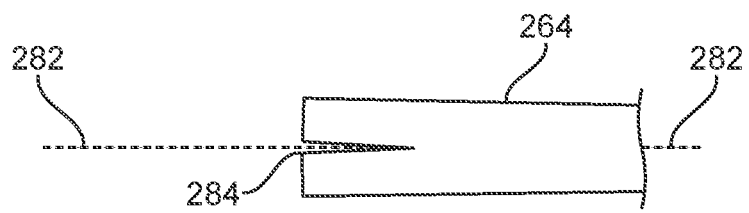

FIGS. 13H and 13I illustrate alternative embodiments of the distal end of pusher 264. FIG. 13H shows distal end of pusher 264 with pusher cup 278 with concave opening 280 to accept and hold the profile of the proximal end of IUD 254 (not shown). Pusher 264 can have through lumen with central axis 282. Distal end pusher cup 278 facilitates the handling and loading of IUD 254 within an everting catheter (not shown).

FIG. 13I shows an alternative form of distal end of pusher 264 with through lumen and central axis 282 and with a split tube opening 284 at the distal end. Split tube opening 284 can be configured to open and accept and hold the proximal end of IUD 254 (not shown). Distal end split tube opening 284 facilitates the handling and loading of IUD 254 within an everting catheter (not shown).

Figure 14A:
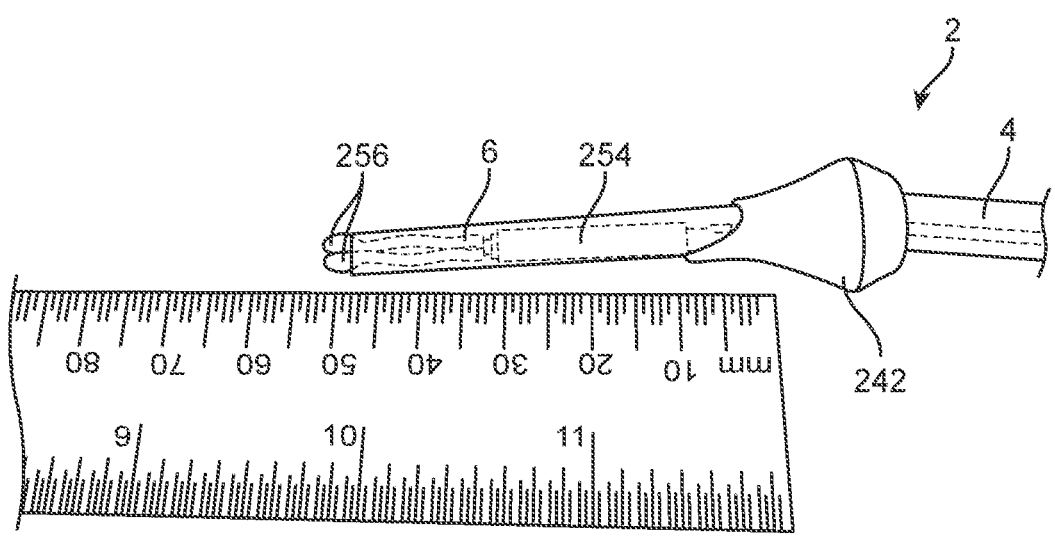
Figure 14D:
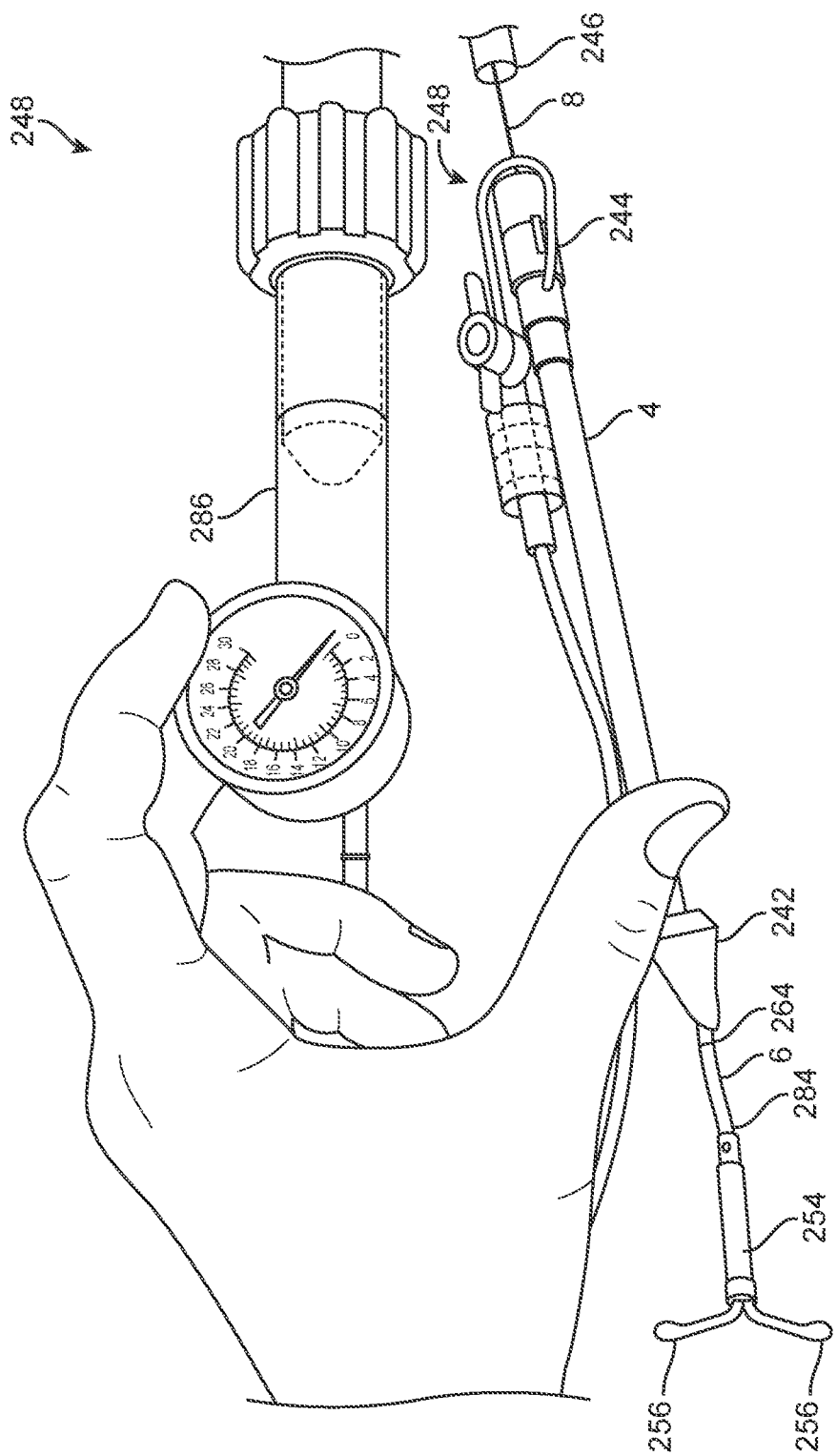

FIGS. 14A and 14D illustrate the advancement of IUD 254 within an everting membrane 6 from the collapsed state to the release of IUD 254 and return to its natural state or "T" shape. FIG. 14A shows the everting membrane 6 advancing through acorn tip 242 pulling IUD 254 in a collapsed, low profile state within an everting catheter system 2. Round ends 256 are compressed by the everting membrane 6 in response to the hydraulic energy supplied through extension tubing and stopcock (not visible).

FIGS. 14B and 14C further illustrate the advancement of IUD 254 within an everting membrane 6 within an everting catheter system 2. As IUD 254 is pulled forward by the everting membrane, IUD 254 can return to its natural state or a "T" or "Y" shape. FIG. 14B shows the everting membrane 6 in a pressurized state via hydraulic energy. IUD suture 252 can be contained within the distal end of pusher 264 within split opening 284.

FIG. 14D illustrates another embodiment of everting catheter system 2 in which the hydraulic energy can be removed by a pressure source 286 via extension tubing and stopcock 248. Once hydraulic energy is removed from everting catheter system 2, everting membrane 6 can no longer grip IUD 254 and pusher 264 can advance the proximal end of IUD beyond the distal opening of everting membrane. Pressure source 286 an be an inflation device as shown or other devices such as a syringe, a syringe and compliant tube, a pump, or a pressurized cannister or container.

Figure 15A:
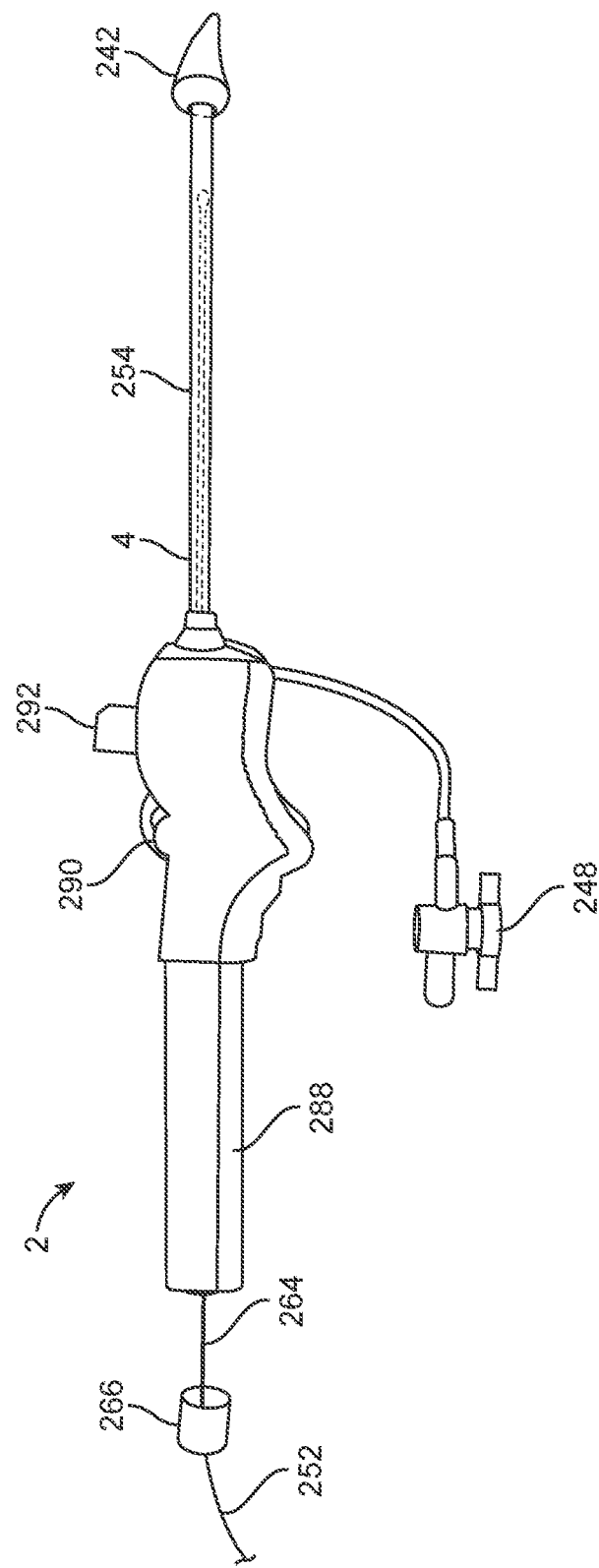
FIGS. 15A through 15D illustrate an automatic one-handed eversion mechanism for IUD placement.

FIG. 15A illustrates everting catheter system 2 equipped with a one-handed delivery mechanism. On the proximal end of everting catheter system 2, housing 288 can be configured with rolling wheel 290 and outer catheter release button 292. At the distal end, acorn tip 242 can be designed to engage the exocervix when placed in the patient for IUD delivery and placement. IUD 254 can be visible within outer catheter 4. Extension tubing and stopcock 248 can be located on the posterior portion of housing 288. Exiting the proximal portion of housing 288, pusher 264 and pusher hub 266 can be visible with IUD suture 252 protruding the through lumen of pusher 264.

Figure 15B:
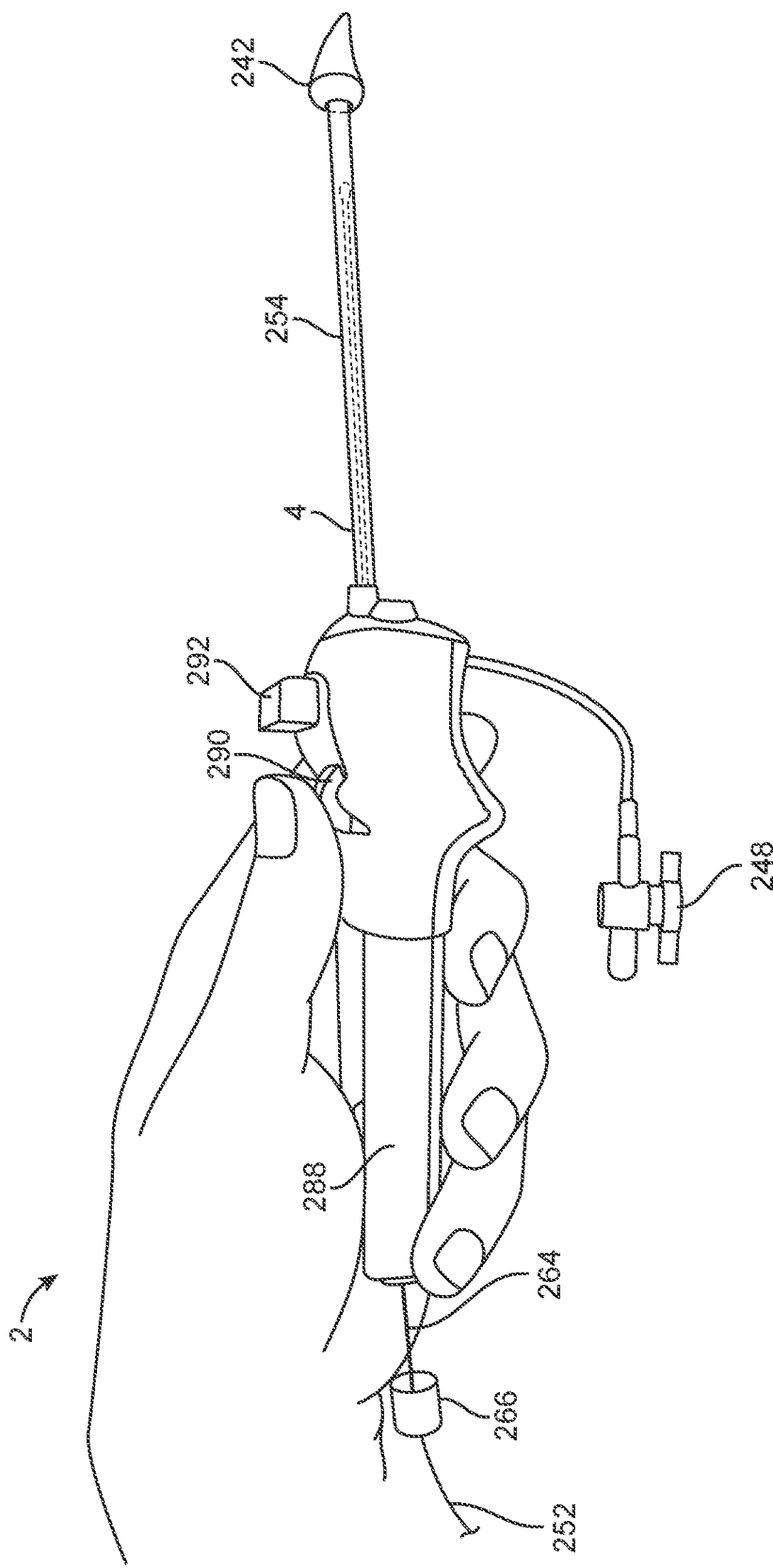

FIG. 15B demonstrates the one-handed operating mechanism of everting catheter system 2 using housing 288. The operator's thumb can be placed on rolling wheel 290 with outer catheter release button 292 in close proximity. IUD 254 can be visible within outer catheter 4 and pusher 264 with pusher hub 266 can be visible exiting the proximal portion of the housing.

Figure 15C:
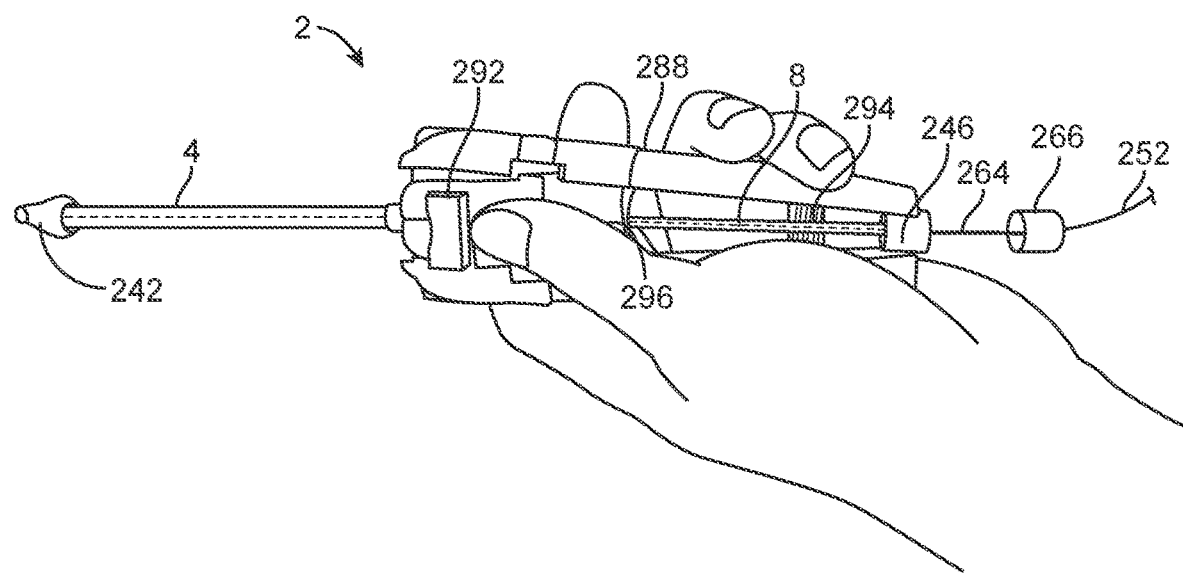

FIG. 15C shows a top view of the one-handed mechanism of everting catheter system 2 in which the inner catheter 8 can be visible in housing 288. Also visible are inner catheter hub 246 with pusher 264 protruding from the proximal portion of the inner catheter hub. IUD suture 252 can be visible protruding from the proximal opening of pusher hub 266. Also visible within housing 288 can be pusher stop 294 and gear wheel housing 296 under the thumb of the operator.

Figure 15D:
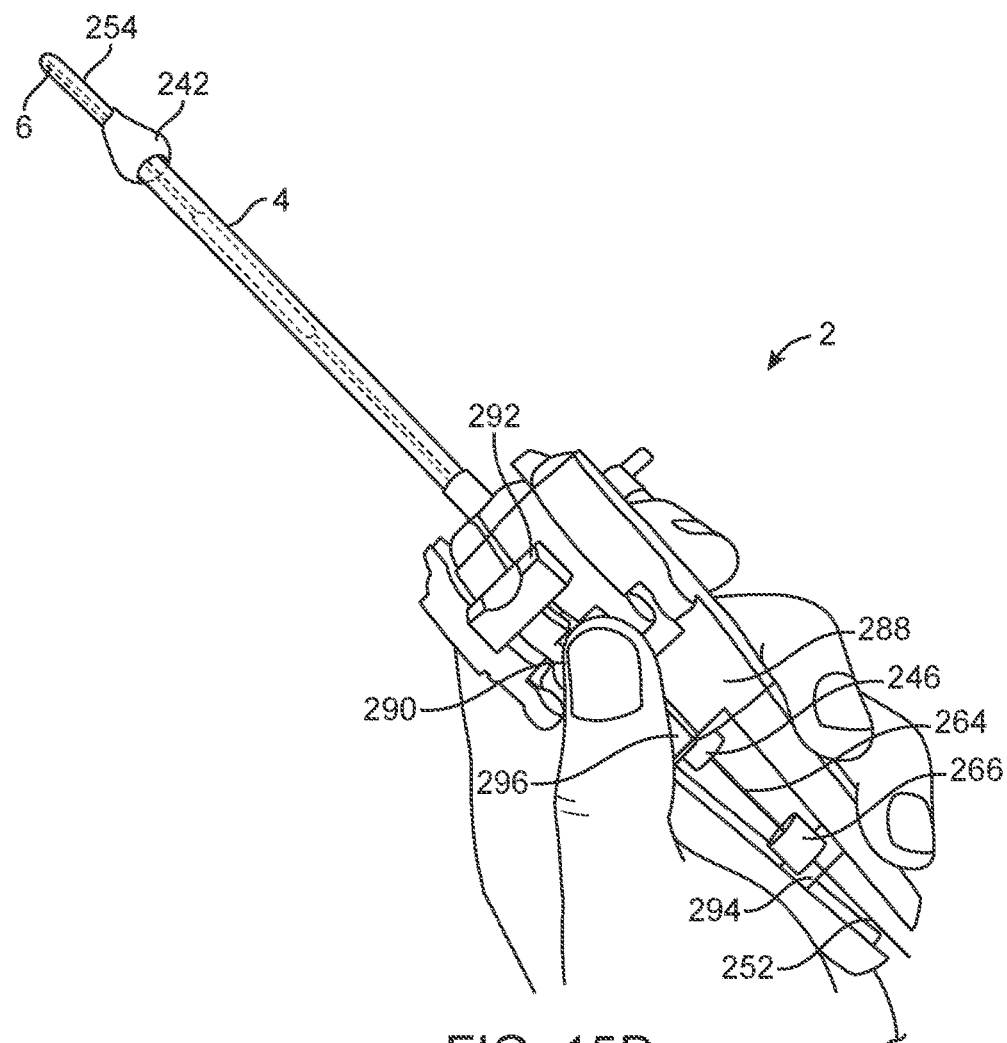

FIG. 15D illustrates further in a top view the one-handed operation of everting catheter system 2 during the advancement of everting membrane 6 puling IUD 254 through acorn tip 242. Rolling wheel 290 (partially visible under the thumb of the operator) can be used to advance inner catheter 8 which allows the everting membrane to advance. Advancement of the everting membrane 6 can be limited when inner catheter hub 246 reaches gear wheel housing 296. As the inner catheter 8 can be advanced into the outer catheter 4, inner catheter hub 246 reaches gear wheel housing 296 and advances pusher 264 until pusher hub 266 mechanically engages pusher stop 294. In operation, the operator will actuate outer catheter release button 292 that will allow the outer catheter 4 and attached everting membrane 6 to retract while pusher 264 maintains in place in relation to housing 288 with pusher stop 294. The distal end of pusher 264 thereby advances IUD 254 out of the distal end of everting membrane 6 and releasing IUD 254 in the uterine cavity. In operation, the operator will remove the entire everting catheter system 2 and having the IUD suture 252 threading out of pusher 264.

FIGS. 16A to 16J illustrate another embodiment of everting catheter system 2 with handle 30. Protruding distal to handle 600 can be outer catheter 4 and protruding proximal to the handle can be pusher 264 with IUD sutures 252 exiting the pusher hub 266. On the anterior portion of handle 600 can be inner catheter button 298 and outer catheter release button 292. Protruding on the posterior portion of handle 600 can be extension tubing and stopcock 248 (partially visible).

FIG. 16B shows inner catheter button 298 being advanced within housing slot 308 on the anterior surface of housing 288. Inner catheter button 298 is attached to the proximal end of inner catheter (not shown) and its advancement translates the inner catheter and everting membrane to deliver an IUD (not shown). In operation, inner catheter button 298 advances until it engages outer catheter release button 292 also on the anterior surface of housing 288.

FIG. 16C shows the retraction of outer catheter release button 292 which performs the release of the IUD from the everting catheter (not shown).

FIG. 16D provides information on how housing 288 works with everting catheter system 2 to perform the advancement and release of the IUD (not shown). In FIG. 16D, the anterior portion of housing 288 is removed showing the interior portions of the everting catheter system 2 including inner catheter hub 246. Alternatively, inner catheter hub 246 can be eliminated by inner catheter button 298 or have both devices as shown. Also visible is pusher 264 and pusher hub 266 with IUD sutures 252 exiting the proximal portion of the pusher hub. Outer catheter release button 292 and inner catheter button 298 is also visible and at this position, the advancement of the everting membrane (not shown) is complete. Contained within the posterior portion of housing 288 are inflation tubing slot 300 and pusher engagement tabs 302 which is configured to mechanically hold pusher hub 266 at the completion of the eversion step. Also visible are housing holes 304 that are designed to snap the anterior and posterior sections of housing 288.

FIG. 16E shows a cut-away view of the proximal portion of Y-fitting 244 with inner catheter 8 exiting the proximal of the Y-fitting. Extension tubing and stopcock 248 (stopcock not shown) is exiting posteriorly from Y-fitting 244 and through housing 288 through inflation tubing slot 300. Outer tubing release button 292 is mechanically attached to Y-fitting 244 and can be retracted in housing 288 along inflation tubing slot 300.

FIG. 16F shows the inflation tubing slot 300 on the posterior surface of housing 288 in another cut-away view. Extension tubing and stopcock 248 (stopcock not shown) is visible in inflation tubing slot 300.

FIG. 16G shows a cut-away view of the proximal portion of housing 288 and proximal hole 306. Cut away view of pusher 264 is visible exiting from the proximal portion of inner catheter hub 246. The internal track of the pusher engagement tabs 302 that progressively gets narrower as it extends from the proximal portion of housing 288 to the distal portion is visible on the internal posterior surface of housing 288. Pusher hub 266 can have a conical or tapered profile on its distal portion to travel through the pusher engagement tabs 302. The flat proximal portion of pusher hub 266 can serve as a mechanical detent in the proximal direction once the pusher hub 266 extends beyond the pusher engagement tabs 302.

FIG. 16H shows the initial step of IUD delivery and placement with another cut-away view of the right-hand side of housing 288 with outer catheter 4 distal to Y-fitting 244 and attached to outer catheter release button 292. Also, on the anterior surface of the housing and in housing slot 308 is inner catheter button 298. Exiting proximal to inner catheter 8 and inner catheter button is pusher 264. Attached to the proximal end of pusher 264 is the pusher hub 266 with through lumen for IUD sutures 252.

FIG. 16I shows in the same cut away view the range of advancement of inner catheter button 298 during the eversion step with everting catheter system 2 hydraulically pressurized through extension tubing and stopcock 248 (stopcock not shown). This embodiment shows an advancement of the inner catheter 8 within outer catheter 4 of 12.6 cm. This distance of advancement corresponds to an insertion depth within the uterine cavity of 6.3 cm. Other lengths of advancement are possible from 3 cm to 24 cm. In addition, the depth of insertion can be under the physician's control by stopping the eversion step at any point during the process.

FIG. 16J shows the release step of the IUD delivery process with everting catheter system 2 in which outer catheter release button 292 is retracted bringing pusher 264 through inner catheter 8 to advance the IUD (not shown) through the everting membrane (not shown).

Figure 17A:
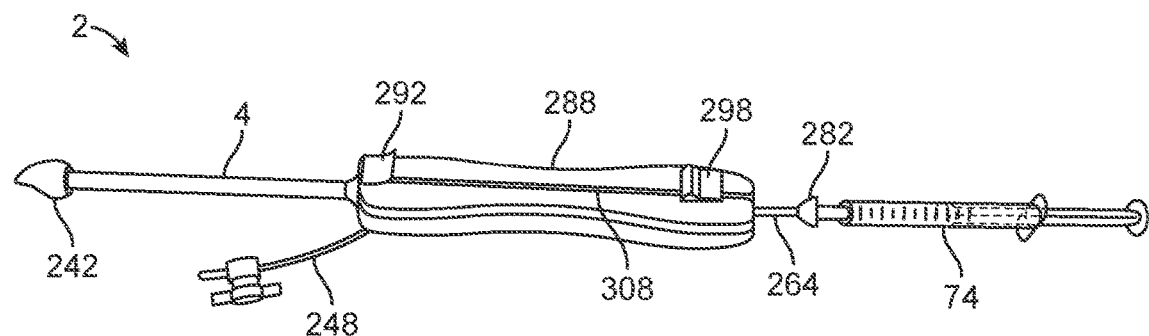
FIGS. 17A to 17I illustrate a variation of an everting catheter that can deliver an IUD within the uterine cavity.

FIGS. 17A to 17I illustrate further embodiments of an everting catheter that delivers an IUD. FIG. 17A shows everting catheter system 2 with housing 288 with pusher 264 and pusher luer hub 310 exiting proximal to the housing. Pusher luer hub 310 is configured to accept a syringe 74 or other irrigation source to provide fluid, saline, contrast media, sonographic media, drugs or therapeutic agents, or a gas or air through the central lumen of everting catheter system 2. Irrigation fluid or media can facilitate visual identification of the exocervix or the uterine cavity with ultrasonography or fluoroscopy.

Figure 17B:
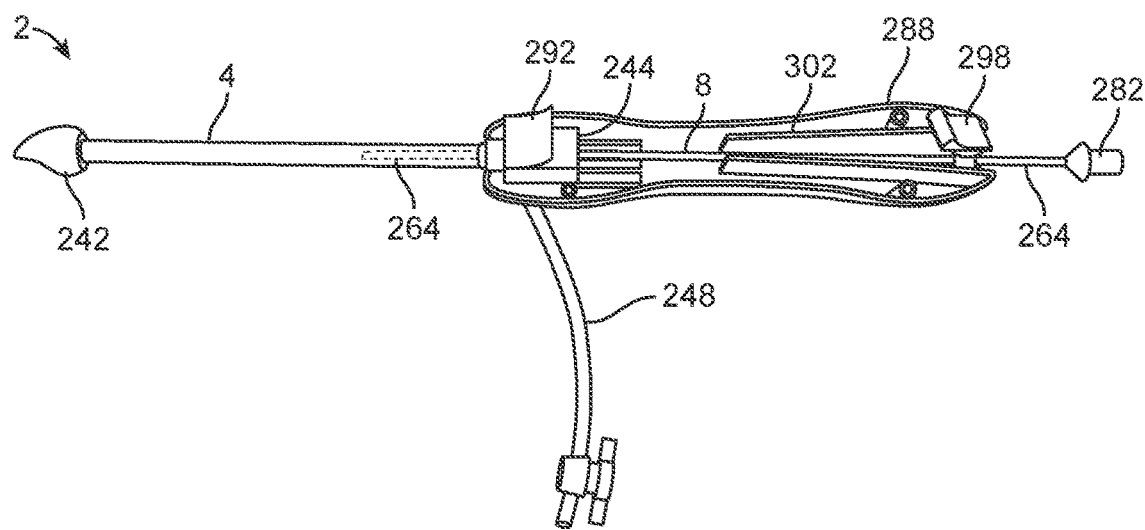

FIG. 17B shows everting catheter system 2 at the initial stage of the eversion process with anterior portion of housing 288 removed for identification of internal parts and mechanisms.

Figure 17C:
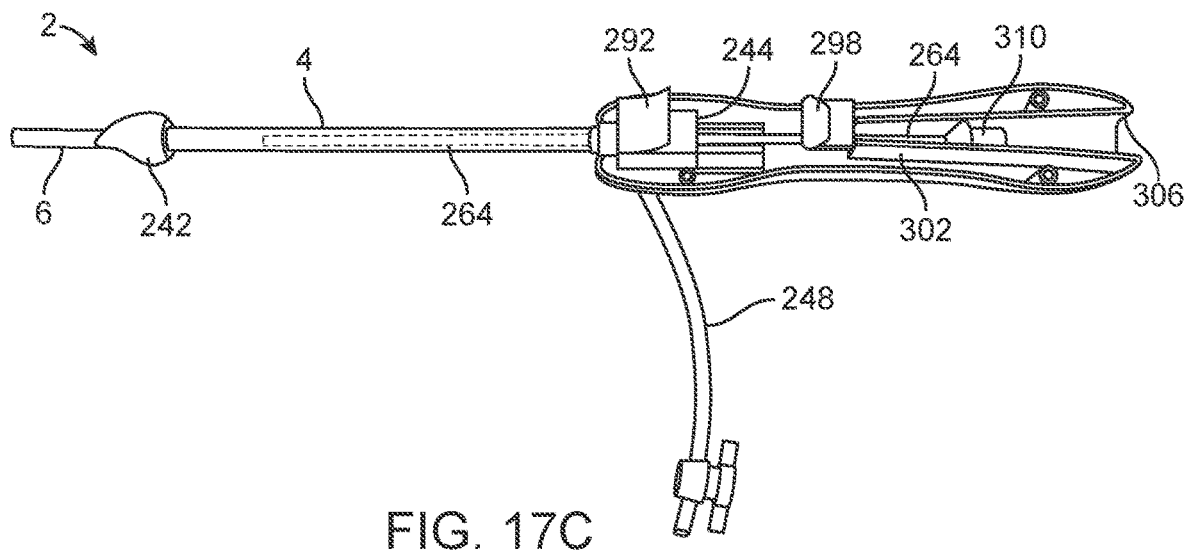

FIG. 17C shows everting catheter system 2 with hydraulic energy is supplied through extension tubing and stopcock 248. Inner catheter button 298 is advanced to translate inner catheter 8 within outer catheter 4. Everting membrane 6 exits distal to acorn tip 242 and pulls IUD (not shown) and pusher 264 through the central lumen of everting catheter system 2. Pusher luer hub 310 is translated through proximal hole 306 of housing 288 and into the track of pusher engagement tabs 302.

Figure 17D:
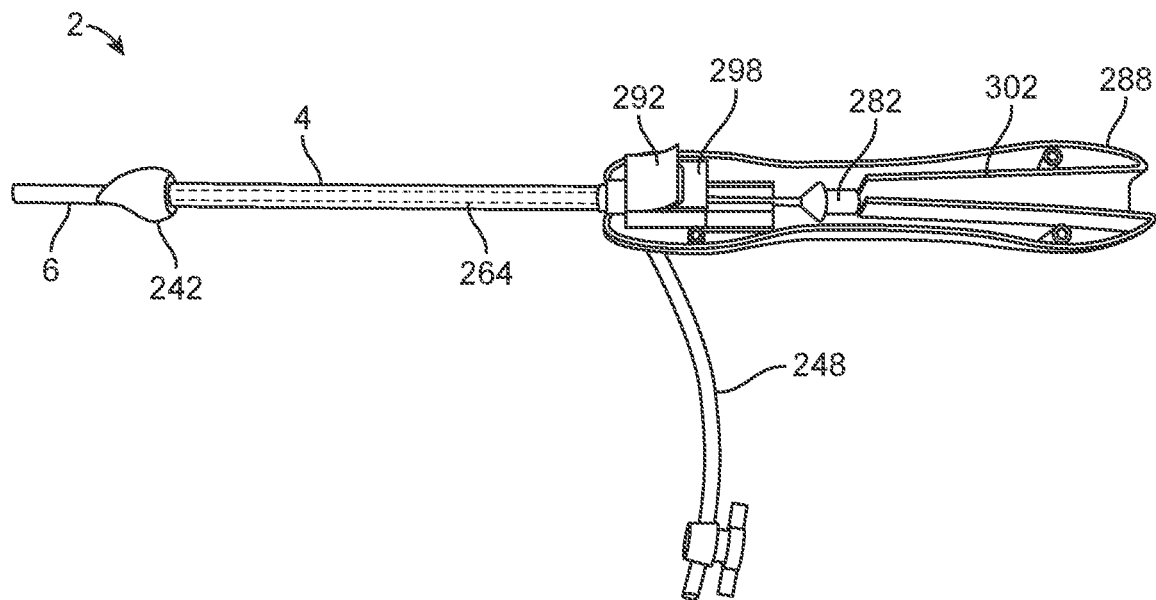

FIG. 17D shows the next step of the eversion process with inner catheter button 298 engaging outer catheter release button 292 and pusher luer hub 310 reaching mechanical detent of pusher engagement tabs 302.

Figure 17E:
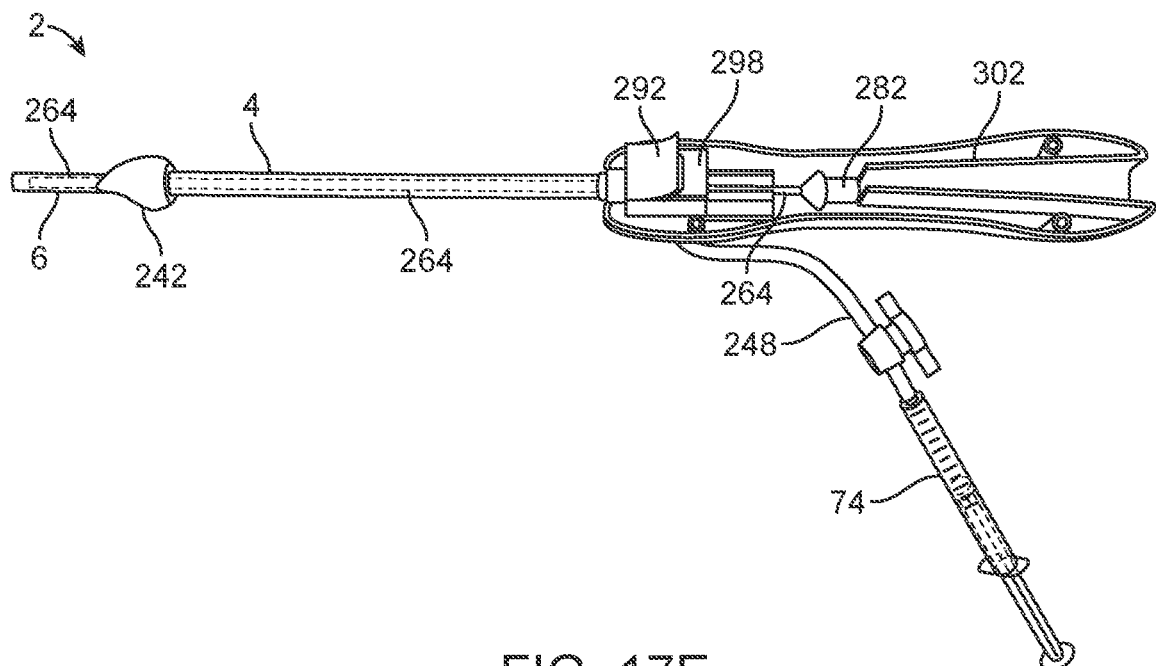

FIG. 17E shows the next step in the IUD delivery process with syringe 74 connected to extension tubing and stopcock 248 to draw negative pressure within everting catheter system 2. Negative pressure withdraws the hydraulic energy in the everting membrane 6.

Figure 17F:
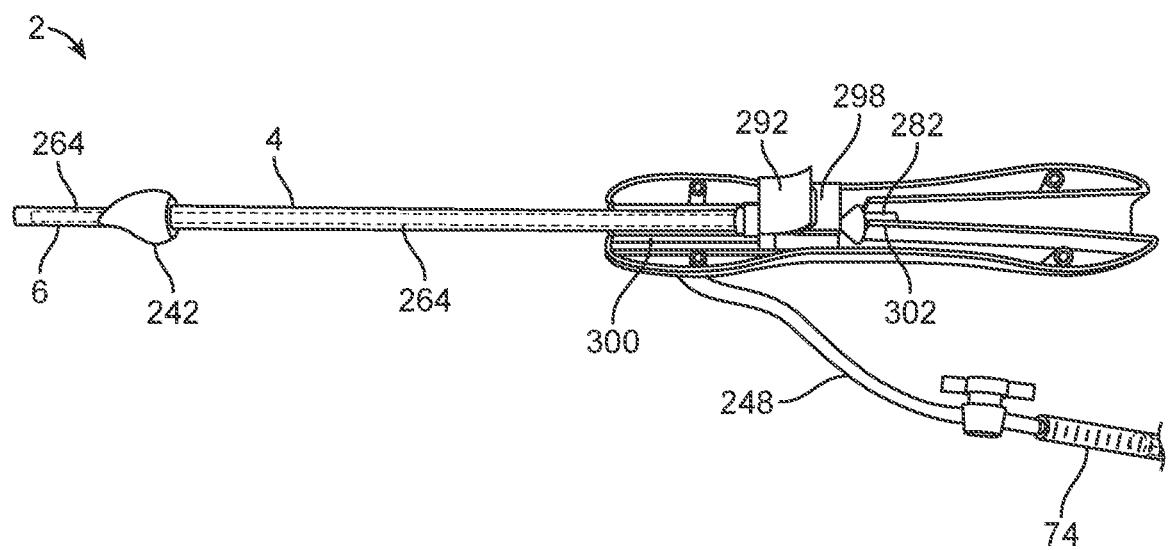

FIG. 17F shows the next step in the IUD delivery process with outer catheter release button 292 retracted and thereby retracting the outer catheter 4, everting membrane 6, and inner catheter 8 while maintaining the position of the pusher 264 relative to the housing 288. Pusher engagement tabs 302 prevent the pusher luer hub 310 from retracting and thereby maintaining the position relative to the housing 288.

Figure 17G:
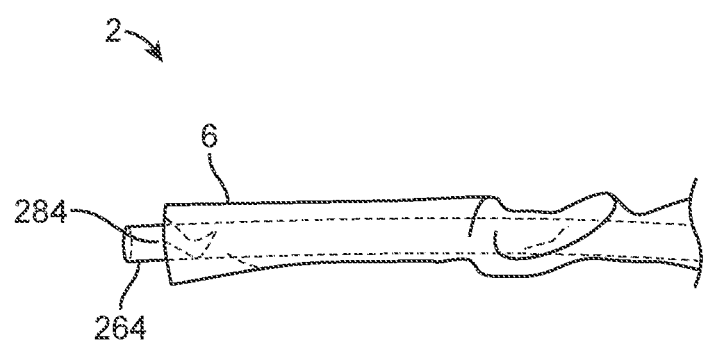

FIG. 17G shows a close-up photograph of the distal end of the everting membrane 6 with hydraulic energy removed from everting catheter system 2 and with distal end of pusher 264 extending beyond the distal opening of the everting membrane 6. Split tube opening 284 is at the distal end of pusher 264 and illustrates that the distal end of pusher 264 can exit everting membrane 6.

Figure 17H:
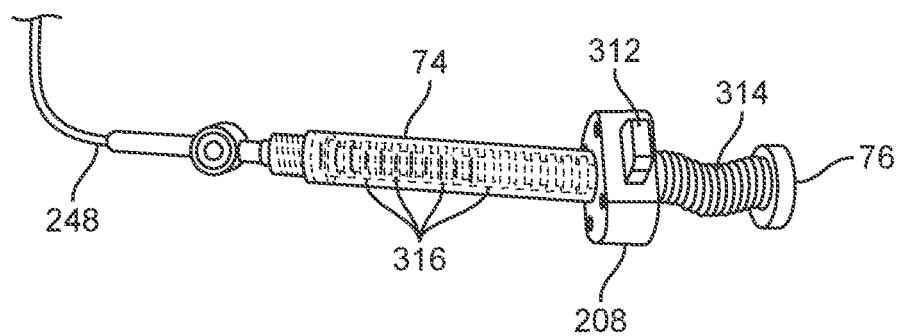

FIG. 17H shows an alternative type of syringe 74 with plunger spring 314 on plunger 76. Engagement button 312 can translate within syringe housing 208 to lock onto ridges 316 on multiple locations on plunger 76. When depressed, engagement button 312 can lock plunger spring 314 in a compressed condition.

Figure 17I:
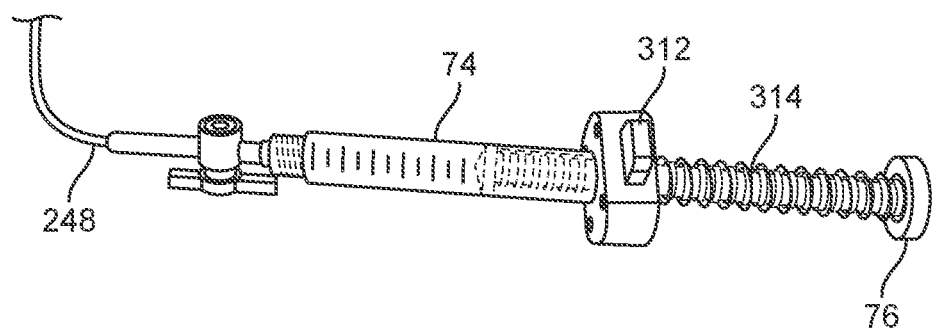

FIG. 17I shows syringe 74 with engagement button 312 released allowing plunger spring 314 to expand and retract plunger 76 back to provide negative pressure within syringe 74 and an everting catheter system 2 (not shown).

Figure 18A:
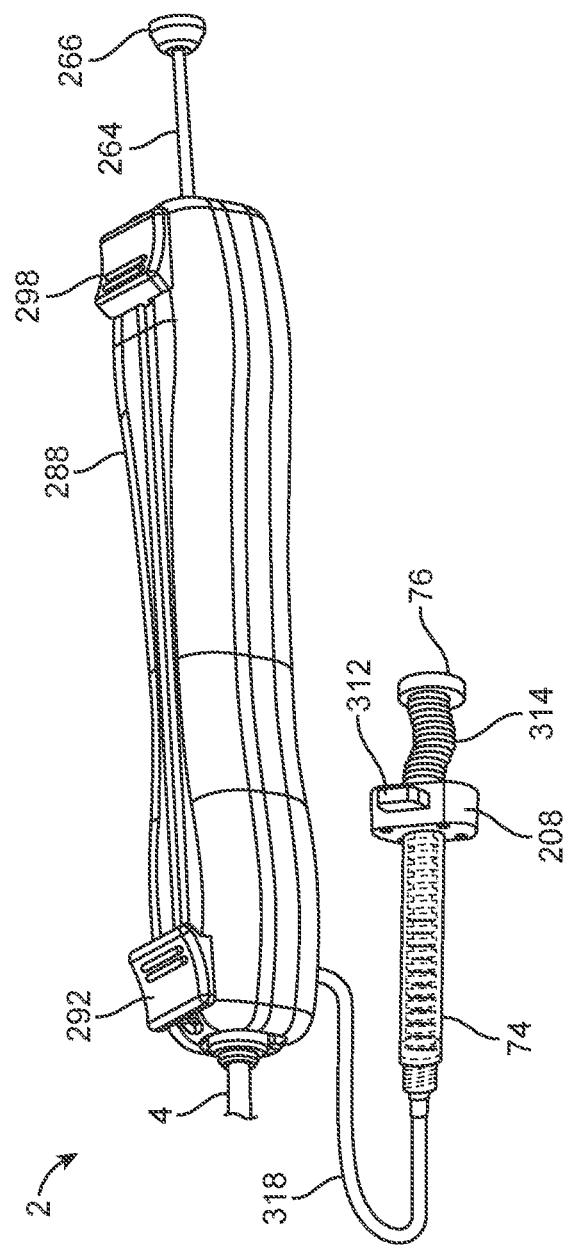
FIGS. 18A to 18C illustrate mechanisms for automatically providing negative pressure during the IUD release step of the delivery process. In addition, irrigation through the central lumen can be provided separately or in conjunction with negative pressure to facilitate the IUD release step.
Figure 18B:
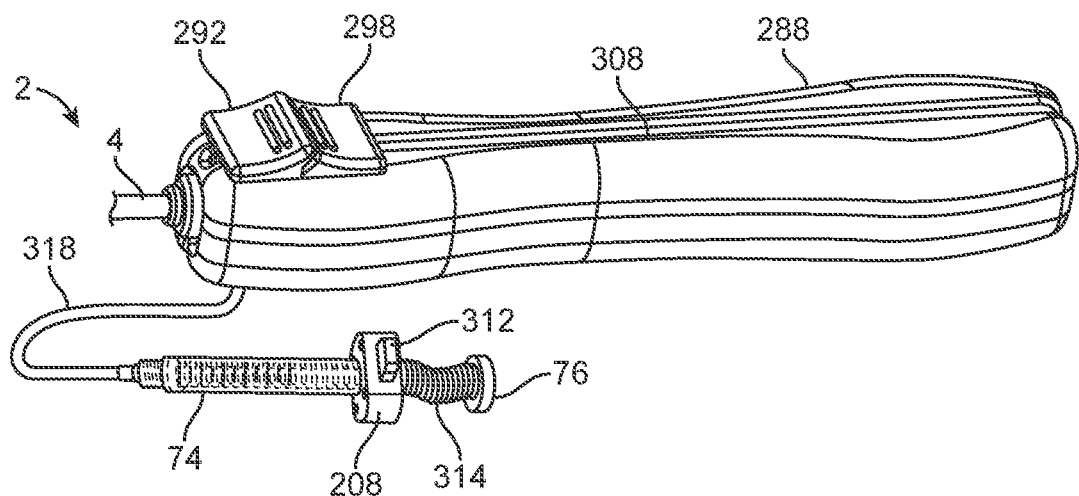
Figure 18C:
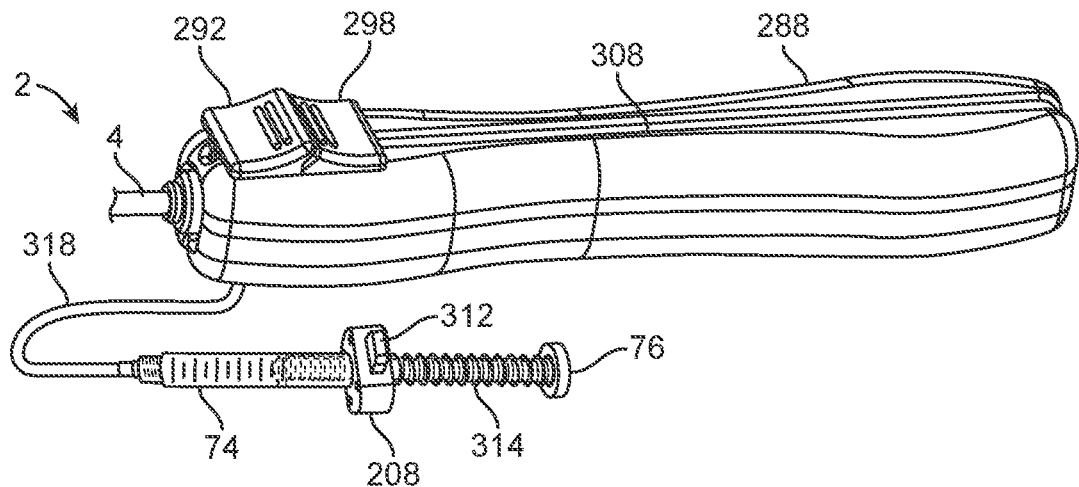

FIGS. 18A through 18C illustrate another embodiment of everting catheter system 2 that automatically provides negative pressure to remove hydraulic energy in the everting catheter at the step of releasing the IUD (not shown) during the delivery and placement procedure. FIG. 18A shows everting catheter system 2 with housing 288 and syringe 74 mounted or attached to the bottom posterior surface of the housing. Syringe 74 can have plunger spring 314 compressed and engagement button 312 locked into syringe housing 208. Syringe 74 is connected via inflation tubing 318 as a conduit for the hydraulic energy within everting catheter system 2.

FIG. 18B shows the advancement of inner catheter button 298 in housing slot 308. Advancement of inner catheter button 298 translates inner catheter (not shown) within outer catheter 4 and advancing everting membrane and IUD (both not shown).

FIG. 18C shows the next step in the IUD delivery and placement process. The depression of outer catheter release button 292 forces engagement button 312 to release plunger spring 314 and plunger 76 to create negative pressure in the everting catheter system 2 via inflation tubing 318. At this point the outer catheter release button can be retracted back along housing slot 308 to retract the outer catheter 4, everting membrane and inner catheter (not shown) while maintaining the position of pusher (not shown) and releasing the IUD from the everting membrane (both not shown).

Figure 19A:
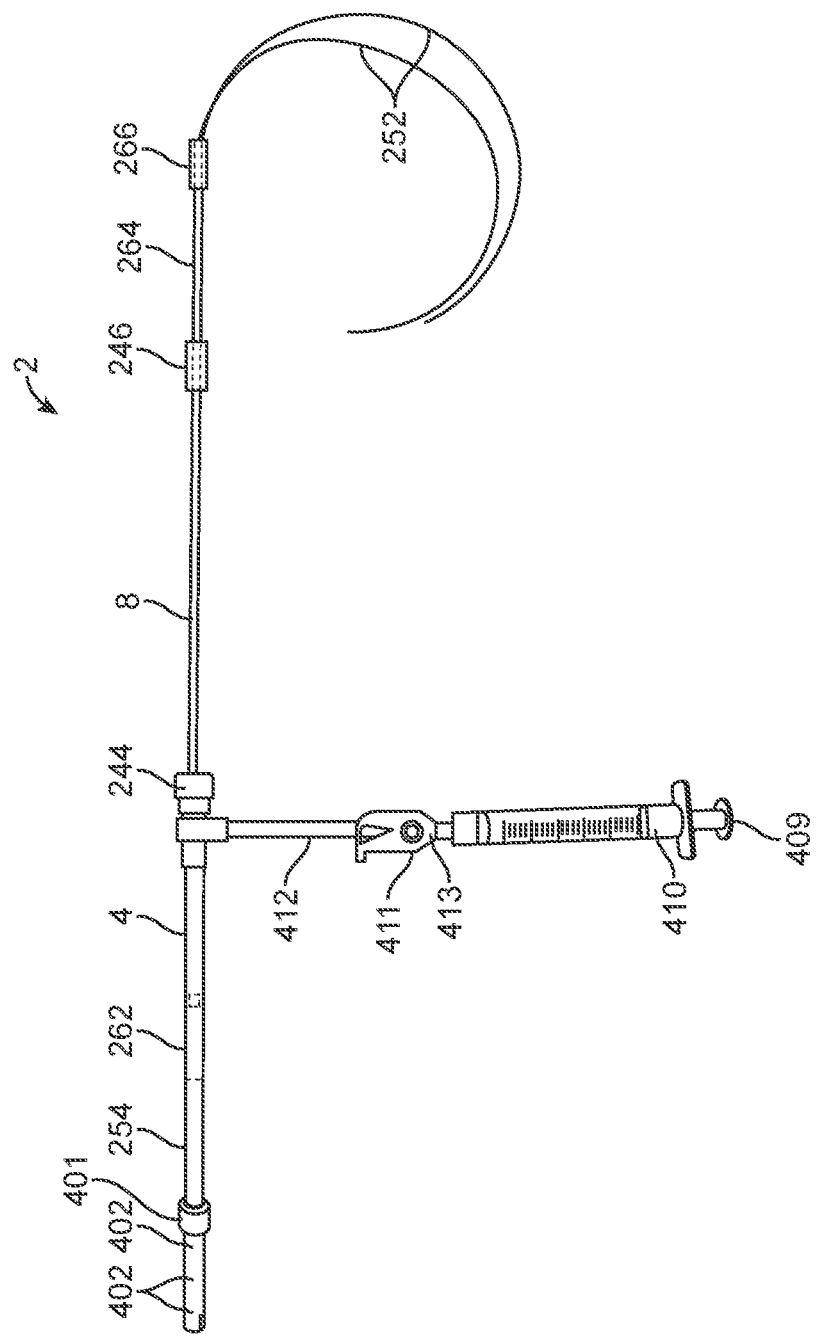
FIG. 19A illustrates an everting catheter system for delivering an IUD.

FIG. 19A illustrates an everting catheter system 2 for delivering an IUD in the inverted state. IUD 254 can be loaded in a collapsed condition within balloon membrane (not visible) and inner catheter 8. Inner catheter 8 can be within outer catheter 4. At the distal end of outer catheter 4, moveable flange can be a marker for insertion depth with indicia 402. The proximal end of outer catheter 4 there is a t-fitting 244 for pressurization of the everting balloon with x-ring valve (not shown) for the translation of inner catheter 8. Inner catheter 8 has proximal hub 246 that can be a luer connector, knob, or handle for the manipulation of inner catheter. Within the central lumen of inner catheter 8 is pusher 264 with lumen for IUD suture(s) 252. Pressurization of everting catheter system 2 can be performed by syringe 410 and syringe plunger 409 that can be connected by the user or physician to connector 413 that can be connected to compliant tube 412. Pinch clamp 411 can be used by the user or physician to close compliant tube 412 to maintain pressure within the everting balloon. Once pressurized, syringe 410 can be disconnected and removed from the everting catheter system 2 prior to insertion within the patient.

Figure 19B:
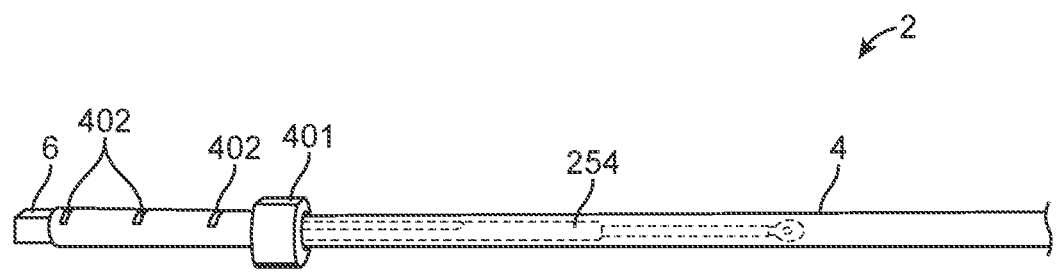
FIGS. 19B to 19D are close-up views of the everting catheter system.
Figure 19C:
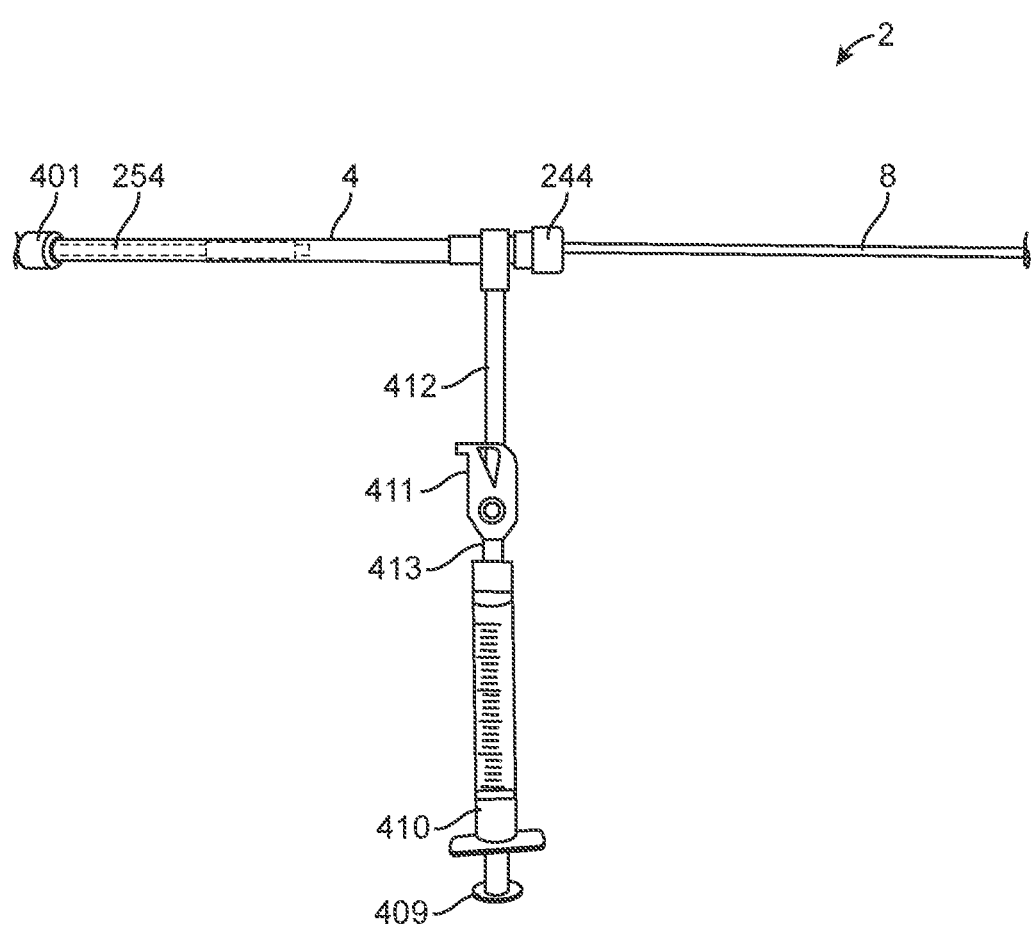
Figure 19D:
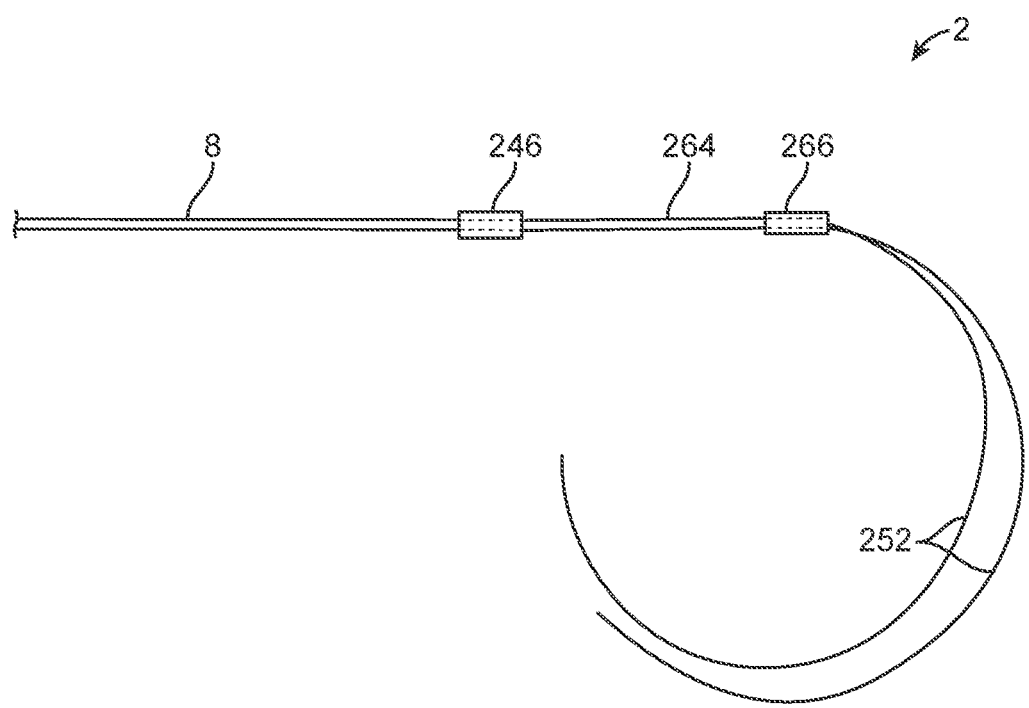

FIGS. 19B to 19D are close-up views of different sections of everting catheter system 2. FIG. 19B is a close-up view of the distal end of outer catheter 4 with the initial portion of everting balloon 6 visible exiting the distal end outer catheter 4. The distal end opening of outer catheter 4 have an acorn tip or no acorn tip and a smooth, rounded, low profile distal tip. The distal end can have indicia 402 which denote 7 cm, 8 cm, 9 cm, and 10 cm markings for example, for showing the user (e.g., physician) an indication of insertion depth. Moveable flange 401 can be placed by the user (e.g., physician) to provide a visible and tactile indicator for insertion depth. Visible within outer catheter 4 can be IUD 254 in a collapsed, loaded, low profile state within the everting balloon and inner catheter (not visible).

FIG. 19C is a close-up view of the pressurization system for everting catheter system 2. Pressurization of the everting catheter 2 can be performed by syringe 410 filled with saline, sterile water, air, or an inert gas, or combination of gases and fluid media. Depression of syringe plunger 409 by the user or physician supplies hydraulic energy to the everting balloon. Syringe 409 can have a volume of 1 cc, 3 cc, 5 cc, or 10 cc, for example, 3 cc as shown. Other volumes are possible. Pressurization of the everting catheter system 2 can distend compliant tube 412. Compliant tube 412 can be made from silicone and/or other elastomeric materials, such as polyurethane, rubber, and TPE, or combinations thereof. Compliant tube 412 can maintain a near constant pressure within everting catheter system 2 during inversion and eversion. Compliant tube 412 can provide a mitigation from the user or physician inadvertently putting in too much pressure within the everting catheter system 2 since the silicone tube can continue to distend in response to the added hydraulic pressure. Pressurization amount can 1 to 4 atmospheres with 2 atmospheres as a nominal level. The amount of compliance within the silicone tube can depend upon the durometer of the material, the wall thickness of the tube, and the length of the tube available for distension. As shown for example, compliant tube 412 can be silicone with a durometer of 50 A, 6 cm in length, with an outer diameter of 4.75 mm and wall thickness of 1 mm. The pressurization system can be closed by the user with pinch clamp 411, for example to close the internal lumen of compliant tube 412 once pressurized by syringe 410. Other tubing closure devices can be used, such as stopcocks, gate valves, roller clamps, or combinations thereof. A one-way check valve or a luer-activated valve can be on complaint tube 412 instead of or in combination with connector 413 to allow for one-way pressurization without requiring the user to actuate a closure device to close and maintain pressure within compliant tube 412 and everting catheter system 2. Hydraulic pressure supplied by syringe 410 and syringe plunger 409 can be in fluid communication with everting catheter system 2 through t-fitting 244 with x-ring valve (not shown) maintaining pressure during eversion of balloon membrane and the translation of inner catheter 8 within outer catheter 4. Inner catheter 8 can be made from nylon, Pebax, polypropylene, polyethylene, or combinations thereof. Inner catheter 8 can extend from the distal end of the fully everted balloon to the proximal end of t-fitting 244 with an outer diameter of 4 mm and an inner diameter of 3 mm.

FIG. 19D is a close-up view of the proximal portion of everting catheter system 2 and illustrates inner catheter 8 with proximal connector hub 246 with central through hole. Within the central through hole can be pusher 264 with pusher hub 266 with central through hole with IUD sutures 252. Proximal connector hub 246 and pusher hub 266 can be luer connectors to allow for the connection of syringes or tubing for the injection of fluid, saline, or gas media for distention of the uterine cavity for ultrasound, fluoroscopic, or endoscopic visualization. Proximal connector hub 246 and pusher hub 266 can be handles or knobs for manipulation of the catheters by the user or physician. Pusher 264 can be made from nylon, Pebax, polypropylene, polyethylene, or combinations thereof. Pusher 264 tubing can have an outer diameter of 2 mm and inner diameter of 1.25 mm and a length that approximates the entire length of everting catheter system 2, for example, to allow the user or physician to expel the IUD from inner catheter 8 during placement within the uterine cavity.

Figure 20A:
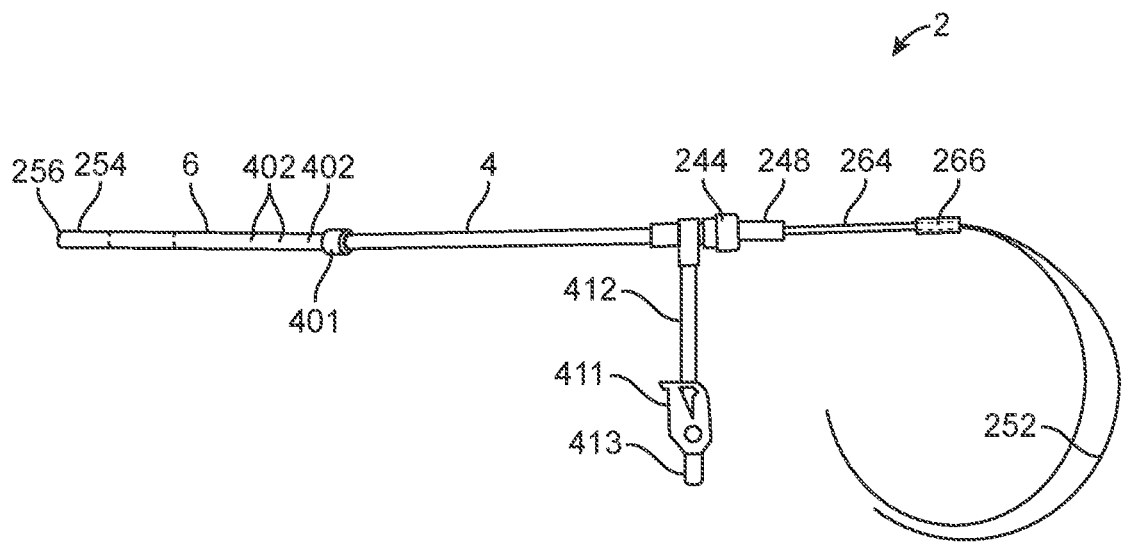
FIG. 20A illustrates the everting catheter system after full eversion of the balloon in the process of delivering an IUD.

FIG. 20A illustrates the everting catheter system 2 after full eversion of the balloon in the process of delivering an IUD. IUD 254 can be in a collapsed, loader state within inner catheter 8 and everting balloon 6. Outer catheter 4 can contain indicia markings 402 and depth insertion marker flange 401. Outer catheter 4 can be connected to t-fitting 244 with x-ring valve (not shown) and can be connected to compliant tube 412 with luer connector 413 and tubing pinch clamp 411 for hydraulic pressurization of everting catheter system 2. Immediately proximal to t-fitting 244 can be proximal connector hub 248 denoting full eversion of the everting balloon and full translation of inner catheter (not visible). Proximal to the proximal connector hub 248 is pusher 264 and pusher hub 266. Proximal to pusher hub 266 can be IUD sutures 252 seen beyond the central lumen of the tubing.

Figure 20B:
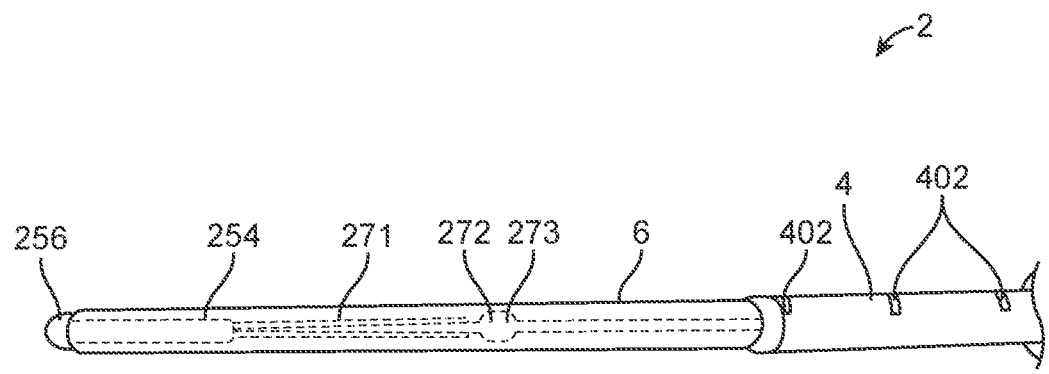
FIG. 20B is a close up view of the distal end of the everted balloon and IUD.

FIG. 20B is a close-up view of the distal end of the everting catheter system 2 with fully everted balloon 6 and IUD 254. Distal end of inner catheter (not visible) can be connected to everting balloon 6 and rounded distal ends 256 of IUD 254 can be immediately distal to the fully everted balloon 6. Visible through the everted balloon 6 and inner catheter can be portions of IUD 254 including copper wire 271, IUD stem hole 272, suture knot 273 and IUD sutures (not visible). Everting balloon 6 can be connected to outer catheter 4 with indicia markings 402. For example, everting balloon 6 can be 6 cm long to traverse the length of the cervix and which can be 3.5 cm in length from the exocervix to the internal cervical os. Different lengths of everting balloon 6 can be used to approximate the uterine lengths of different patients. Everting balloon can, for example, have an outer diameter of 4 mm in the pressurized state of 2 atmospheres and a wall thickness of 0.0015" thousandths of an inch. Everting balloon can be made from irradiated polyolefin, polyethylene, Pebax, polyurethane, other biocompatible materials that can create a hydraulic everting balloon, or combinations thereof.

Distal end of inner catheter (not visible) can have an internal diameter that, for example, can allow for the collapsed IUD to fit within the tubing. For example, an internal diameter of 3 mm can allow the collapsed IUD to fit within the tubing but keep the rounded distal ends 256 protruding distal to the inner catheter (not visible) and the everting balloon 6. Distal end of pusher (not visible) can be just proximal to IUD stem hole 272 and suture knot 273. Distal end opening of everting balloon 6 can be connected to the distal end of the inner catheter (not visible). When inverted and pressurized, everting balloon 6 can collapse IUD 254 in a lower profile state that facilitates advancement through the cervical canal and into the uterine cavity. When inverted and pressurized, everting balloon 6 can collapse and compress the rounded distal ends 256 together to a low profile, for example, for advancement through the everting catheter system 2, the distal end opening of the outer catheter 4, and the cervical canal and into the uterine cavity.

Figure 20C:
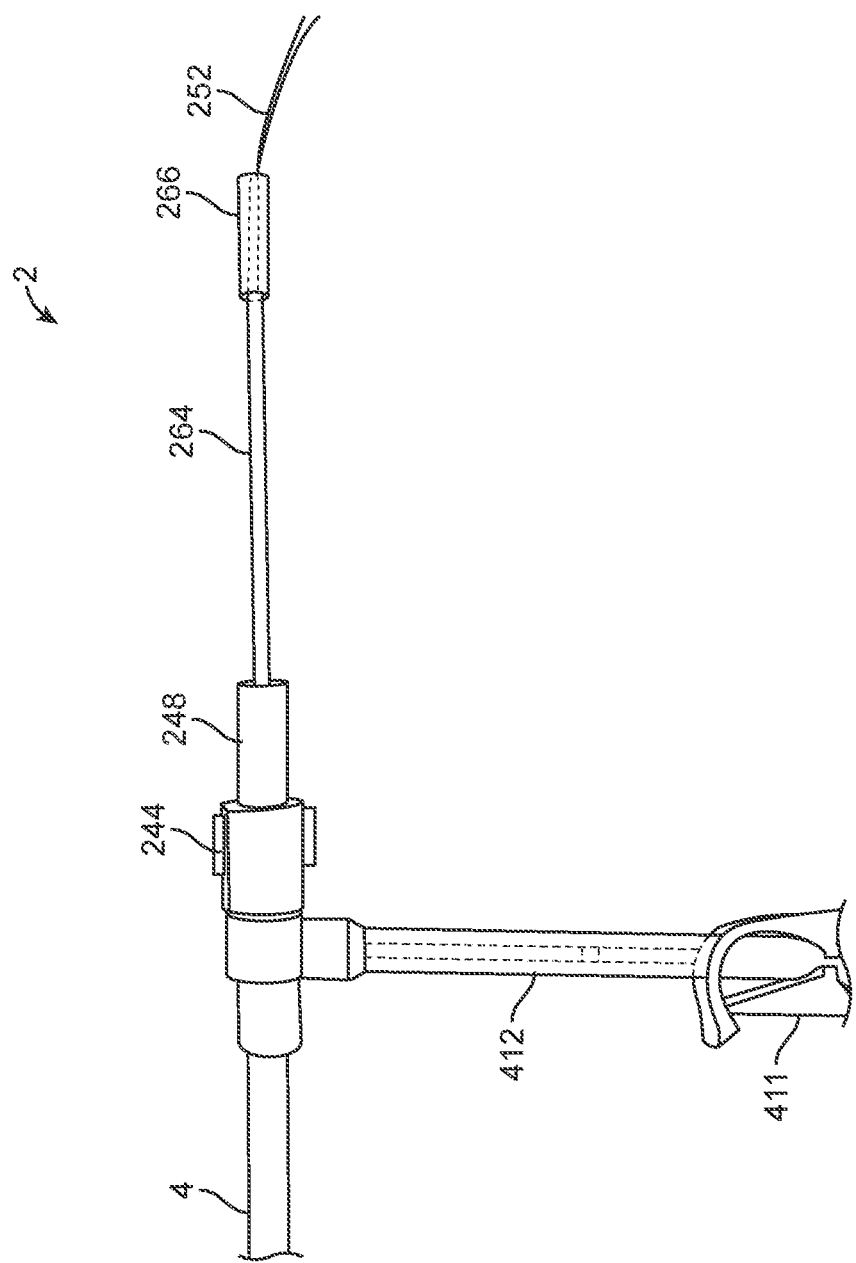
FIG. 20C is a close up view of the proximal portion of the everting catheter system after full eversion in the process of delivering an IUD.

FIG. 20C is a close-up view of the proximal portion of the everting catheter system 2 after full eversion in the process of delivering an IUD 254. Outer catheter 4 can be connected to t-fitting 244 with x-ring (not visible) and is fluidly coupled to compliant tube 412 with tubing pinch clamp 411 shown in the closed condition with hydraulic pressurization within the everting catheter system 2. Proximal connector hub 248 can be seen immediately proximal to t-fitting 244, for example, denoting full eversion of the everting balloon (not shown) and full translation of the inner catheter (not visible). Within proximal connector hub 248 can be pusher 264 with pusher hub 266 on its proximal end with IUD sutures 252 seen exiting through the central lumen of pusher 264.

Figure 21A:
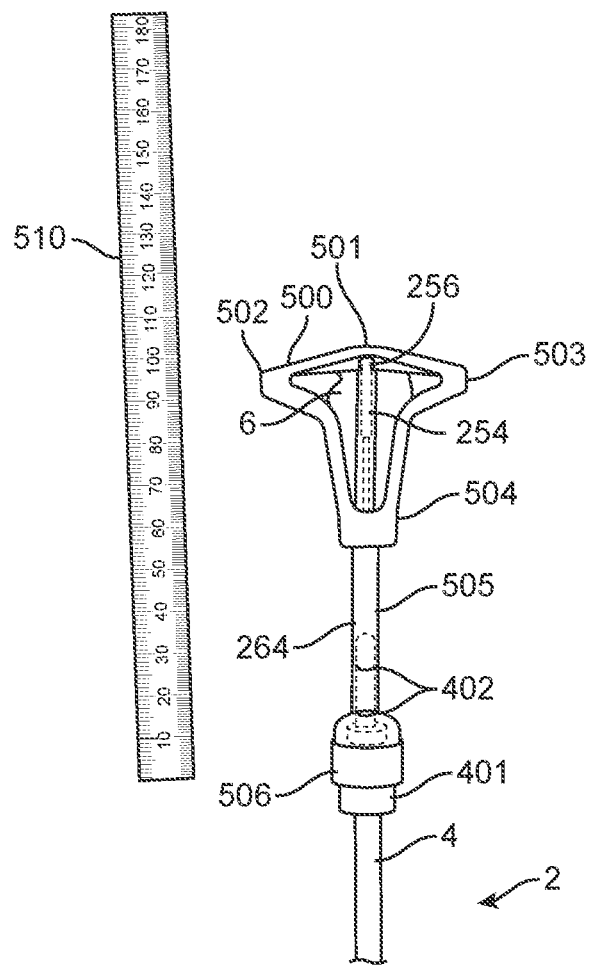
FIGS. 21A to 21C illustrate the process of delivering an IUD within a simulated uterine cavity model.
Figure 21B:
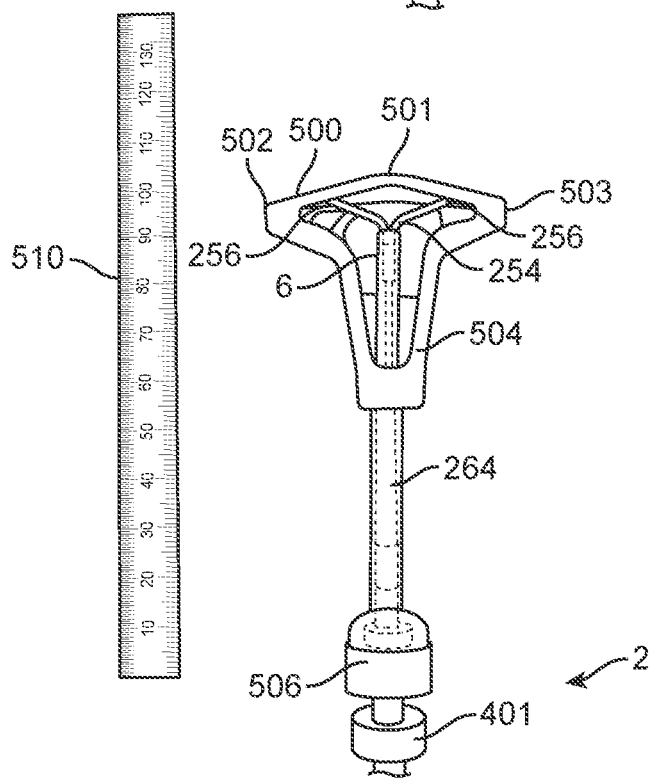
Figure 21C:
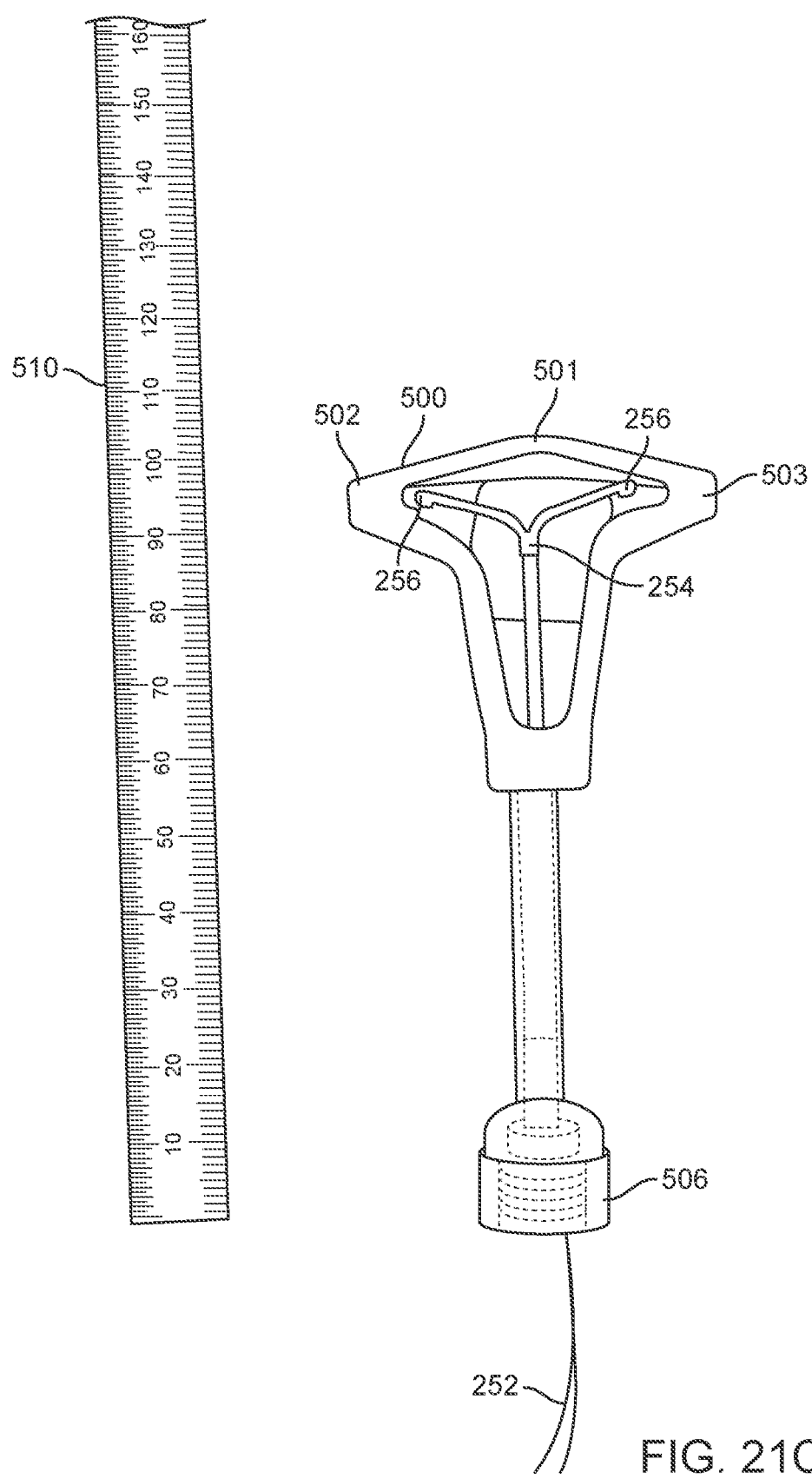

FIGS. 21A to 21C illustrate the process of delivering an IUD within a simulated uterine cavity model 500 (standing in for a patient's uterine cavity and other respective anatomy for illustrative purposes) with metric scale 510 provided for reference. FIG. 21A illustrates the placement of IUD 254 within simulated uterine cavity model 500 with fundal portion 501 which simulates the cranial apex of the uterine cavity, and cornual regions 502 (denoting the patient's right fallopian tube os) and 503 (denoting the patient's left fallopian tube os). Simulated uterine cavity model can contain lower uterine segment 504 with simulated cervical canal 505 and simulated exocervix 506. Everting catheter system 2 can have everted balloon 6 fully everted with rounded distal ends 256 of IUD 254 approximating the fundus 501 of the uterine cavity and distal to the everted balloon 6. Pusher 264 can be proximal to IUD 254. Flange 401 can abut the exocervix 506 with an insertion depth of approximately 9 cm, for example.

FIG. 21B illustrates a next (e.g., intermediate) step in the process of IUD placement with everting catheter system 2. Everting catheter system 2 can be retracted 1.5 cm as seen by flange 401 now being a distance, for example, of 1.5 cm from exocervix 506. In combination, IUD 254 can be expelled from the distal end of everting balloon 6 with pusher 264 and retraction of everting catheter system 2. IUD 254 can have rounded distal ends 256 extending outward towards cornual regions 502 and 503.

FIG. 21C illustrates a next (e.g., final) step of IUD 254 placement with the everting catheter system (not shown) that can be completely removed from simulated uterine cavity model 500. Rounded distal ends 256 can remain in the cornual regions 502 and 503. IUD sutures 252 can be visible exiting the exocervix 506. The user or physician can trim the excess length of IUD sutures 252 depending upon the amount of excess IUD suture or type of IUD.

FIGS. 22A to 22E illustrate a packaging configuration for the transit and loading of the everting catheter system 2 for delivering an IUD. Everting catheter system 2 can be placed onto pouch card 600 in the fully everted position with IUD 254 at the distal end of the everting balloon (not visible). Pouch card 600 and everting catheter system 2 can be placed into a sealed pouch (not shown) for sterilization, shipping, and eventual usage by a physician. Pouch card 600 can be made from clean laminated paper card stock, PETG, polypropylene, polyvinyl chloride, PET, or combinations thereof. Affixed to pouch card 600 can be protective tube 601 which can be, for example, 6.5 cm in length with an ID of 4 mm. Protective tube 601 can be sized in length to fit over the fully everted balloon (not visible) and leave IUD 254 in the open configuration with rounded distal ends 256 beyond the distal end of the protective tube 601. Protective tube 601 internal diameter can be sized to allow a non-pressurized everting balloon (not visible) to slide through the central lumen. When everting balloon (not visible) is pressurized, everting balloon outer diameter can contact the internal lumen of protective tube 601. Contacting the internal lumen when pressurized can, for example, allow the user or physician to easily retract the everting balloon and inner catheter for loading and preparation for use. Protective tube 601 can be made from nylon but can be made from polypropylene, PET, Pebax, and other tubing materials used in medical device packaging. T-fitting 244 and proximal connector hub (not visible) can be held in place by pouch tabs 602 with inner catheter (not visible) fully translated into outer catheter 4. Pusher 264, pusher hub 266, and IUD sutures 252 can extend proximal to everting catheter system 2.

Figure 22A:
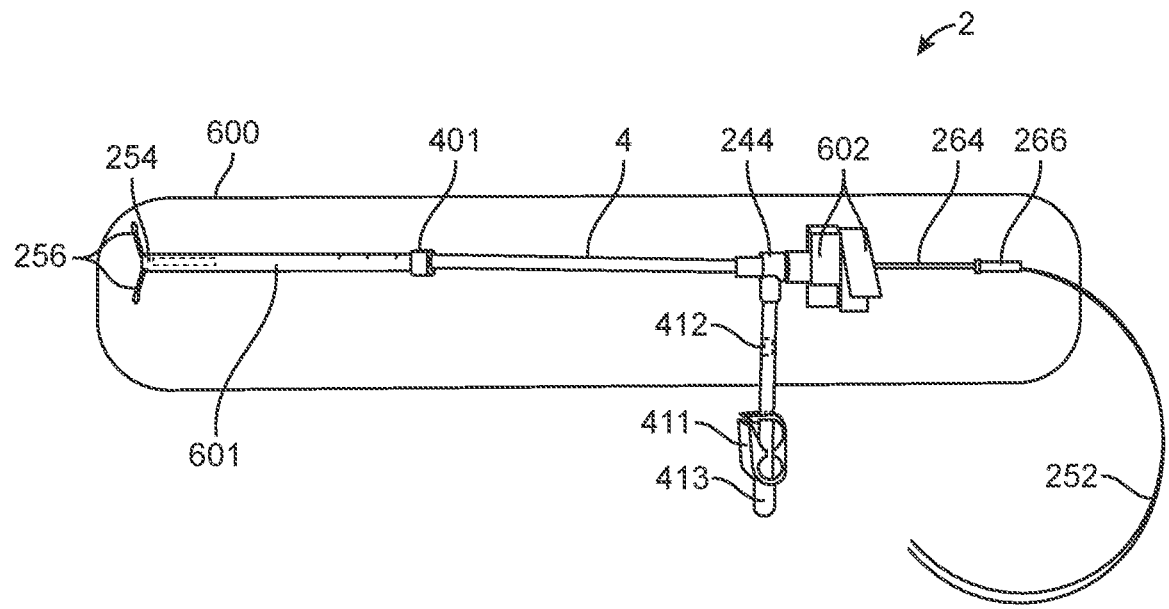
FIGS. 22A to 22E illustrate a packaging configuration for the transit and loading of the everting catheter system for delivering an IUD.
Figure 22B:
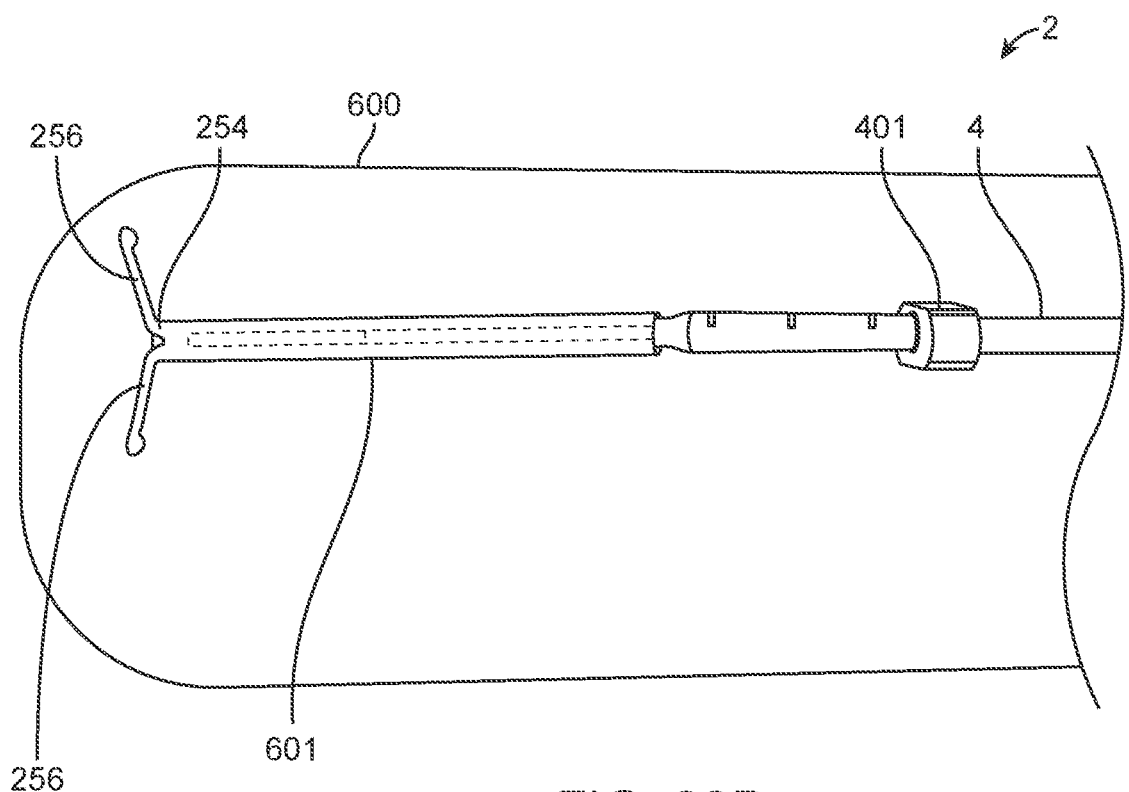

FIG. 22B is a close-up view of a variation of the distal portion of pouch card 600 and protective tube 601 with everting balloon (not visible) fully everted within protective tube 601. IUD 254 can be in an open configuration and can be positioned at the distal end of everting catheter system 2 with IUD sutures (not visible in this view) running through the entire length of the inner catheter and pusher of everting catheter system 2. Proximal end of protective tube 601 can be intubated by the distal end of outer catheter 4.

Figure 22C:
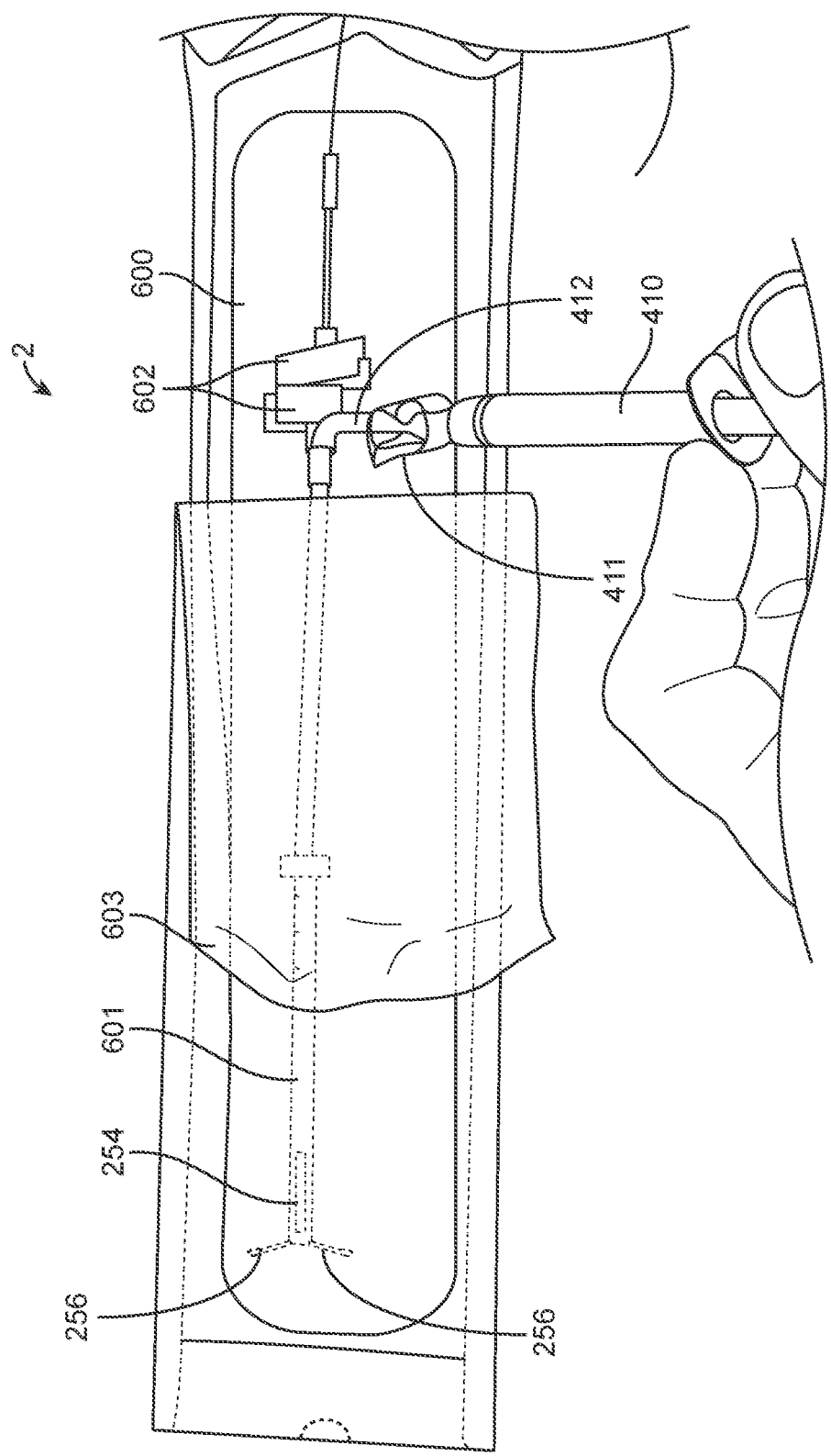

FIG. 22C illustrates a step (e.g., unpacking, assembling, and pressurizing) in the preparation of everting catheter system 2. Pouch 603 can be peeled back halfway to expose the proximal portion of pouch card 600. The user or physician can connect syringe 410 to compliant tube 412 with pinch clamp 411 in the open position. The compliant tube can be rotated upwards or perpendicular to the surface or pouch card 600. The everting catheter system can be pressurized with 3 cc of saline.

Figure 22D:
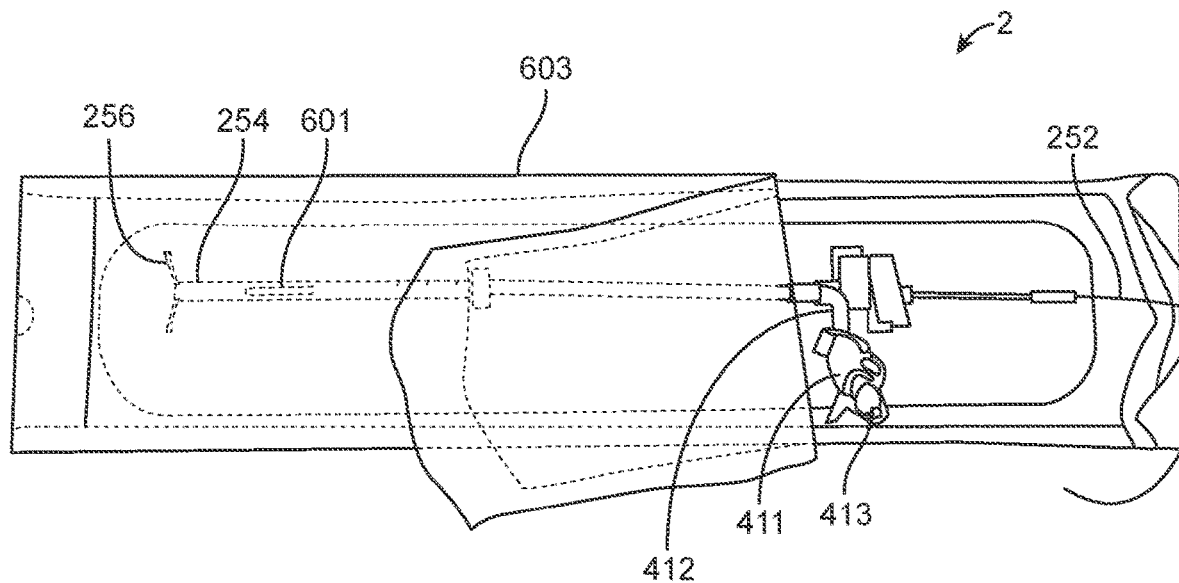

FIG. 22D shows the compliant tube 412 pressurized with pinch clamp 411 can be in the closed position with syringe disconnected and removed from luer connector 413. IUD sutures 252 can then pulled to retract IUD 254 within the distal end of the inner catheter (not visible) within protective tube 601.

Figure 22E:
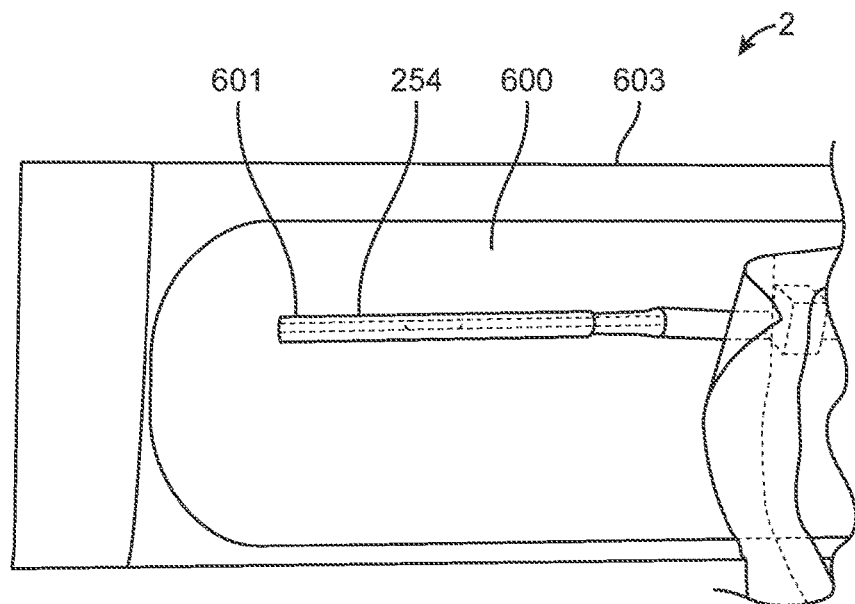

FIG. 22E is a close-up view of the distal portion of pouch card 600 with the IUD 254 that can be in the collapsed and loaded configuration inside the inner catheter (not visible) within protective tube 601. The everting balloon (not visible) can then be fully inverted with inner catheter (not visible) that can be fully translated back, for example, to remove the everting catheter system 2 from the protective tube 601 and pouch 603 in preparation for insertion into the patient.

Any elements described herein as singular can be pluralized (i.e., anything described as "one" can be more than one). Any species element of a genus element can have the characteristics or elements of any other species element of that genus. The media delivered herein can be any of the fluids (e.g., liquid, gas, or combinations thereof) described herein. The patents and patent applications cited herein are all incorporated by reference herein in their entireties. Some elements may be absent from individual figures for reasons of illustrative clarity. The above-described configurations, elements or complete assemblies and methods and their elements for carrying out the disclosure, and variations of aspects of the disclosure can be combined and modified with each other in any combination. All devices, apparatuses, systems, and methods described herein can be used for medical (e.g., diagnostic, therapeutic or rehabilitative) or non-medical purposes.

U.S. Pat. No. 9,028,401, issued May 12, 2015; U.S. Pat. No. 9,101,391, issued Aug. 11, 2015; and U.S. Pat. No. 10,034,986, issued Jul. 31, 2018; and U.S. Published Application Nos. 2019/0009058, published Jan. 10, 2019; 2020/0206463, published Jul. 2, 2020; 2020/0297384, published Sep. 24, 2020; and 2020/0023162, published Jan. 23, 2020 which are all incorporated by reference herein in their entireties.

Any elements described herein as singular can be pluralized (i.e., anything described as "one" can be more than one). Any species element of a genus element can have the characteristics or elements of any other species element of that genus. "Dilation" and "dilatation" are used interchangeably herein. The media 155 delivered herein can be any of the fluids (e.g., liquid, gas, or combinations thereof) described herein. The patents and patent applications cited herein are all incorporated by reference herein in their entireties. Some elements may be absent from individual figures for reasons of illustrative clarity. The above-described configurations, elements or complete assemblies and methods and their elements for carrying out the disclosure, and variations of aspects of the disclosure can be combined and modified with each other in any combination. All devices, apparatuses, systems, and methods described herein can be used for medical (e.g., diagnostic, therapeutic or rehabilitative) or non-medical purposes.

We claim:

1. A system for delivering a device into the reproductive tract of a female comprising:
    a first catheter having a lumen and a distal lumen port, wherein the first catheter has a retracted configuration and an extended configuration;
    an everting balloon attached to the first catheter, wherein at least a length of the everting balloon extends past a distal end of the first catheter when the first catheter is in the extended configuration, wherein the length of the everting balloon that extends past the distal end of the first catheter comprises a check valve when the first catheter is in the extended configuration;
    a second catheter slidably located in the first catheter;
    a third catheter radially outside of the first catheter, wherein a first end of the everting balloon is attached to the third catheter, wherein a second end of the everting balloon is attached to the first catheter; and
    an IUD in the second catheter.

2. The system of claim 1, further comprising a pusher in the second catheter.

3. The system of claim 2, wherein the pusher comprises a connection hub.

4. The system of claim 2, wherein the pusher comprises an irrigation source.

5. The system of claim 2, wherein the system is configured such that the pusher extends the IUD as the IUD is released from the second catheter concurrent with negative pressure being delivered within the everting balloon.

6. The system of claim 1, wherein the system is configured to release the IUD concurrent with delivering negative pressure within the everting balloon.

7. The system of claim 1, further comprising an irrigant, wherein the system is configured to deliver the irrigant through the second catheter concurrent with releasing the IUD from the second catheter.

8. The system of claim 1, further comprising an irrigation source configured to deliver an irrigant through the second catheter.

9. A system for delivering a device into the reproductive tract of a female comprising:
    a first catheter having a lumen and a distal lumen port, wherein the first catheter has a retracted configuration and an extended configuration;
    an everting balloon attached to the first catheter, wherein at least a length of the everting balloon extends past a distal end of the first catheter when the first catheter is in the extended configuration;
    a second catheter slidably located in the first catheter;
    a third catheter radially outside of the first catheter, wherein a first end of the everting balloon is attached to the third catheter, wherein a second end of the everting balloon is attached to the first catheter; and
    an IUD, wherein the second catheter is configured to deliver the IUD.

10. The system of claim 9, further comprising a pusher in the second catheter.

11. The system of claim 10, wherein the pusher comprises a connection hub.

12. The system of claim 10, wherein the pusher comprises an irrigation source.

13. The system of claim 10, wherein the system is configured such that the pusher extends the IUD as the IUD is released from the second catheter concurrent with negative pressure being delivered within the everting balloon.

14. The system of claim 9, wherein the system is configured to release the IUD concurrent with delivering negative pressure within the everting balloon.

15. The system of claim 9, further comprising an irrigant, wherein the system is configured to deliver the irrigant through the second catheter concurrent with releasing the IUD from the second catheter.

16. The system of claim 9, further comprising an irrigation source configured to deliver an irrigant through the second catheter.

* * * * *